(12) United States Patent
Schmura et al.

(10) Patent No.: US 9,107,763 B2
(45) Date of Patent: Aug. 18, 2015

(54) ARTICULATING INTERVERTEBRAL IMPLANT

(71) Applicants: Kurt Schmura, West Chester, PA (US); Marc Reichen, West Chester, PA (US)

(72) Inventors: Kurt Schmura, West Chester, PA (US); Marc Reichen, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 154 days.

(21) Appl. No.: 13/644,606

(22) Filed: Oct. 4, 2012

(65) Prior Publication Data

US 2014/0100658 A1 Apr. 10, 2014

(51) Int. Cl.
*A61F 2/44* (2006.01)
*A61F 2/30* (2006.01)

(52) U.S. Cl.
CPC ..... *A61F 2/4425* (2013.01); *A61F 2002/30013* (2013.01); *A61F 2002/3065* (2013.01); *A61F 2002/3092* (2013.01); *A61F 2002/3098* (2013.01); *A61F 2002/30245* (2013.01); *A61F 2002/30253* (2013.01); *A61F 2002/30365* (2013.01); *A61F 2002/30372* (2013.01); *A61F 2002/30654* (2013.01); *A61F 2002/30884* (2013.01); *A61F 2002/30934* (2013.01); *A61F 2310/00017* (2013.01); *A61F 2310/00023* (2013.01); *A61F 2310/00029* (2013.01); *A61F 2310/00167* (2013.01); *A61F 2310/00179* (2013.01); *A61F 2310/00407* (2013.01)

(58) Field of Classification Search
CPC ........... A61B 17/70; A61F 2/44; A61F 2/442; A61F 2/4425; A61F 2002/443

USPC .......... 606/246–249; 623/17.11, 17.14–17.16
See application file for complete search history.

(56) References Cited

U.S. PATENT DOCUMENTS

| | | | |
|---|---|---|---|
| 6,039,763 | A | 3/2000 | Shelokov |
| 6,706,068 | B2 | 3/2004 | Ferree |
| 6,997,955 | B2 | 2/2006 | Zubok et al. |
| 7,083,649 | B2 | 8/2006 | Zucherman et al. |
| 7,320,707 | B2 | 1/2008 | Zucherman et al. |
| 7,550,009 | B2 | 6/2009 | Arnin et al. |
| 8,337,500 | B2 | 12/2012 | Bertagnoli et al. |
| 2005/0165487 | A1* | 7/2005 | Muhanna et al. .......... 623/17.15 |

(Continued)

FOREIGN PATENT DOCUMENTS

| | | |
|---|---|---|
| WO | WO 03/090649 | 11/2003 |
| WO | WO 2004/019828 | 3/2004 |
| WO | WO 2006/114646 | 11/2006 |

OTHER PUBLICATIONS

International Patent Application No. PCT/US2012/064358: International Search Report dated Aug. 26, 2013, 4 pages.

*Primary Examiner* — Larry E Waggle, Jr.
(74) *Attorney, Agent, or Firm* — Baker & Hostetler LLP

(57) ABSTRACT

An intervertebral disc implant for use in the spine includes a superior endplate and an inferior endplate. The superior endplate is configured to articulate about the inferior endplate in an anterior-posterior direction during flexion and extension. The superior endplate is further configured to axially rotate about the inferior endplate during axial rotation, and is further configured to articulate about the inferior endplate along a medial-lateral direction during lateral bending. During axial rotation, the superior endplate is induced to articulate about the inferior endplate along the medial-lateral direction. During lateral bending, the superior endplate is induced to axially rotate about the inferior endplate.

24 Claims, 45 Drawing Sheets

(56) References Cited

U.S. PATENT DOCUMENTS

| | | |
|---|---|---|
| 2006/0004453 A1 | 1/2006 | Bartish, Jr. et al. |
| 2006/0089720 A1 | 4/2006 | Schneier |
| 2006/0149372 A1* | 7/2006 | Paxson et al. ............. 623/17.11 |
| 2007/0250170 A1 | 10/2007 | Moumene et al. |
| 2008/0195212 A1* | 8/2008 | Nguyen et al. ............. 623/17.16 |
| 2011/0054617 A1* | 3/2011 | Sekhon et al. ............. 623/17.13 |
| 2011/0087331 A1* | 4/2011 | Reichen et al. ............. 623/17.16 |
| 2012/0232661 A1* | 9/2012 | Nguyen et al. ............. 623/17.16 |

* cited by examiner

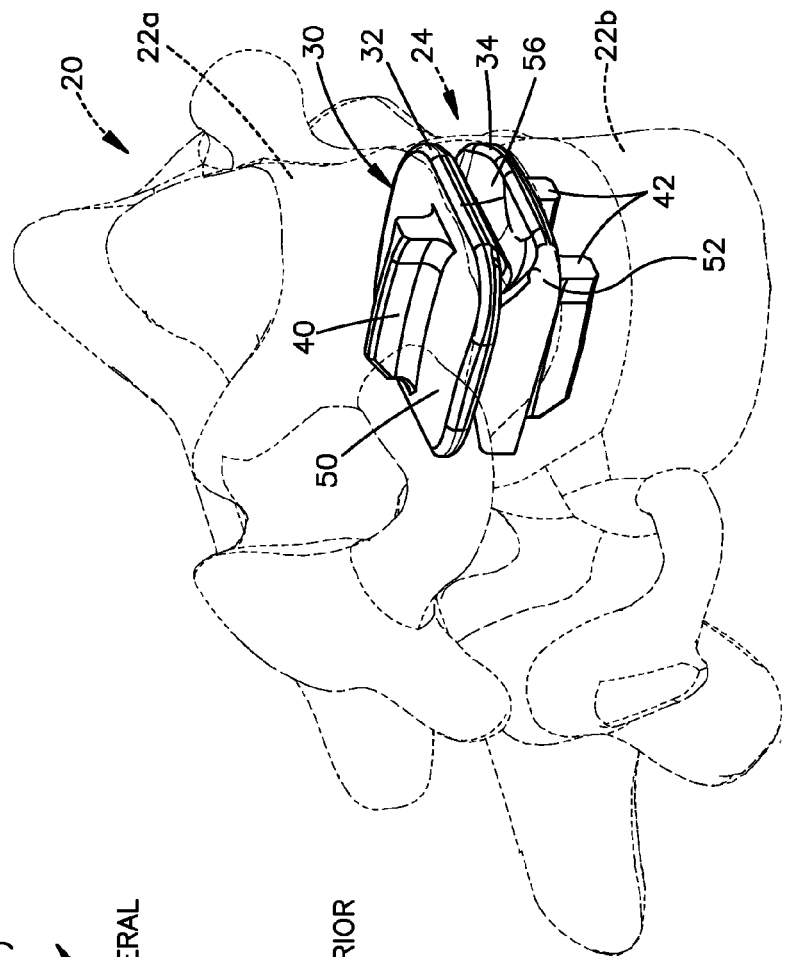
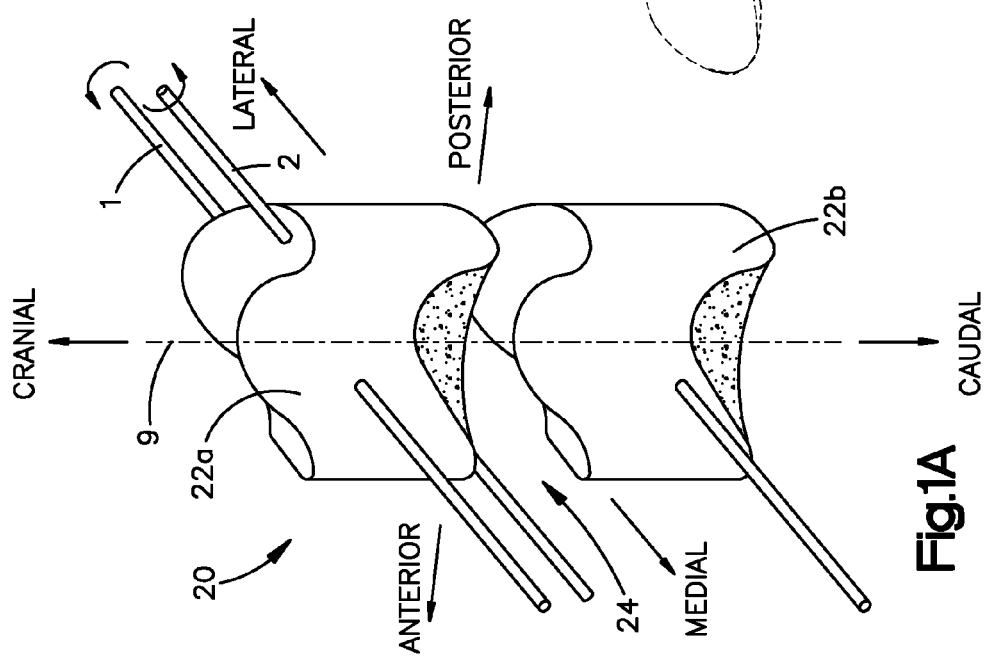
Fig.1B
Fig.1A

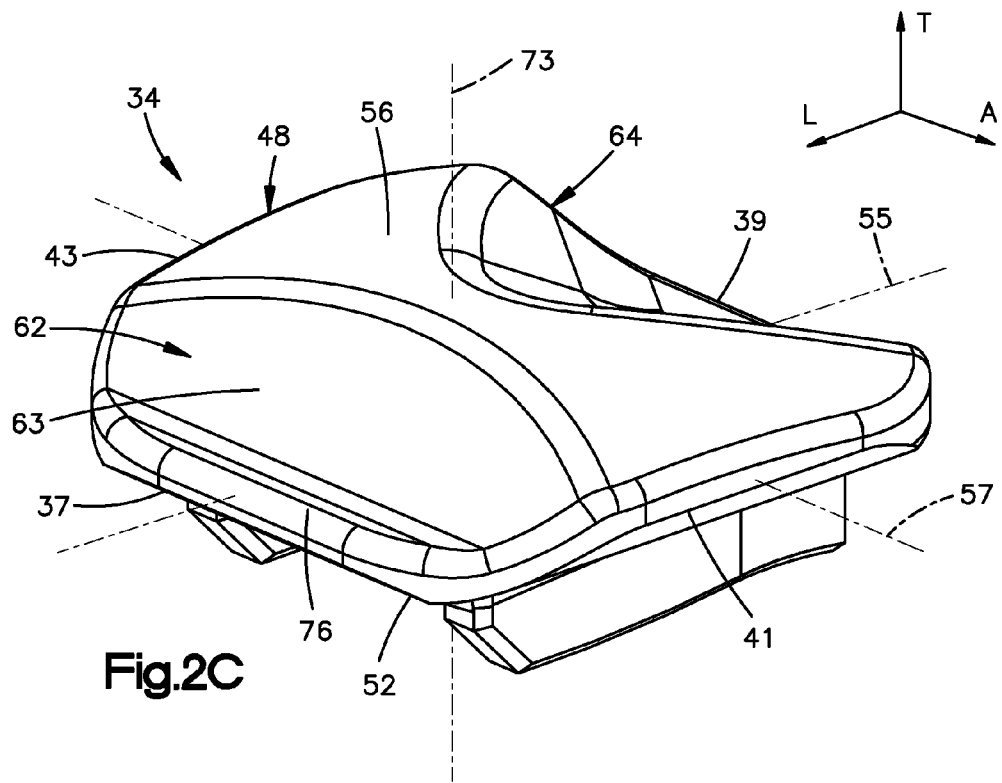
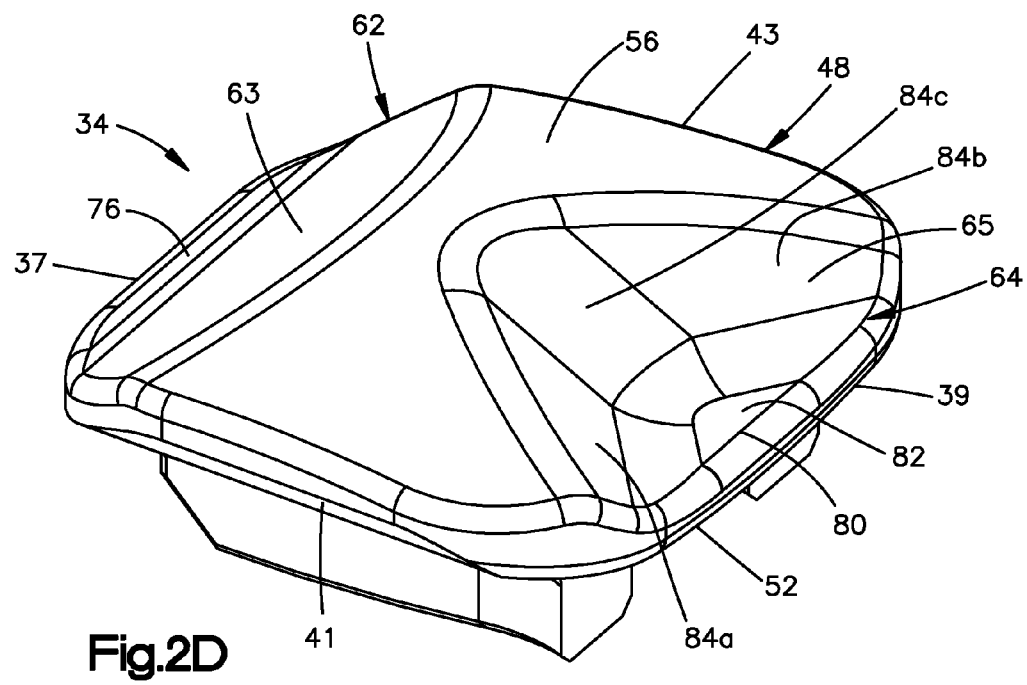

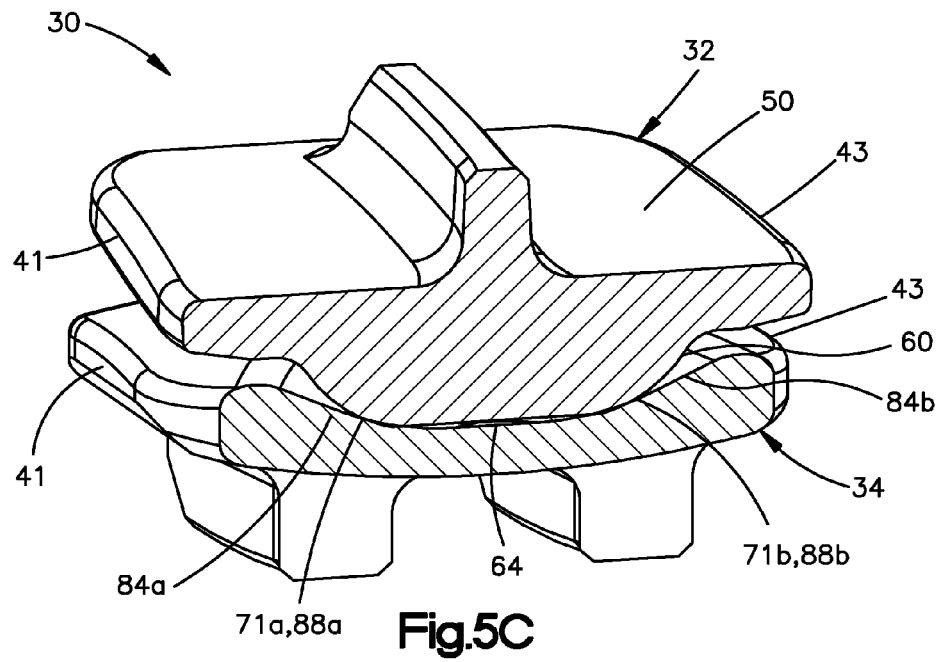
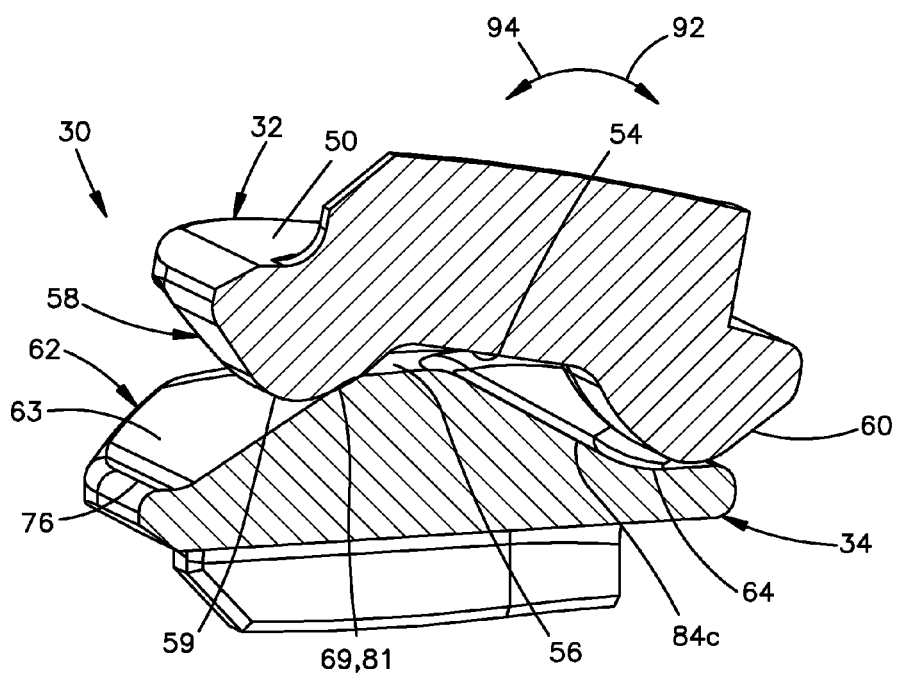

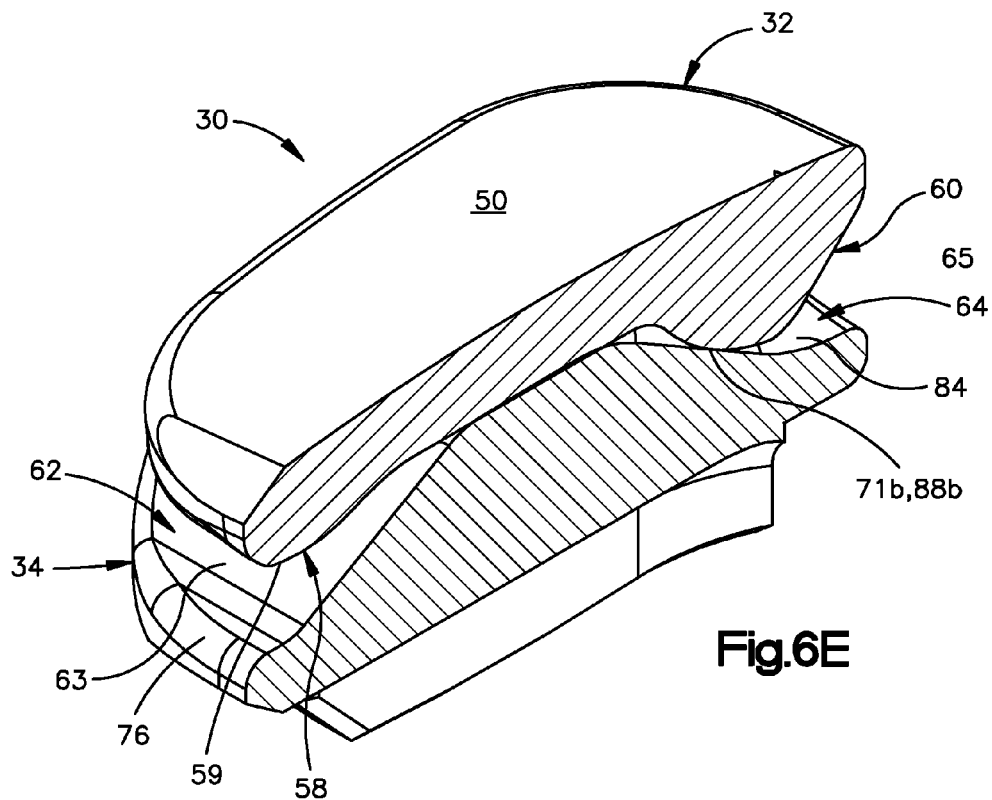
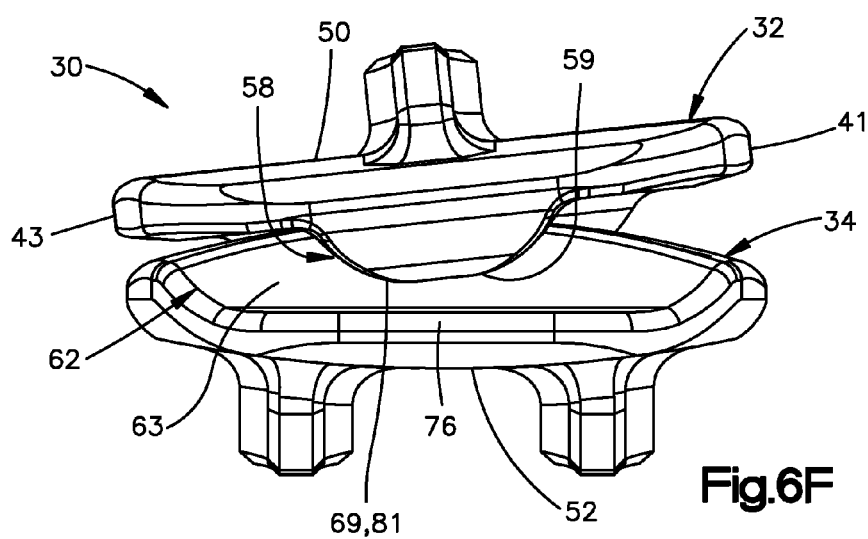

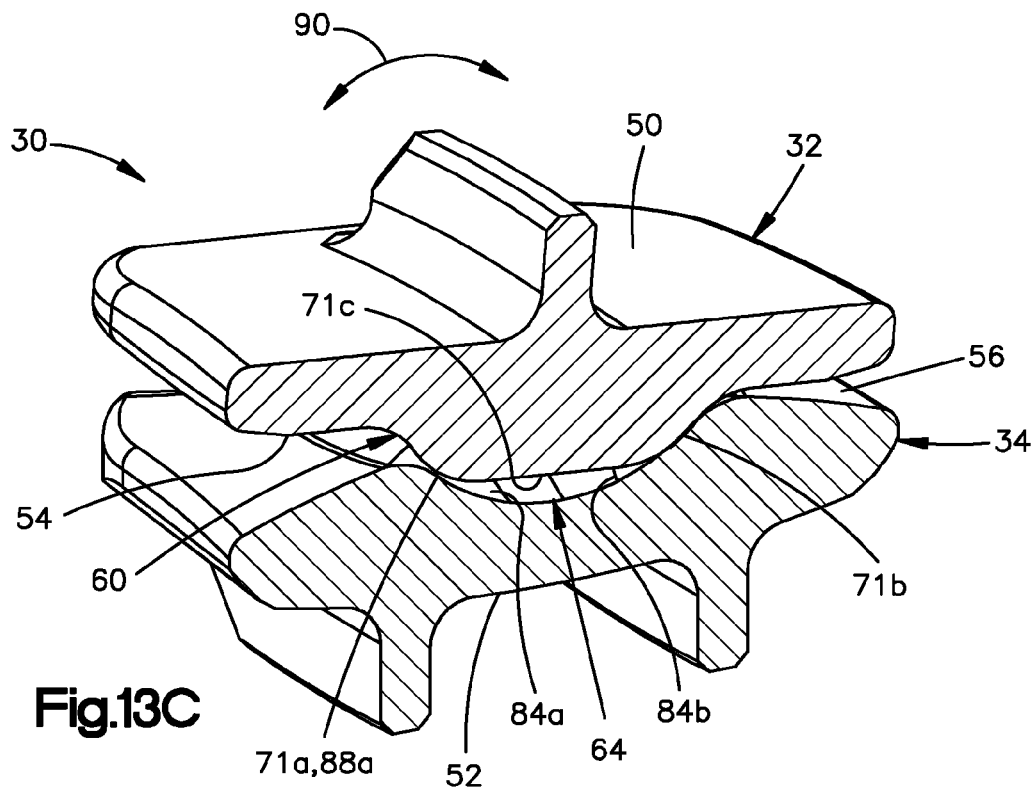
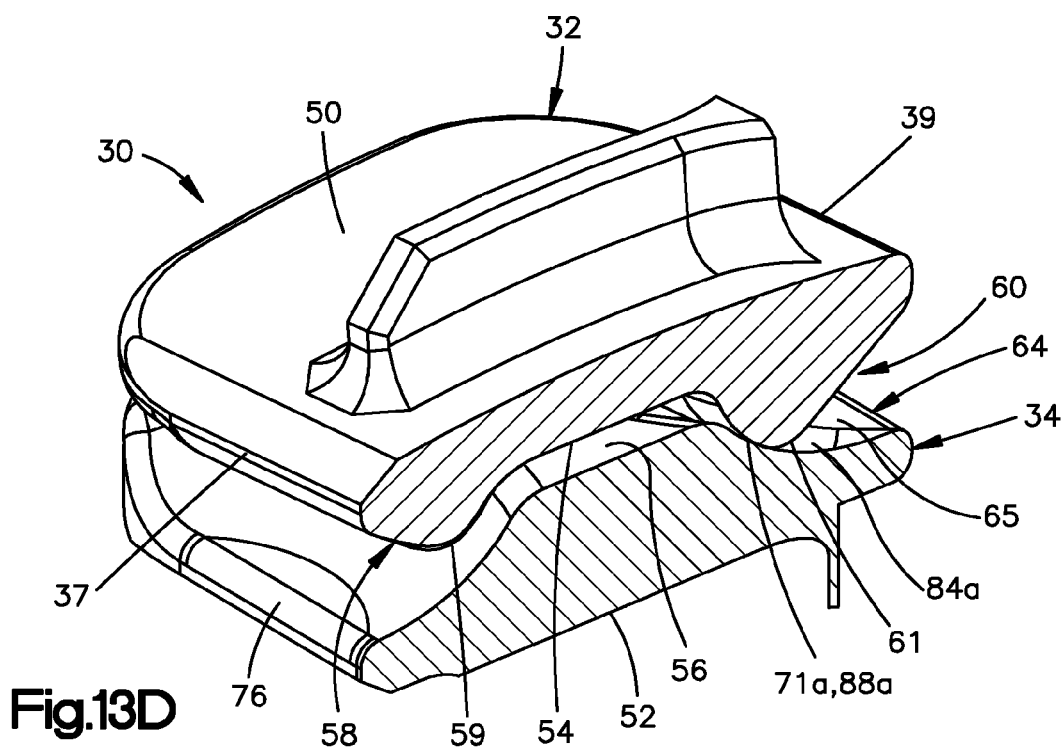

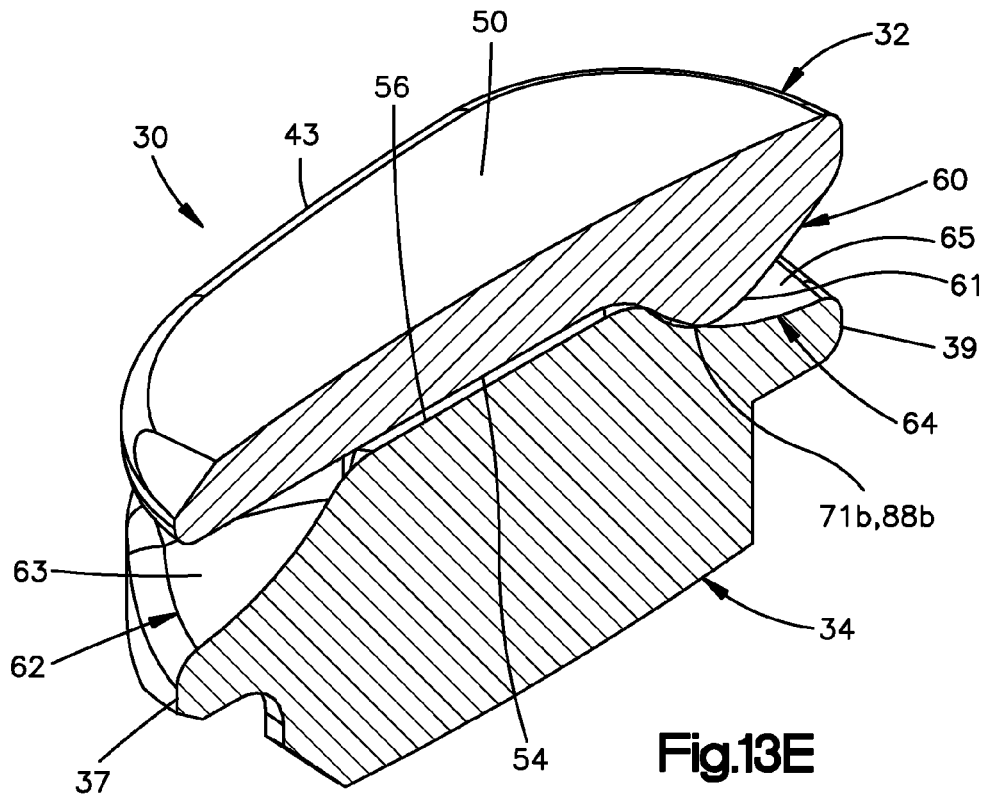
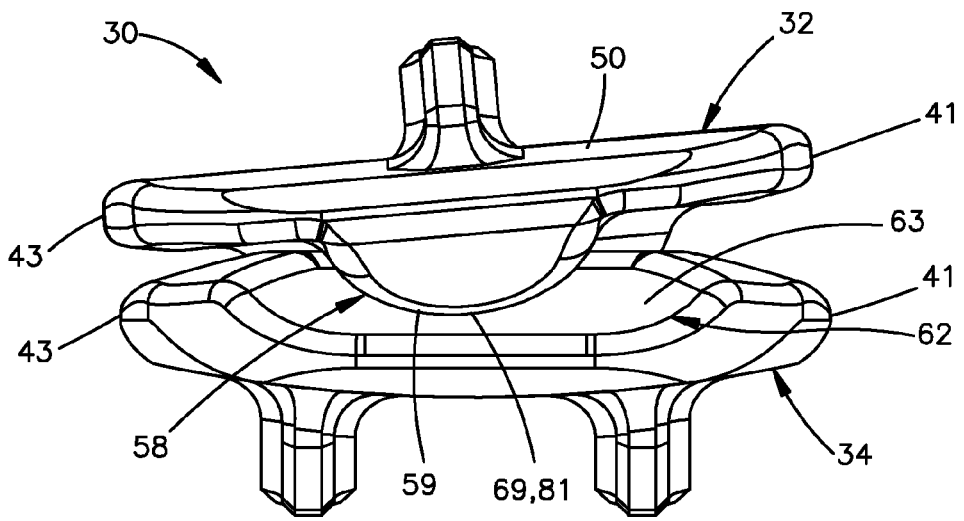

ARTICULATING INTERVERTEBRAL IMPLANT

BACKGROUND

The human spine includes a plurality of vertebra that are spaced from each other so as to define an intervertebral space. For instance, referring to FIG. 1A, intervertebral spinal discs are typically disposed in an intervertebral space 24 defined between a superior vertebra 22a and an inferior vertebra 22b that is adjacent the superior vertebra 22a in the human spine 20. Each healthy intervertebral spinal disc forms a cartilaginous joint that allows for slight movement of the superior vertebra 22a relative to the inferior vertebra 22b, and acts as a ligament to hold the vertebrae 22a and 22b together.

Normal anatomical motion of the spine is partially defined by various soft tissue, including muscles, tendons, and ligaments along with the anatomical structure of the superior vertebra 22a and the inferior vertebra 22b. For instance, when a person moves his or her body, muscles exert pressure on the vertebrae 22a and 22b, thereby causing them to move. The spine 20 defines a central axis 9 that corresponds to the intersection of the medial-lateral and the anterior-posterior planes. In the cervical region, the superior vertebra 22a typically rotates about a medial-lateral axis 3 of the inferior vertebra 22b, an oblique axis 2 that is angularly offset and non-perpendicular with respect to the medial-lateral axis 1, or about both axes 1 and 2.

When a person bends his or her forward, such as to look at their toes, or backwards, such as to look at the sky, the spine 20 undergoes a motion known as flexion and extension, respectively. When the cervical region of the spine undergoes pure flexion and pure extension, the superior vertebra 22a rotates about the medial-lateral axis 3, and thus moves in the sagittal plane.

When a person bends his or her head from side-to-side, the cervical region of the spine experiences a motion known as lateral bending. When a person turns his or her head to the left or right about the central axis 9, the cervical region of the spine experiences a motion known as axial rotation. Each of the vertebrae 22a and 22b defines a pair of facets that engage each other so as to define a respective pair of facet joints. Lateral bending of the cervical region of the spine (for instance at the lower cervical motion segments C3-C7) causes the superior vertebra 22a to move relative to the inferior vertebra 22b. The geometry of the spine 20 in the cervical region dictates that the superior vertebra 22a move relative to the inferior vertebra along a direction that is substantially planar with respect to the facet joints, so that the facets do not interfere with each other during normal anatomical movement. Thus, a mode of motion of the superior vertebra 22a other than flexion-extension causes the superior vertebra 22a at the lower cervical motion segments to undergo a combined motion with respect to the inferior vertebra 22b. For instance, axial rotation of the superior vertebra 22a relative to the inferior vertebra 22b also induces lateral bending of the superior vertebra 22a relative to the inferior vertebra 22b. Similarly, lateral bending of the superior vertebra 22a relative to the inferior vertebra 22b also induces axial rotation of the superior vertebra 22a relative to the inferior vertebra 22b.

Over time, general wear and tear can cause spinal discs to can become damaged or dislocated giving rise to a problem commonly referred to as a "slipped disc". In the past, damaged discs were treated by removing the disc and packing the space with bone chips to promote fusion of the adjacent vertebral body. However, this method resulted in a loss of mobility in the patient's lower back. More recent solutions for treating damaged discs include the replacement of the damaged disc with an articulating prosthetic disc implant that permits relative motion between the adjacent vertebral body. Because surgical procedures that replace spinal discs with prosthetic implants in the cervical region of the spine typically access the intervertebral space along an anterior-posterior direction, the surgeon often times removes the anterior longitudinal ligament in order to gain access to the intervertebral space. In some cases, the surgeon may also remove the posterior longitudinal ligament, for instance if it is desired to analyze possible impingements on the spinal cord. Removal of these ligaments eliminates one or more sources that promote normal anatomical motion between adjacent vertebrae.

SUMMARY

In accordance with one embodiment, an intervertebral implant is configured to be inserted along an insertion direction into an intervertebral space disposed between first and second vertebrae. The intervertebral implant includes a first endplate having a front end and a rear end spaced from the front end along the direction of insertion into the intervertebral space. The first endplate includes a first endplate body, a first articulation member that is supported by the first endplate body at a location proximate to the front end, and at least one second articulation member that is supported by the first endplate body at a location proximate to the rear end. The intervertebral implant further includes a second endplate having a front end and a rear end spaced from the front end along the direction of insertion into the intervertebral space. The second endplate includes a second endplate body, a third articulation member supported by the second endplate body at a location proximate to the front end of the second endplate, and a fourth articulation member supported by the second endplate body at a location proximate to the rear end of the second endplate. During operation, the first and second articulation members can ride along the third and fourth articulation members, respectively, such that rotation of the first endplate about a first axis of rotation that is substantially perpendicular to the insertion direction induces rotation of the first endplate about a second axis of rotation that is substantially perpendicular to the first axis of rotation.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating various embodiments, drawings are shown. It should be understood, however, that the present disclosure is not limited to the precise arrangement, structures, features, embodiments, aspects, and instrumentalities shown, and that the arrangements, structures, features, embodiments, aspects and instrumentalities shown may be used singularly or in combination with other arrangements, structures, features, aspects, embodiments and instrumentalities. In the drawings:

FIG. 1A is a schematic representation of a cervical region of a human spine, illustrating various modes of movement;

FIG. 1B is a perspective view of an intervertebral implant constructed in accordance with one embodiment, shown inserted into an intervertebral space that is defined between a superior cervical vertebra and an inferior cervical vertebra;

FIG. 2C is a top perspective view of the lower endplate of the intervertebral implant illustrated in FIG. 1C, including respective third and fourth articulation members;

FIG. 2D is another top perspective view of the lower endplate of the intervertebral implant illustrated in FIG. 1C;

FIG. 5C is a cross-sectional view of the intervertebral implant illustrated in FIG. 5A, taken at line 5C-5C;

FIG. 5D is a cross-sectional view of the intervertebral implant illustrated in FIG. 5A, taken at line 5D-5D;

FIG. 6E is a cross-sectional view of the intervertebral implant illustrated in FIG. 6A, taken at line 6E-6E;

FIG. 6F is a rear elevation view of the intervertebral implant illustrated in FIG. 6A;

FIG. 13C is a cross-sectional view of the intervertebral implant illustrated in FIG. 13A, taken at line 13C-13C;

FIG. 13D is a cross-sectional view of the intervertebral implant illustrated in FIG. 13A, taken at line 13D-13D;

FIG. 13E is a cross-sectional view of the intervertebral implant illustrated in FIG. 13A, taken at line 13E-13E;

FIG. 13F is a front elevation view of the intervertebral implant illustrated in FIG. 13A;

DETAILED DESCRIPTION

Figure 1C:
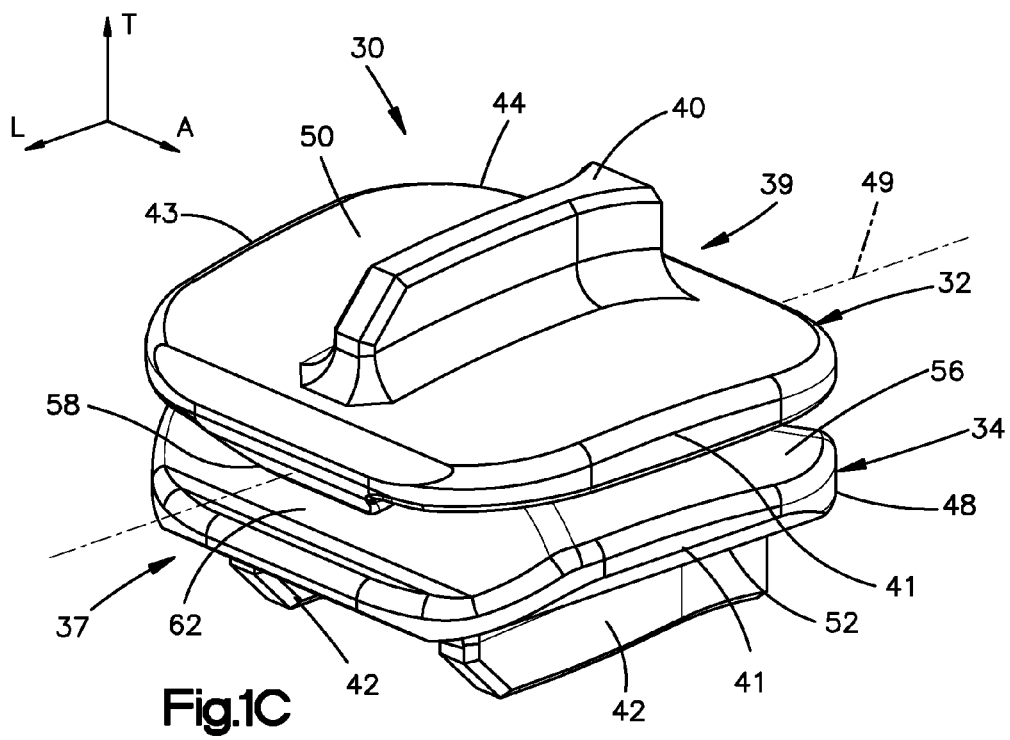
FIG. 1C is a top perspective view of an intervertebral implant illustrated in FIG. 1B, including an upper endplate and a lower endplate.

Certain terminology is used in the following description for convenience only and is not limiting. The words "right", "left", "lower", "upper", "bottom", and "top" designate directions in the drawings to which reference is made. The words "inwardly" and "outwardly" refer to directions toward and away from, respectively, the geometric center of the bone fixation element, instruments and designated parts thereof. The words, "anterior", "posterior", "superior", "inferior", "medial", "lateral" and related words and/or phrases designate preferred positions and orientations in the human body to which reference is made and are not meant to be limiting. The terminology includes the above-listed words, derivatives thereof and words of similar import.

Referring to FIGS. 1A-B, a spine 20 includes pair of adjacent vertebral bodies 22, that include a superior vertebral body 22a and an inferior vertebral body 22b. The spine 20 further defines an intervertebral space 24 disposed between the superior vertebral body 22a and the inferior vertebral body 22b. As illustrated, the intervertebral space 24 is illustrated after a discectomy, whereby the disc material has been removed to prepare the intervertebral space 24 to receive an implant, such as an intervertebral implant 30. Thus, the intervertebral implant 30 is configured to be inserted into the intervertebral space 24, and achieve improved stability between the vertebral bodies 22a-b (for fusion or non-fusion procedures). The intervertebral space 24 can be disposed anywhere along the spine, but is disposed in the cervical region of the spine in accordance with one embodiment.

The intervertebral implant 30 and various components of the implant are described herein extending horizontally along a first or longitudinal direction "L" and a second or lateral direction "A", and vertically along a third or transverse direction "T". Thus, the longitudinal direction L is substantially perpendicular to the both the lateral direction A and the transverse direction T, the longitudinal direction A is substantially perpendicular to the both the longitudinal direction L and the transverse direction T, and the transverse direction T is substantially perpendicular to the both the longitudinal direction L and the lateral direction A. Unless otherwise specified herein, the terms "lateral," "longitudinal," and "transverse" are used to describe the orthogonal directional components of various components. It should be appreciated that while the longitudinal direction L and the lateral direction A are illustrated as extending along a horizontal plane, and that the transverse direction T is illustrated as extending along a vertical plane, the planes that encompass the various directions may differ during use. Accordingly, the directional terms "vertical" and "horizontal" are used to describe the intervertebral implant 30 and its components as illustrated merely for the purposes of clarity and illustration.

In the illustrated embodiment, the longitudinal direction L extends in an anterior-posterior direction, and is thus substantially parallel to a direction of insertion along which the intervertebral implant 30 is inserted into the intervertebral space 24. The lateral direction A extends along a medial-lateral direction, and the transverse direction T extends in a caudal-cranial direction. It should be appreciated, however, that the various directions defined by the intervertebral implant 30 could alternatively be oriented at any desirable angle between 0° and 180° with respect to the medial-lateral and anterior-posterior directions and the caudal-cranial direction.

Figure 1D:
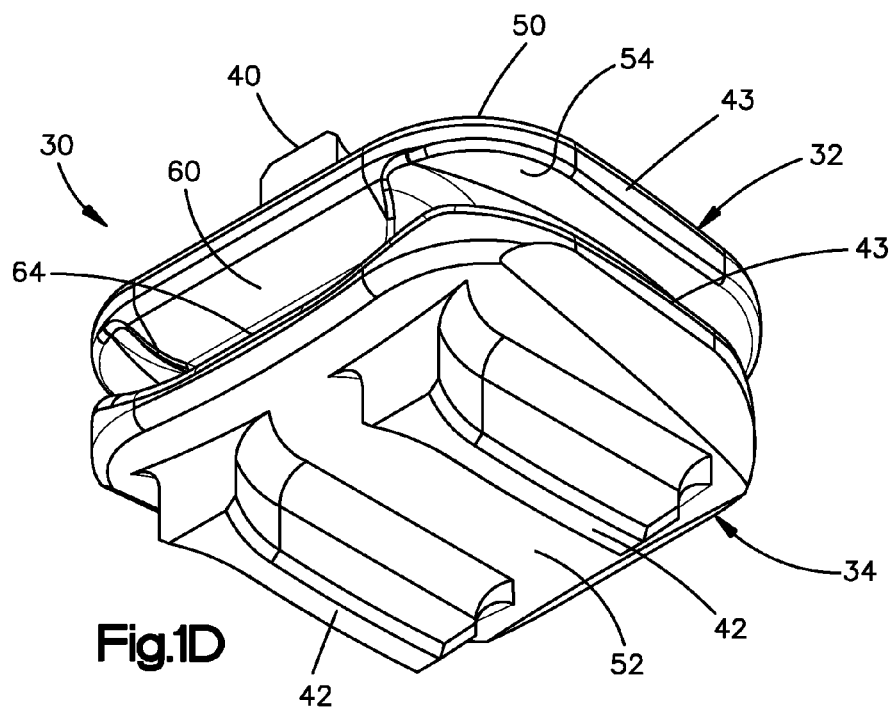
FIG. 1D is a bottom perspective view of the intervertebral implant illustrated in FIG. 1C.

Referring now to FIGS. 1C-D, the intervertebral implant 30 generally includes a first, or upper, endplate 32 and a second, or lower, endplate 34 that is spaced from the first endplate 32 along the transverse direction T. The first and second endplates 32 and 34, and components thereof, can be formed from a variety of biocompatible materials, such as cobalt chromium molybdenum (CoCrMo) with or without a porous plasma-sprayed titanium coating, titanium, stainless steel, ceramics, diamond, or polymers such as polyetheretherketone (PEEK).

The intervertebral implant 30, and thus each of the first and second endplates 32 and 34, defines a front end 37 and a rear end 39 that is rearwardly spaced from the front end 37 along the longitudinal direction L when the intervertebral implant 30 is in a neutral position as illustrated in FIGS. 3A-F. The front end 37 defines a leading end and the rear end 39 defines a trailing end with respect to the direction of insertion of the intervertebral implant 30 into the intervertebral space. Thus, the intervertebral implant 30 is configured to be inserted into the intervertebral space 24 along a forward longitudinal direction that extends from the rear end 39 toward the front end 37. Thus, the terms "forward" and "rearward" and derivatives thereof, as used herein with respect to the components of the intervertebral implant 30, are used reference to the front and rear ends 37 and 39 of the intervertebral implant 30. The intervertebral implant 30, and thus each of the first and second endplates 32 and 34, further defines first and second sides 41 and 43 that extend between the front end rear ends 37 and 39, are spaced along the lateral direction A.

The first and second endplates 32 and 34 define respective first and second endplate bodies 44 and 48 that define outer transverse bone-contacting surfaces 50 and 52 of the first and second endplates 32 and 34, respectively. For instance, the outer surface 50 of the first endplate body 44 can be upwardly-facing, and the outer surface 52 of the second endplate body 48 can be downwardly-facing. The outer surfaces 50 and 52 can be smooth or textured to facilitate fusion with the associated vertebral bodies as desired. The first and second endplates 32 and 34 further define respective inner transverse surfaces 54 and 56 that are spaced from the outer surfaces 50 and 52 along the transverse direction T. The inner surfaces 54 and 56 face each other when the first endplate 32 is operably coupled to the second endplate 34.

The first endplate 32 extends along a central longitudinal axis 49 that extends between the front end rear ends 37 and 39 of the first endplate 32, a central lateral axis 51 that extends between the first and second sides 41 and 43 of the first endplate 32, and a central transverse axis 53 that extends between the outer and inner surfaces 50 and 54 of the first endplate 32. When the intervertebral implant 30 is in a neutral position as illustrated in FIGS. 3A-F, the central longitudinal axis 49 extends along the longitudinal direction L, the central lateral axis 51 extends along the lateral direction A, and the central transverse axis 53 extends along the transverse direction T. The second endplate 34 similarly extends along a central longitudinal axis 55 that extends between the front end rear ends 37 and 39 of the second endplate 34, a central lateral axis 57 that extends between the first and second sides 41 and 34 of the second endplate 34, and a central transverse axis 53 that extends between the outer and inner surfaces 52 and 56 of the second endplate 34. When the intervertebral implant 30 is in the neutral position, the central longitudinal axis 55 extends along the longitudinal direction L, the central lateral axis 57 extends along the lateral direction A, and the central transverse axis 73 extends along the transverse direction T.

Thus, when the intervertebral implant 30 is in the neutral position, the respective central longitudinal axes 49 and 55, the respective central lateral axes 51 and 57, and the respective transverse axes 53 and 73 can be aligned with each other. One or more of the respective central longitudinal axes 49 and 55, the respective central lateral axes 51 and 57, and the respective transverse axes 53 and 73 can be offset with respect to the other when the intervertebral implant 30 is articulated out of the neutral position. It should be appreciated that when the intervertebral implant 30 is implanted in the intervertebral space and is in the neutral position, the central longitudinal axes 49 and 55 extend in the anterior-posterior direction, the central lateral axes 51 and 57 extend in the medial-lateral direction, and the respective transverse axes 53 and 73 extend in the caudal-cranial direction.

The intervertebral implant 30 can define a width extending along the lateral direction A between the opposed sides 41 and 43 that can be between approximately 15-19 mm, a length extending along the longitudinal dimension L between the front end rear ends 37 and 39 that can be approximately 12-16 mm, and a height extending between the outer surfaces 50 and 52 along the transverse direction T that can be approximately 5-9 mm. Thus, the intervertebral implant 30 is suitable for implantation in an intervertebral space in the cervical region of the spine, which is characterized by the need for precision because of the relatively small dimensions of cervical intervertebral spaces. While the intervertebral implant 30 is configured to be inserted into the cervical region of the spine that defines the intervertebral space 24, it should be appreciated that the intervertebral implant 30 can alternatively be dimensioned so as to be inserted into an intervertebral space in a different spinal region, for instance the lumbar region. The intervertebral implant 30 configured for implantation into the lumbar region can have a width between approximately 27 and 30 mm, a length of approximately 34-39 mm, and a height of approximately 10-14 mm. Thus, it is to be understood that unless otherwise indicated, the intervertebral implant 30 can be constructed with any dimensions desirable for implantation of any intervertebral space along the spine, and is not limited to the cervical and lumbar regions.

The first and second endplates 32 and 34 can further include respective keels 40 and 42 that extend out from the respective endplate bodies 44 and 48, for instance from the respective bone-contacting surfaces 36 and 38, along the transverse direction T. In accordance with the illustrated embodiment, the first endplate 32 has a single keel 40 that extends out from the bone-contacting surface 36, and the second endplate 34 includes a pair of keels 42 that extends out from the bone-contacting surface 38. The keel 40 can be elongate along the longitudinal direction L, and can further be disposed centrally on the bone-contacting surface 36 with respect to the lateral direction A. The keels 42 can also be elongate along the longitudinal direction L, and can be disposed on the bone-contacting surface 38 at a location such that a midline, that is disposed between the keels 42 and equidistantly spaced from the keels 42, is disposed centrally on the bone-contacting surface 38 with respect to the lateral direction A. In accordance with the illustrated embodiment, the keels 40 and 42 are configured to be received in respective openings that can be formed in the respective superior and inferior vertebral bodies. Of course, it should be appreciated that either or both of the endplates 32 and 34 can include any number of keels as desired, such as at least one keel, located and oriented as desired. For instance, the end plates 32 and 34 can include the same number of keels, the first endplate 32 can include more keels than the second endplate 34, or the first endplate 32 can include fewer keels than the second endplate 34. Alternatively, either or both of the endplates 32 and 34 can be devoid of keels as desired.

In accordance with the illustrated embodiment, in order to position the intervertebral implant 30 into the intervertebral disc space 14, a cut is made in the inferior as well as in the superior vertebral bodies 12a-b to define slots that extend therein that conform generally to the size and shape of the keels 40 and 42. The slots can be provided using any method and apparatus as desired, such as a chisel or a drilling/milling system of the type disclosed in U.S. patent application Ser.

No. 12/375,710, filed Jan. 30, 2009, the disclosure of which is hereby incorporated by reference as if set forth in its entirety herein.

Figure 1E:
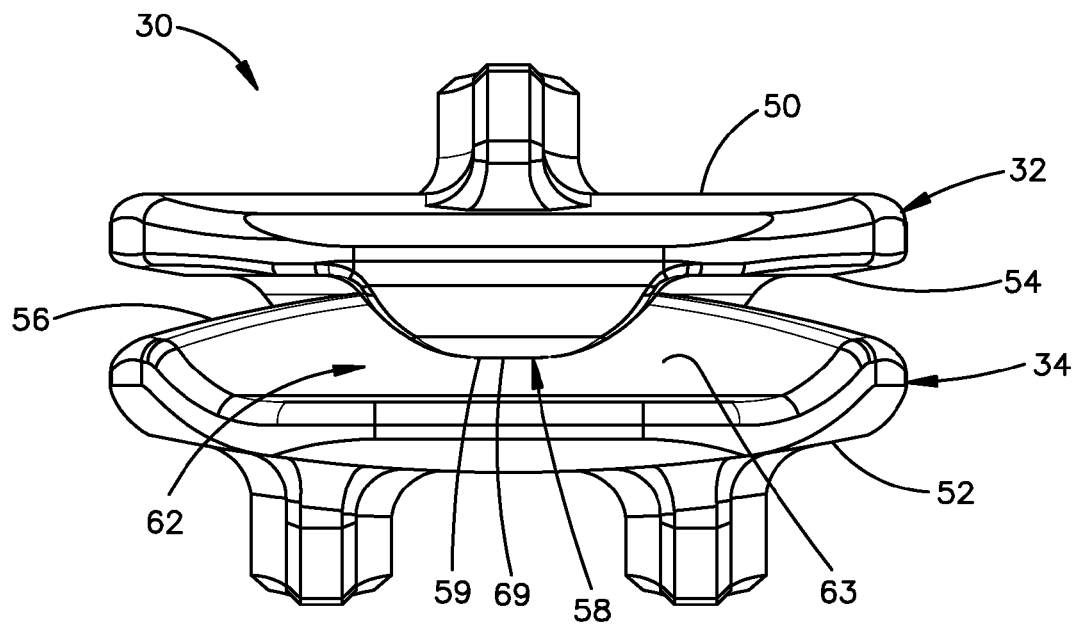
FIG. 1E is a front elevation view of the intervertebral implant illustrated in FIG. 1C.
Figure 1F:
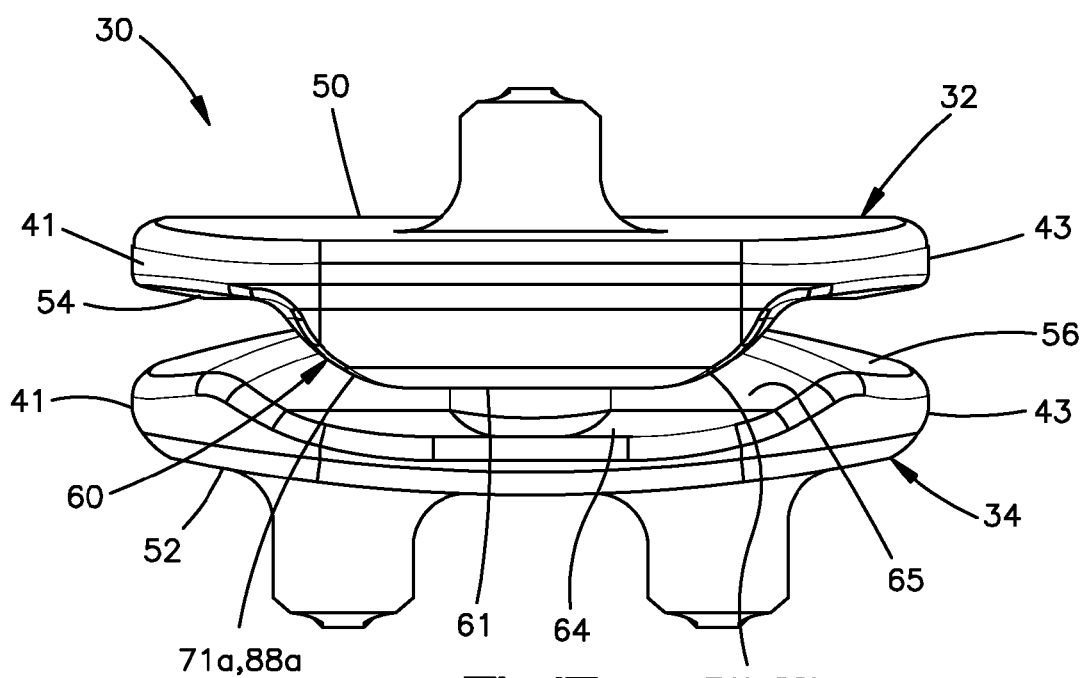
FIG. 1F is a rear elevation view of the intervertebral implant illustrated in FIG. 1C.

Referring also to FIGS. 1E-F, the first endplate 32 includes a first or front articulation member 58 disposed proximate to the front end 37 of the first endplate 32, and a second or rear articulation member 60 that is disposed proximate to the rear end 39 of the first endplate 32 and is thus rearwardly spaced from the first articulation member 58 along the longitudinal direction L. The first and second articulation members 58 and 60 are each carried by the first endplate body 44, and define protrusions that project out from the first endplate body 44, for instance from the inner surface 54, along the transverse direction T. In particular, the first and second articulation members 58 and 60 project down from the inner surface 54 toward the second endplate 34, and in particular toward the inner surface 56 of the second endplate body 48. The second endplate 34 includes a third or front articulation member 62 and a fourth or rear articulation member 64 that is rearwardly spaced from the third articulation member 62 along the longitudinal direction L. The third and fourth articulation members 62 and 64 are each carried by the second endplate body 48, and are defined by the inner surface 56. The first and second endplates 32 and 34 operably engage each other such that the first and third articulation members 58 and 62 contact each other, and the second and fourth articulation members 60 and 64 contact each other. In accordance with the illustrated embodiment, the first and second endplates 32 and 34 contact each other only at the interfaces between the first and third articulation members 58 and 62, and the second and fourth articulation members 60 and 64.

During operation, the first articulation member 58 is configured to abut and ride along the third articulation member 62, and the second actuation member 60 is configured to abut and ride along the fourth articulation member 64. Thus, the first and second endplates 32 and 34 are configured to articulate relative to each other about at least a first contact interface and a second contact interface, the contact interfaces defining at least one location of contact between the first and second endplates 32 and 34, whereby the first contact interface is disposed at an anterior end of the implant 30, and thus on one side of a central lateral axis that extends in the lateral direction A, and the second contact interface is disposed at a posterior end of the implant 30, and thus on an opposite side of the central lateral axis with respect to the first contact interface. In accordance with the illustrated embodiment, the first articulation member 58 defines a corresponding first articulation surface 59 that is supported by (and extends from) the first endplate body 44, and the third articulation member 62 defines a complementary third articulation surface 63 supported by the second endplate body 48, such that the first articulation surface rides along the third articulation surface 63 during operation. As will be described in more detail below, the first articulation surface 59 defines a contact location 69 that contacts the third articulation surface 63, and the first articulation member 58 contacts the third articulation member 62 only at the contact location 69.

Similarly, the second articulation member 60 defines a second articulation surface 61 that is supported by (and extends from) the first endplate body 44, and the fourth articulation member 64 defines a complementary fourth articulation surface 65 that is supported by the second endplate body 48, such that the second articulation surface 61 rides along the fourth articulation surface 65 during operation. As will be described in more detail below, the second articulation surface 61 defines first and second rear contact locations 71a and 71b that are supported by the first endplate body 44 at a location proximate to the rear end 39 of the first endplate 32. The first and second contact locations 71a and 71b are spaced from each other along the lateral direction A and contact the third articulation surface 63. The first contact location 71a is disposed closer to the first side wall 41 than the second side wall 43, and the second contact location 71b is disposed closer to the second side wall 43 than the first side wall 41. The second articulation member 60 contacts the fourth articulation member 64 only at the first and second contact locations 71a and 71b.

Figure 2A:
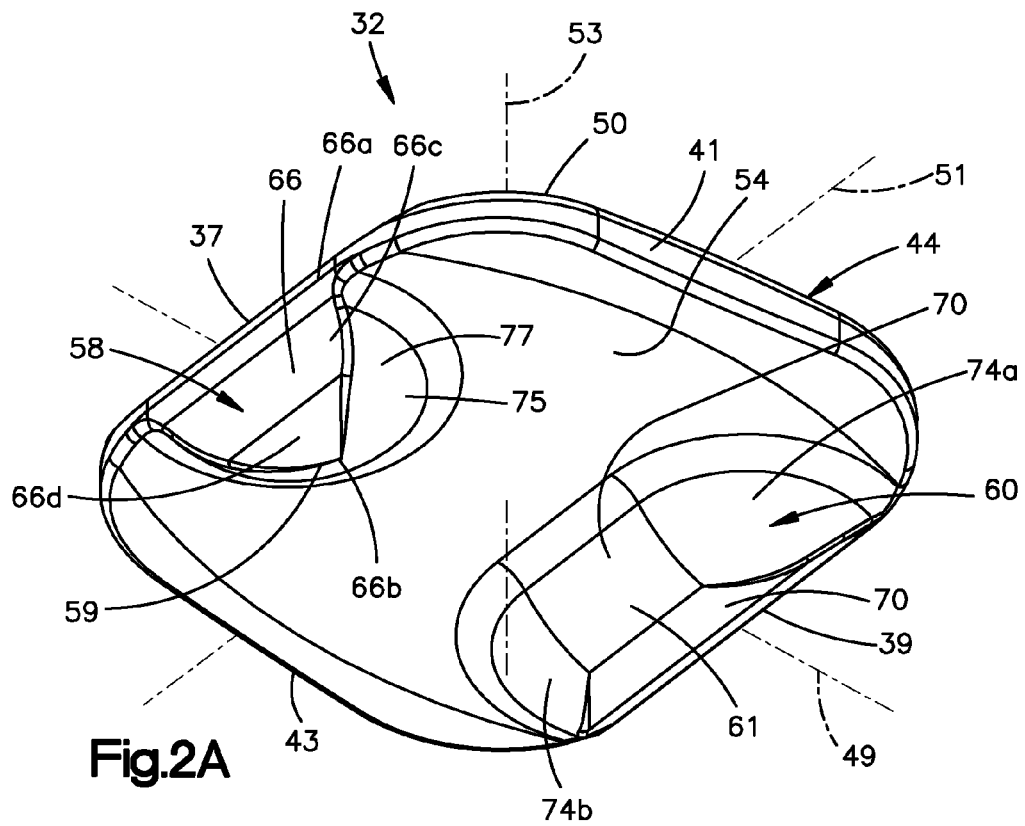
FIG. 2A is a bottom perspective view of the upper endplate of the intervertebral implant illustrated in FIG. 1C, including respective first and second articulation members.
Figure 2B:
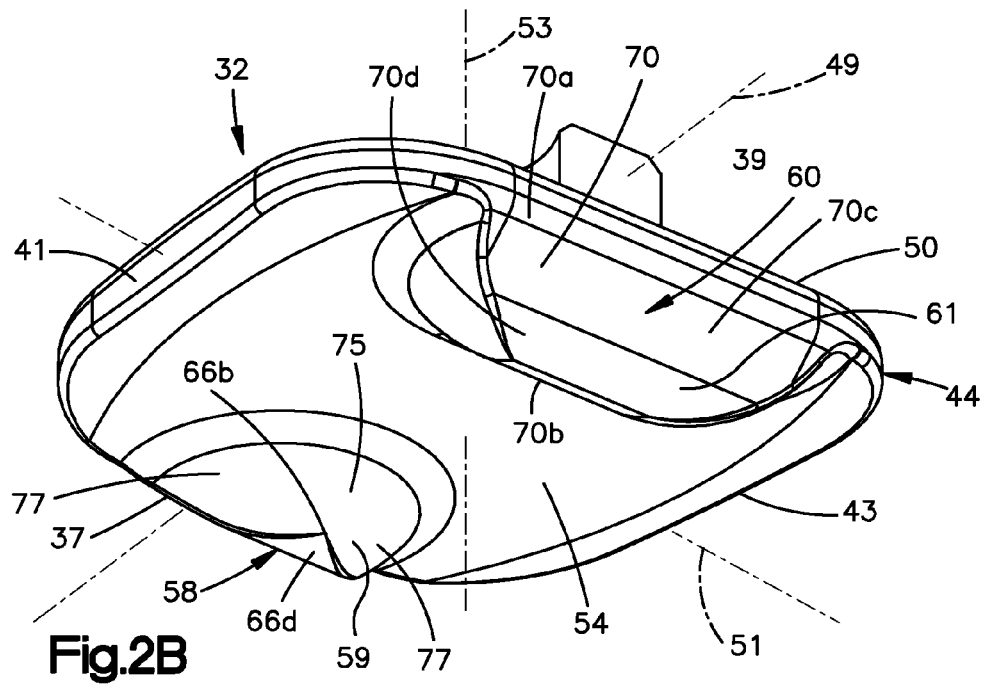
FIG. 2B is another bottom perspective view of the upper endplate of the intervertebral implant illustrated in FIG. 1C.

Referring now to FIGS. 2A-B, the first articulation member 58 extends from the first endplate body 44, and can be integral and monolithic with the first endplate body 44 or discreetly attached to the endplate body as desired. In accordance with the illustrated embodiment, the first articulation member 58 defines an outer or front surface 66 that extends from the first endplate body 44, and in particular from the inner surface 54. The front surface 66 can be triangular or v-shaped as illustrated as viewed along a direction from the front end 37 toward the rear end 39, or can define any suitable alternative geometry as desired. The front surface 66 defines a base 66a that extends from the first endplate body 44 and an apex 66b that is spaced from the base 66a along both the longitudinal L and transverse T directions. The base 66a can extend from the inner surface 54 of the first endplate body 44, for instance from the front end 37. The apex 66b is spaced rearward and downward from the base 66a. The front surface 66 defines a proximal region 66c proximate to the base 66a, and a distal region 66d proximate to the apex 66b, such that the proximal region 66c is disposed between the distal region 66d and the base 66a, and the distal region 66d is disposed between the proximal region 66c and the apex 66b. In accordance with the illustrated embodiment, the proximal region 66c is sloped substantially linearly between the base 66a and the distal region 66d, and the distal region 66d is curved between the proximal region 66c and the apex 66b, though it should be appreciated that the proximal and distal regions 66c and 66d can assume any alternative geometric configuration as desired. In accordance with the illustrated embodiment, the proximal region is sloped substantially linearly rearwardly along the longitudinal direction L as it extends out from the base 66a along the transverse direction T. The proximal region 66c further extends substantially straight along the lateral direction A, such that the proximal region 66c is substantially planar. The distal region 66d can likewise extend substantially straight along the lateral direction A, and can be curved as it extends rearwardly from the proximal region 66c to the apex 66b.

The first articulation member 58 further defines an inner or rear surface 75 that extends between the outer perimeter of the front surface 66 and the first endplate body 44. The rear surface 75 can be curved as it extends along the lateral direction A, and can further be curved as it extends along the longitudinal direction L. The curvatures along the lateral direction A and the longitudinal direction L can be the same or different from each other. The first articulation member 58 further defines a pair of opposed side surfaces 77 that are inwardly recessed with respect to the first and second sides 41 and 43 of the first endplate 32, and can be equidistantly spaced with respect to the corresponding first and second sides 41 and 43. The opposed side surfaces 77 extend between the front surface 68, the rear surface 75, and the first endplate body 44, for instance at the inner surface 54. The side surfaces 77 can be coextensive with the rear surface 75, and can be curved as it extends along the lateral direction A and the longitudinal direction L. In accordance with the illustrated embodiment, the rear and side surfaces 75 and 77 are convex and define a circular interface at the inner surface 54 of the first endplate body 44.

The outer perimeter of the first articulation member 58, for instance at the rear surface 75, defines the first articulation surface 59, and the contact location 69 is defined on the first articulation surface 59. Because the first articulation surface 59 is disposed proximate to the front end 37 of the first endplate 32, the first articulation surface 59 can also be referred to as a front articulation surface. Furthermore, because the first articulation surface 59 is defined by the first articulation member 58, and because the first articulation member 58 is supported by the first endplate body 44, it can be said that the first articulation surface 59 is supported by the first endplate body 44. In accordance with the illustrated embodiment, the contact location 69 is aligned with the central longitudinal axis 49 of the first endplate 32, though it should be appreciated that the contact location 69 can be disposed anywhere along the first articulation surface. It should be further appreciated that while the first articulation member 58 is illustrated as defining only a single contact location 69, the first articulation member 58 can define any number of contact locations, such as at least one contact location, that contact and ride along the third articulation surface 63 as desired. The contact location 69 can further be aligned with the central longitudinal axis 55 of the second endplate 34, for instance when the intervertebral implant 30 is in a neutral position as illustrated in FIGS. 3A-F. As described in more detail below, the contact location 69 can vary in position along the first articulation surface 59 during operation. For instance, the contact location 69 can move along the rear surface 75 in the lateral direction A as the first endplate 32 rotates relative to the second endplate about an axis of rotation that extends along the longitudinal direction L. Further because the rear surface 75 is curved as it extends both along the longitudinal direction L and the lateral direction A, the contact location 69 defines a point contact along the third articulation surface 63.

With continuing reference to FIGS. 2A-B, the second articulation member 60 extends from the first endplate body 44, and can be integral and monolithic with the first endplate body 44 or discreetly attached to the first endplate body 44 as desired. The second articulation member 60 is rearwardly spaced from the first articulation member 58 along the longitudinal direction L, such that the first and second articulation members 58 and 60 are separated by the first endplate body 44, and in particular separated by the inner surface 54. The inner surface 54 can be substantially planar along a plane defined by the longitudinal and lateral directions A and L, and can be beveled at the sides 41 and 43 or can assume any suitable alternative geometry as desired. For instance, the inner surface 54 can be curved along either or both of the longitudinal direction L and the lateral direction A.

In accordance with the illustrated embodiment, the second articulation member 60 defines an outer or rear surface 70 that extends from the first endplate body 44, and in particular from the inner surface 54. The rear surface 70 can define any suitable alternative geometry as desired, and defines a base 70a that extends from the first endplate body 44 and an apex 70b that is spaced from the base 70a along both the longitudinal L and transverse T directions. For instance, the apex 70b is spaced forward and downward from the base 70a. In accordance with the illustrated embodiment, the base 70a extends from the inner surface 54 of the first endplate body 44, and in particular from the rear end 39. The rear surface 70 defines a proximal region 70c proximate to the base 70a, and a distal region 70d proximate to the apex 70b, such that the proximal region 70c is disposed between the distal region 70d and the base 70a, and the distal region 70d is disposed between the proximal region 70c and the apex 70b. In accordance with the illustrated embodiment, the proximal region 70c is sloped substantially linearly between the base 70a and the distal region 70d, and the distal region 70d is curved between the proximal region 70c and the apex 70b, though it should be appreciated that the proximal and distal regions 70c and 70d can assume any alternative geometric configuration as desired. In accordance with the illustrated embodiment, the proximal region 70c is sloped substantially linearly forwardly along the longitudinal direction L as it extends out from the base 70a along the transverse direction T. The proximal region 70c further extends substantially straight along the lateral direction A, such that the proximal region 70c is substantially planar. The distal region 70d can likewise extend substantially straight along the lateral direction A, and can be curved as it extends forward from the proximal region 70c to the apex 70b.

The second articulation member 60 further defines an inner or front surface 72 that extends between the outer perimeter of the rear surface 70 and the first endplate body 44. The front surface 72 can extend substantially straight as it extends along the lateral direction A, and can further be curved as it extends along the longitudinal direction L between the first endplate body 44 and the rear surface 70. The second articulation member 60 further defines first and second opposed side surfaces 74a-b that extend between the front surface 68, the rear surface 75, and the first endplate body 44, for instance at the inner surface 54. Each of the side surfaces 74a and 74b can be curved as it extends along the lateral direction A and can further be curved as it extends along the longitudinal direction L. In accordance with the illustrated embodiment, the side surfaces 74a and 74b are symmetrical to each other. The front and side surfaces 72 and 74a-b can convex as illustrated, or alternatively shaped as desired.

The outer perimeter of the second articulation member 60 defines the second articulation surface 61. Because the second articulation surface 61 is defined by the second articulation member 60, and because the second articulation member 60 is supported by the first endplate body 44, it can be said that the second articulation surface 61 is supported by the first endplate body 44. The second articulation surface 61, for instance at the side surfaces 74a and 74b, defines the first and second contact locations 71a and 71b, respectively, of the second articulation member 60. The first and second contact locations 71a and 71b are separated from each other along the lateral direction A by the rear surface 70 and the front surface 72, such that the second articulation surface 61 does not contact the fourth articulation surface 65 at locations located laterally between the first and second contact locations 71a and 71b. Thus, the second articulation member 60 defines an intermediate region 71c that extends along the lateral direction A between the first and second contact locations 71a and 71b. In accordance with the illustrated embodiment, second contact locations 71a and 71b are equidistantly spaced from the central longitudinal axis 49 of the first endplate 32. The second contact locations 71a-b can further be equidistantly spaced from the central longitudinal axis 55 of the second endplate 34, for instance when the intervertebral implant 30 is in the neutral position. Because the contact location 69 of the first articulation surface 59 can lie on the central longitudinal axis 49, it should be appreciated that the contact location 69 can be centrally disposed with respect to the first and second contact locations 71a and 71b along the lateral direction A. It should be appreciated that the contact location 69 of the first articulation member 58 defines a single front contact location, and the first and second contact locations 71*a* and 71*b* of the second articulation member 60 defines a pair of rear contact locations that are located both laterally outward and posterior with respect to the front contact location.

It should be appreciated that while the first and second contact locations 71*a* and 71*b* are defined by the same second articulation member 60, the first and second contact locations 71*a* and 71*b* can alternatively be defined by different articulation members that extend from the inner surface 54 as described above with respect to the second articulation member 60, such that at least the inner surface 54 can define the intermediate region 71*c*. Thus, at least one second articulation member 60 can define the second articulation surface 61, and at least one second articulation member 60 can define the first and second contact locations 71*a* and 71*b*. In this regard, it should be appreciated that the articulation surfaces described herein can be continuous as illustrated, or can alternatively be discontinuous or segmented as desired.

During operation of the intervertebral implant 30, the first and second contact locations 71*a* and 71*b* are configured to travel along the second articulation member 60, for instance along the first and second side surfaces 74*a* and 74*b*. Furthermore, because the side surfaces 74*a* and 74*b* are curved as they extend along both the longitudinal direction L and the lateral direction A, the contact locations 71*a* and 71*b* each defines a point contact along the fourth articulation surface 65. It should be further appreciated that while the second articulation member 60 is illustrated as defining a pair of contact locations 71*a* and 71*b*, the second articulation member 60 can define any number of contact locations, such as at least one contact location, that contact and ride along the fourth articulation surface 65 as desired. It should be further appreciated that while the first and second contact locations 71*a* and 71*b* are defined by the same second articulation member 60, the first and second contact locations 71*a* and 71*b* can alternatively be defined by different articulation members that extend from the inner surface 54 as described above with respect to the second articulation member 60.

While the first and second articulation members 58 and 60 have been described in accordance with the illustrated embodiment, it should be appreciated that the geometry of the first and second articulation members 58 and 60 can vary as desired, such that the first articulation member 58 defines at least one first articulation surface, and the second articulation member defines at least one second articulation surface that ride along the third and fourth articulation surfaces 63 and 65, respectively.

Referring now to FIGS. 2C-D, the third articulation member 62 extends from the second endplate body 48, and can be integral and monolithic with the second endplate body 48 or discreetly attached to the second endplate body 48 as desired. In accordance with the illustrated embodiment, the third articulation member 62 extends from the inner surface 56, and is recessed with respect to the inner surface 56 of the second endplate body 48. The third articulation member 62 defines the third articulation surface 63 and a stop member 76 that extends out from the third articulation surface 63. Because the third articulation surface 63 is defined by the third articulation member 62, and because the first articulation member 62 is supported by the second endplate body 48, it can be said that the third articulation surface 63 is supported by the second endplate body 48. The third articulation surface 63 can be substantially planar, though it should be appreciated that the third articulation surface 63 can define any suitable alternative geometry as desired. In accordance with the illustrated embodiment, the third articulation surface 63 extends between the sides 41 and 43 of the second endplate 34, and extends substantially straight along the lateral direction A from the first side 41 to the second side 43.

The third articulation surface 63 further extends along an oblique direction that is sloped substantially linearly as it extends rearward along the longitudinal direction L. Thus, the third articulation surface 63 extends toward the first endplate 32 along the transverse direction T as it extends rearwardly along the longitudinal direction L, so as to define an angle with respect to the longitudinal direction L. The angle can be anywhere within the range of approximately 10° and approximately 50°, for instance between approximately 20° and approximately 40°, and in particular can be about 30°. Thus, the front end of the third articulation surface 63 is below the rear end of the third articulation surface 63. It should be appreciated that while the third articulation surface 63 extends substantially straight along both the lateral direction A and the oblique direction, the third articulation surface can alternatively be curved, e.g. concave or convex, along part or all of either or both of the lateral direction A and the oblique direction, or can assume any suitable alternative geometry as desired. The third articulation surface 63 defines a contact location 81 (see FIG. 3B) against which the contact location 69 of the first articulation surface 59 abuts, and along which the contact location 69 of the first articulation surface 59 rides.

The stop member 76 can be configured as a lip that extends out from the front end of the third articulation surface 63. For instance, stop member 76 can extend forward with respect to the front end of the third articulation surface 63, and can further extend up along the transverse direction T with respect to the front end of the third articulation surface. As will be described in more detail below, the stop member 76 is configured to limit movement of the first endplate 32 as the first endplate 32 travels forward relative to the second endplate 34, for instance during flexion.

With continuing reference to FIGS. 2C-D, the fourth articulation member 64 extends from the second endplate body 48, and can be integral and monolithic with the second endplate body 48 or discreetly attached to the second endplate body 48 as desired. The fourth articulation member 64 is rearwardly spaced from the first articulation member 58 along the longitudinal direction L, such that the third and fourth articulation members 62 and 64 are separated by the second endplate body 48, and in particular separated by the inner surface 56. The inner surface 56 can be curved and convex as it extends along the lateral direction A as illustrated, and can further be curved and convex as it extends along the longitudinal direction L from the first side 41 to the second side 43. The curvature along the lateral direction A can be the same or different, for instance greater, than the curvature along the longitudinal direction L. It should be appreciated, however, that the inner surface 56 can define any suitable alternative geometry as desired. For instance, the inner surface 56 can extend substantially straight in one or both of the longitudinal direction L and the lateral direction A.

In accordance with the illustrated embodiment, the fourth articulation member 64 extends from the inner surface 56, and is recessed with respect to the inner surface 56 of the second endplate body 48. The fourth articulation member 64 defines the fourth articulation surface 65, and a stop member 80 that extends out from the fourth articulation surface 65. The fourth articulation surface can define a concave pocket having any suitable geometry as desired. In accordance with the illustrated embodiment, the fourth articulation surface 65 is substantially centered between the sides 41 and 43 of the second endplate 34 along the lateral direction A. Because the fourth articulation surface 65 is defined by the fourth articulation member 62, and because the fourth articulation member 62 is supported by the second endplate body 48, it can be said that the fourth articulation surface 65 is supported by the second endplate body 48.

The fourth articulation member 64 defines a base 82 that can be oriented and configured as desired. For instance, in accordance with the illustrated embodiment, the base 82 is substantially planar along a plane defined by the longitudinal direction L and the lateral direction A. The base 82 is open at its outer, or rearward, end to the rear end 39 of the second endplate 34. Thus, the pocket defined by the fourth articulation member 64 is open at its outer longitudinal, or rearward, end as well as at its outer transverse, or upper, end. The base 82 can define any shape as desired, and can be substantially triangular or v-shaped in accordance with the illustrated embodiment with respect to a view along the transverse direction T from the outer surface 50 toward the inner surface 54. The fourth articulation member 64 can further define first and second side walls 84a and 84b that converge toward each other as they extend inwardly toward the front end 37, until the side walls 84a and 84b meet at a junction 84c. The side walls 84a and 84b can be curved as they extend forward as illustrated, or can extend linearly or in any alternative direction or combination of directions as desired. In accordance with the illustrated embodiment, the side walls 84a and 84b are symmetrical to each other. The junction 84c can similarly define a curvature as it extends from the first side wall 84a to the second side wall 84b, though it should be appreciated that the junction 84c can alternatively define an angular elbow, can extend substantially straight between the side walls 84a and 84b, or can define any suitable alternatively configured junction as desired.

Furthermore, the side walls 84a and 84b can be oblique with respect to the base 82, and can be angularly offset with respect to each other about any suitable angle as desired, such as between approximately 50° and approximately 130°, for instance between 70° and approximately 110°, such as approximately 90°. Thus, each of the side walls 84a and 84b can be angularly offset with respect to the longitudinal direction L at any suitable angle as desired, such that an axis that extends along the longitudinal direction L can bisect the angle defined by the side walls 84a and 84b. The side walls 84a and 84b can converge toward each other as they travel forward along the longitudinal direction L, and can meet at a junction 84c. The junction 84c can define a curvature as it extends from the first side wall 84a to the second side wall 84b, though it should be appreciated that the junction 84c can alternatively define an angular elbow, can extend substantially straight between the side walls 84a and 84b, or can define any suitable alternatively configured junction as desired. The fourth articulation member 64 can define a pocket having any size and shape as desired, and can be substantially triangular or v-shaped in accordance with the illustrated embodiment with respect to a view along the transverse direction T from the outer surface 50 toward the inner surface 54.

In accordance with the illustrated embodiment, the fourth articulation surface 65 is defined by the first and second side walls 84a and 84b. In particular, the first and second side walls 84a and 84b define respective first and second contact locations 88a and 88b that contact the first and second contact locations 71a and 71b, respectively, of the second articulation surface 61. For instance, the first contact location 71a of the second articulation member 60 is configured to ride along the first contact location 88a of the fourth articulation member 64, and the second contact location 71b of the second articulation member 60 is configured to ride along the second contact location 88b of the fourth articulation member 64 while the intermediate region 71c of the second articulation member 60 that extends between the first and second contact locations 71a and 71b remains spaced above the base 82 of the fourth articulation member 64. The base 82 can define the stop member 80 that is configured to limit movement of the first endplate 32 as the first endplate 32 travels rearward relative to the second endplate 34, for instance during extension.

Referring now to FIGS. 3A-F in general, when the intervertebral implant 30 is in a neutral position when the first and second endplates 32 and 34 are oriented substantially in a plane defined by the longitudinal direction L and the lateral direction A, and thus substantially normal to the sagittal plane when the intervertebral implant 30 is disposed in the intervertebral space. When the intervertebral implant 30 is in the neutral position, the central longitudinal axes 49 and 55 can be aligned with each other or extend substantially parallel to each other, the central lateral axes and 51 and 57 can be aligned with each other or extend substantially parallel to each other, and the central transverse axes 53 and 73 can be aligned with each other or extend substantially parallel to each other.

When the intervertebral implant 30 is in the neutral position, the contact location 69 of the first articulation member 58 abuts the third articulation surface 63 of the third articulation member 62 substantially centrally on the third articulation surface 63. Further, the first and second contact locations 71a and 71b of the second articulation member 60 abut and rest against the complementary first and second contact locations 88a and 88b of the fourth articulation member 64. Because the first and second contact locations 71a and 71b are symmetrical with respect to each other about the central longitudinal axis 49, and because the first and second contact locations 88a and 88b are symmetrical with respect to each other about the central longitudinal axis 55, the first and second contact locations 71a and 71b are positioned at respective similar positions with respect to the complementary first and second contact locations 88a and 88b.

The entirety of the inner surface 54 of the first endplate 32 is spaced from the inner surface 56 of the second endplate 34, and is spaced from an entirety of the second endplate. The intermediate region 71c is spaced from the second endplate 34, and in particular is spaced from the base 82 of the fourth articulation member 64. Thus, the first and second endplates 32 and 34 contact each other at only three interfaces, namely 1) a first interface defined by the contact location 69 of the first articulation member 58 and the contact location defined by the third articulation surface 63 of the third articulation member 62, 2) a second interface defined by the first contact location 71a and the first contact location 88a, and 3) a third interface defined by the second contact location 71b and the second contact location 88b.

The present disclosure recognizes that in some instances, for instance when the anterior longitudinal ligament is removed alone or in combination with removal of the posterior longitudinal ligament during a surgical procedure, it may be desirable to provide an intervertebral implant that promotes one or more up to all of proper flexion-extension, proper combined motion during axial rotation that induces lateral bending, and proper combined motion during lateral bending that induces axial rotation. As will be described below with reference to FIGS. 4A-7G, the intervertebral implant 30 induces 1) movement of the first endplate 32 along the anterior-posterior direction relative to the second endplate 34, for instance during flexion-extension, 2) axial rotation of the first endplate 32 relative to the second endplate 34 during lateral bending of the first endplate 32 relative to the second endplate 34, 3) lateral bending of the first endplate 32 relative to the second endplate 34 during axial rotation of the first endplate 32 relative to the second endplate 34.

Referring to FIGS. 1A and 4A-5E, the intervertebral implant 30 promotes pure flexion and extension of the superior vertebra 22a relative to the inferior vertebra 22b, but as will be appreciated from the description below also allows flexion of the superior vertebra 22a in combination with axial rotation and lateral bending. For instance, as illustrated in FIGS. 4A-E, as forces are applied to the vertebrae 22a and 22b that induces flexion, the first endplate 32 articulates forward relative to the second endplate 34 along a convex path of motion. As illustrated in FIGS. 5A-E, as forces are applied to the 22a and 22b that induces extension, the first endplate 32 articulates rearward relative to the second endplate 34 along the convex path of motion.

Figure 3A:
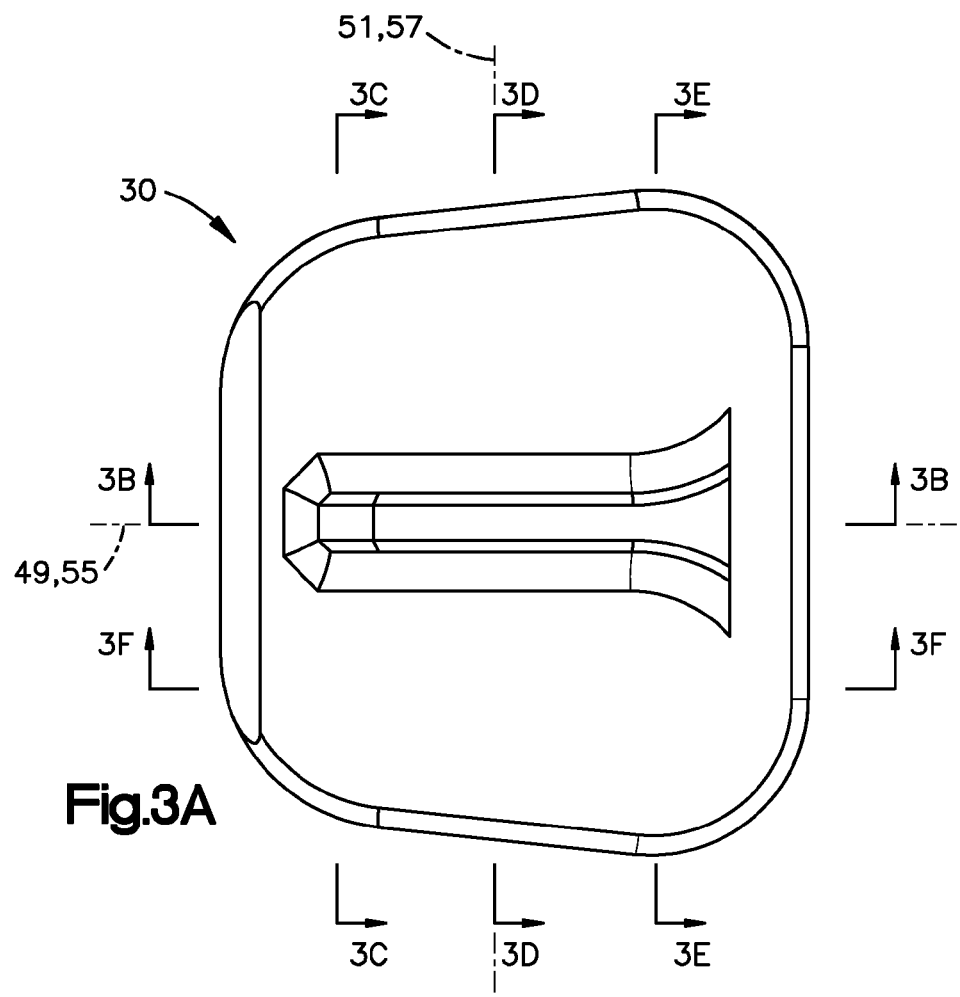
FIG. 3A is a top plan view of the intervertebral implant illustrated in FIG. 1C, shown in a neutral position.
Figure 3B:
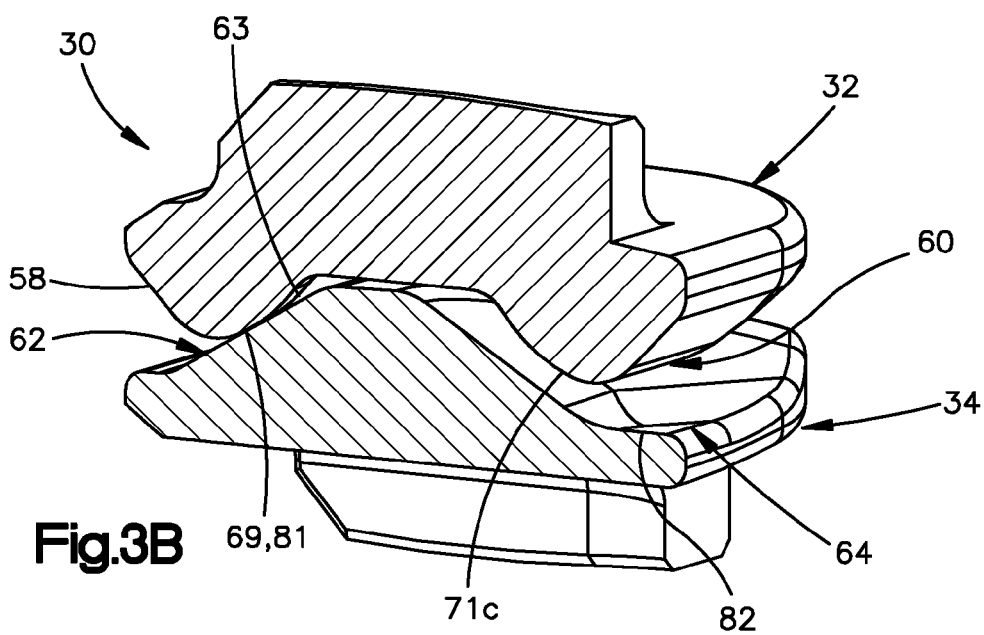
FIG. 3B is a cross-sectional view of the intervertebral implant illustrated in FIG. 3A, taken at midline 3B-3B.
Figure 3C:
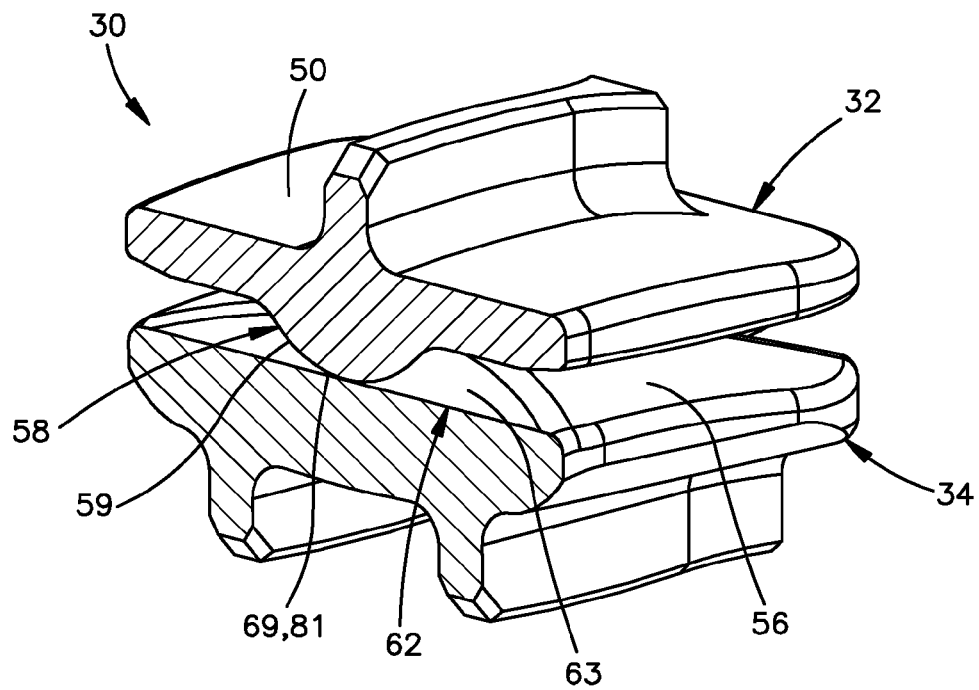
FIG. 3C is a cross-sectional view of the intervertebral implant illustrated in FIG. 3A, taken at line 3C-3C.
Figure 3D:
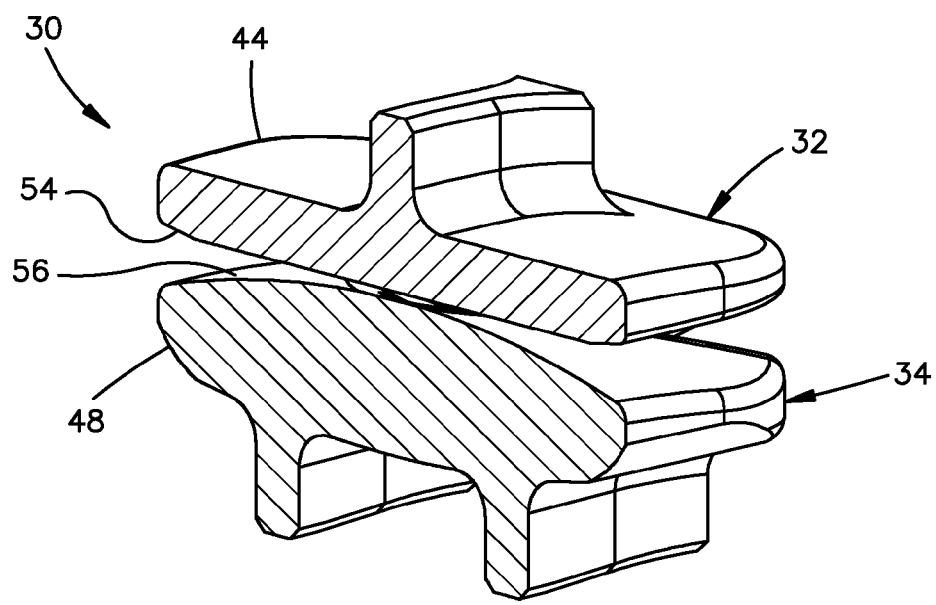
FIG. 3D is a cross-sectional view of the intervertebral implant illustrated in FIG. 3A, taken at midline 3D-3D.
Figure 3E:
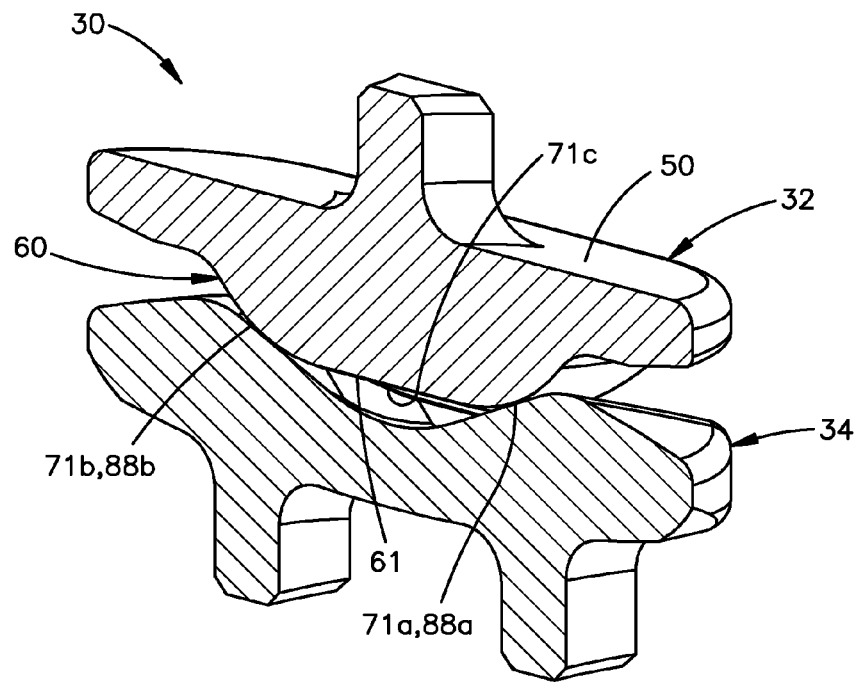
FIG. 3E is a cross-sectional view of the intervertebral implant illustrated in FIG. 3A, taken at line 3E-3E.
Figure 3F:
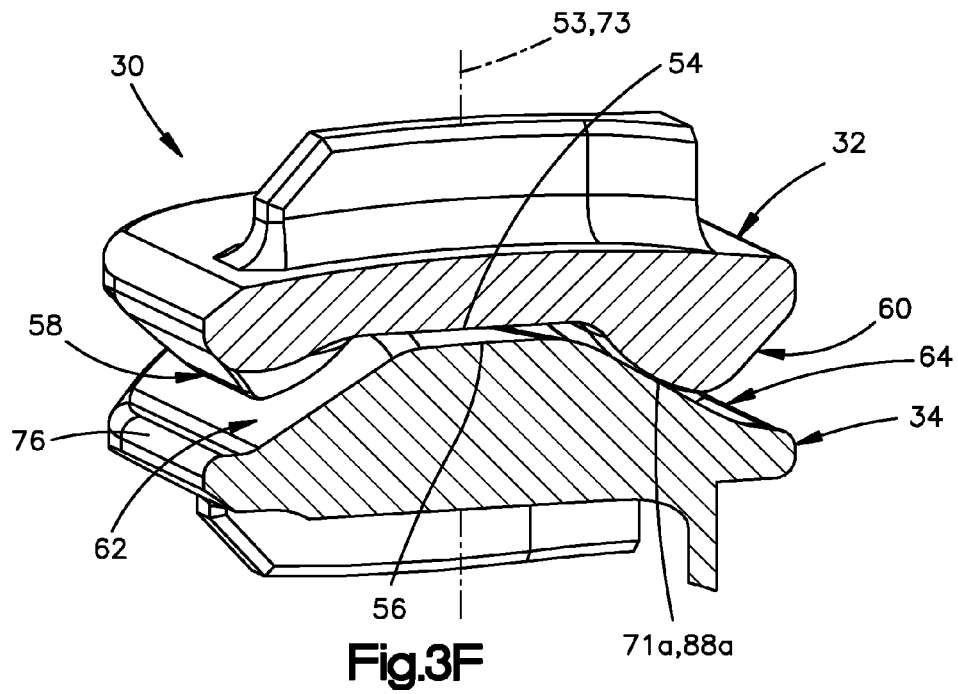
FIG. 3F is a cross-sectional view of the intervertebral implant illustrated in FIG. 3A, taken at line 3F-3F.
Figure 4A:
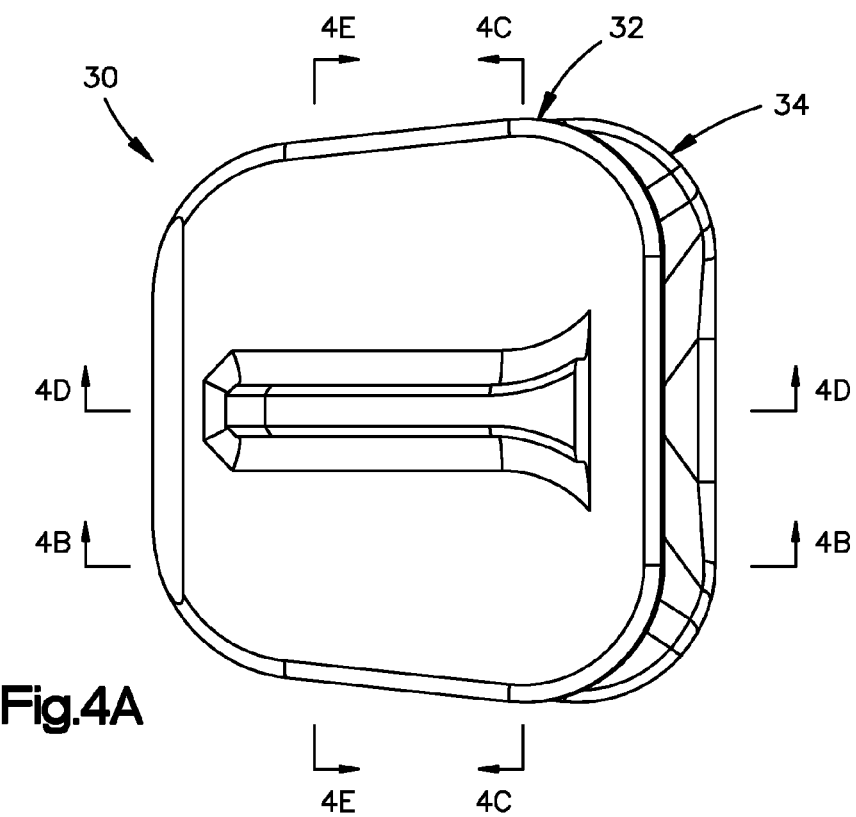
FIG. 4A is a perspective view of the intervertebral implant illustrated in FIG. 1C, but showing the upper endplate articulated anteriorly with respect to the lower endplate, during flexion.
Figure 4B:
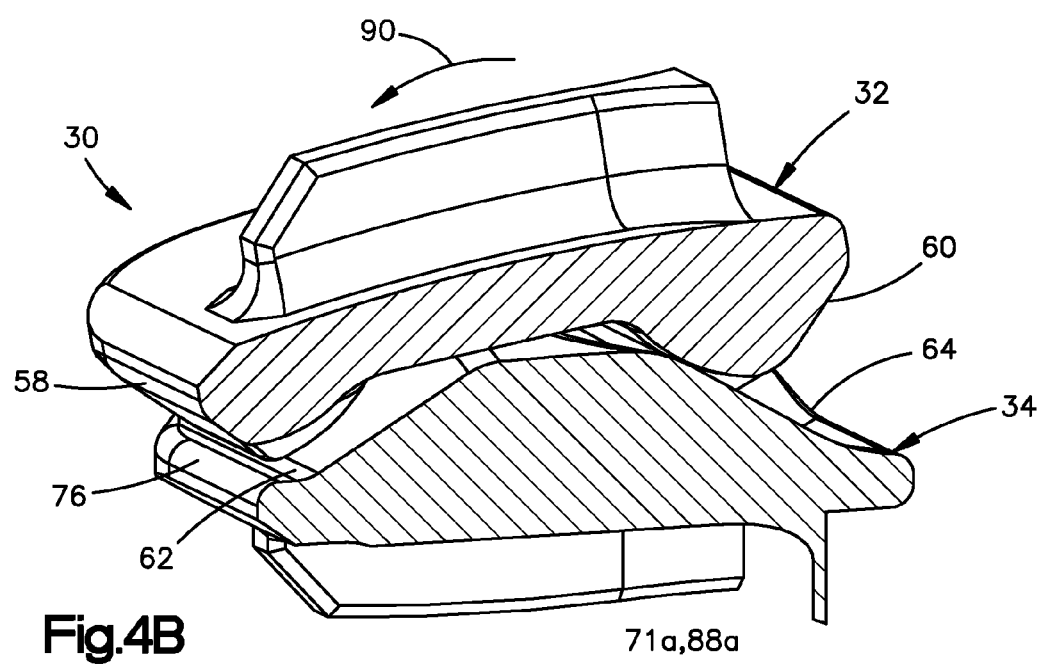
FIG. 4B is a cross-sectional view of the intervertebral implant illustrated in FIG. 4A, taken at line 4B-4B.
Figure 4C:
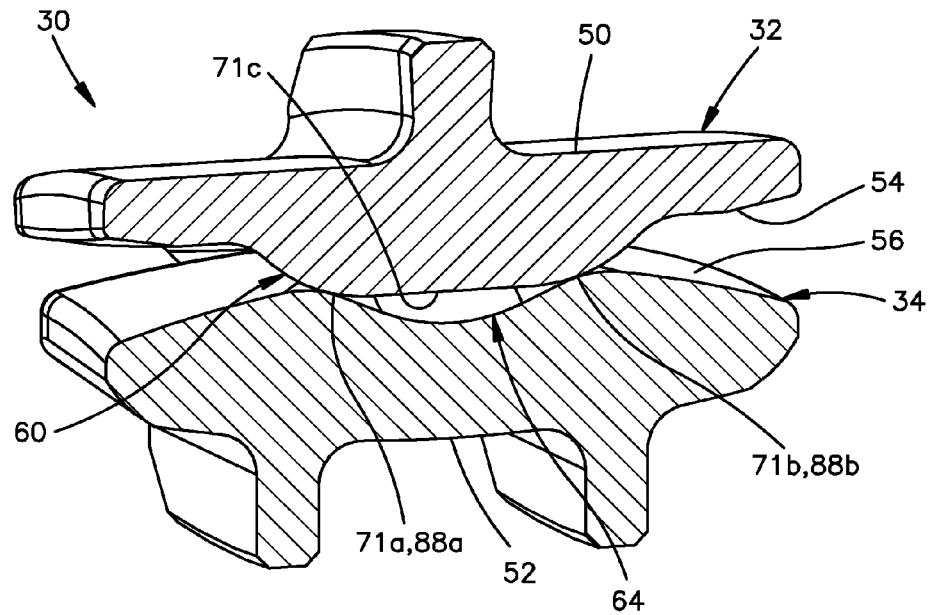
FIG. 4C is a cross-sectional view of the intervertebral implant illustrated in FIG. 4A, taken at line 4C-4C.

For instance, as illustrated in FIGS. 4A-C, during flexion, or forward movement of the first endplate 32 with respect to the second endplate 34 along the longitudinal direction L, the first and second contact locations 71a and 71b of the second articulation member 60 travel along the complementary first and second contact locations 88a and 88b of the fourth articulation member 64 in the forward longitudinal direction L with respect to the neutral position illustrated in FIGS. 3E-F. Because the first and second side walls 84a-b are sloped upward toward the inner surface 56 as they extend forward in the longitudinal direction L, the first and second contact locations 71a-b likewise travel upward as they travel forward in the longitudinal direction along the first and second contact locations 88a-b that are defined by the first and second side walls 84b, respectively. Further, because the first and second contact locations 88a and 88b are sloped substantially linearly, the first and second contact locations 71a-b likewise travel linearly as they travel forward in the longitudinal direction along the first and second contact location 88a-b. The first and second contact locations 71a-b are curved as they extend in the lateral direction A so as to define a convex surface along the lateral direction A with respect to the contact locations 88a-b, and are further curved as they extend in the longitudinal direction L so as to define a convex surface along the longitudinal direction L with respect to the contact locations 88a-b. Accordingly, each of the first and second contact locations 71a-b defines a point contact with respect to the first and second contact locations 88a-b, which can be substantially planar in accordance with the illustrated embodiment.

It should also be appreciated that because the first contact locations 71a and 88a are constructed symmetrically with respect to the second contact locations 71b and 88b, movement of the first contact location 71a along the first contact location 88a is symmetrical with respect to movement of the second contact location 71b along the second contact location 88b, and the first and second contact locations 71a and 71b are induced to travel at equal directions and rates along the respective complementary first and second contact locations 88a and 88b during flexion. Accordingly, the intervertebral implant 30 is configured to induce the first endplate 32 to move along the forward longitudinal direction L in response to an applied force that drives the intervertebral implant 30 to articulate during flexion.

Figure 4D:
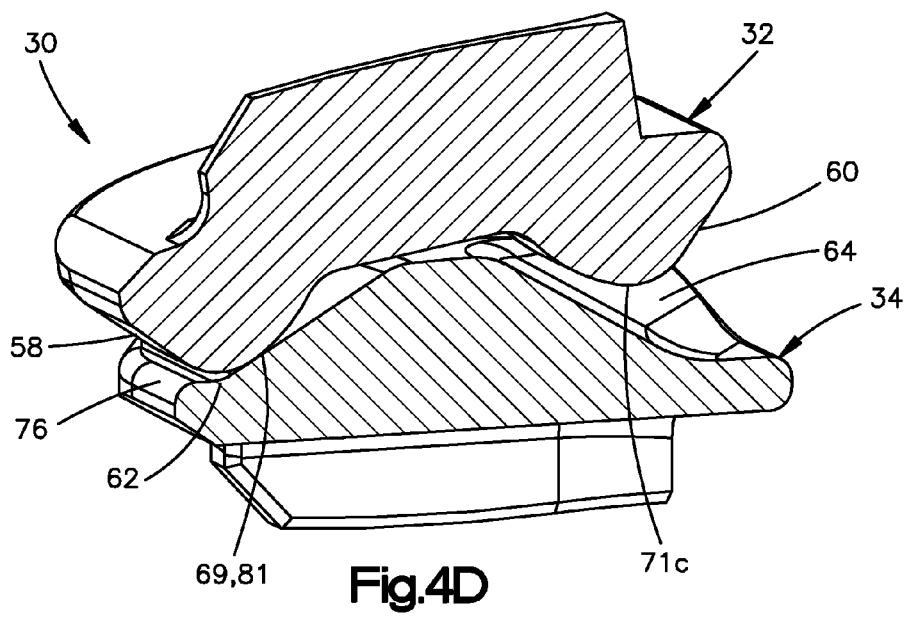
FIG. 4D is a cross-sectional view of the intervertebral implant illustrated in FIG. 4A, taken at a medial-lateral midline 4D-4D.
Figure 4E:
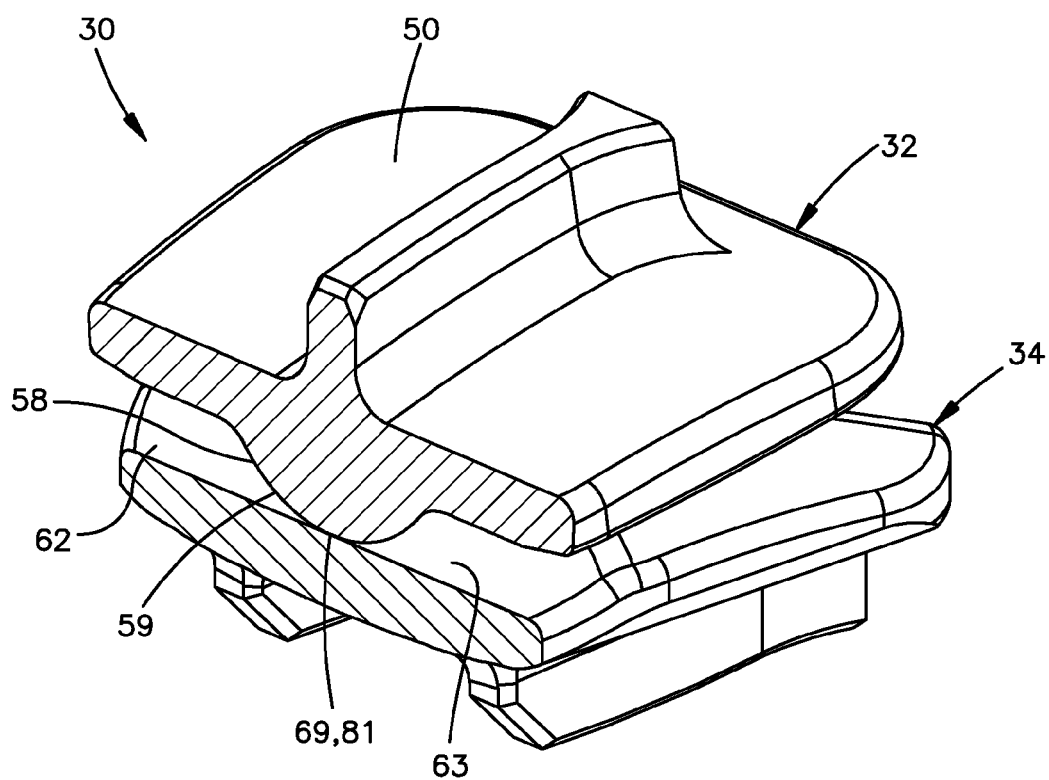
FIG. 4E is a cross-sectional view of the intervertebral implant illustrated in FIG. 4A, taken at line 4E-4E.

Referring now also to FIGS. 4D-E, during flexion, as the first and second contact locations 71a-b travel forward along the longitudinal direction L and upward in the transverse direction T as they ride along the respective first and second contact locations 88a-b, the contact location 69 of the first articulation member 58 travels forward along the longitudinal direction L and downward along the transverse direction T as it rides along the contact location 81 defined by the third articulation member 62. In particular, the contact location 69 of the first articulation member 58 travels along the complementary contact location 81 the third articulation member 62 in the forward longitudinal direction L with respect to the neutral position illustrated in FIGS. 3B-C. Because the third articulation surface 63 is sloped downward from the inner surface 56 as it extends forward in the longitudinal direction L, the contact location 69 of the first articulation member 58 likewise travels downward along the transverse direction T as it travels forward in the longitudinal direction L along the contact location 81. Further, because the contact location 81 is sloped substantially linearly, the contact location 69 likewise travels linearly as it travels forward in the longitudinal direction L along the contact location 81. The contact location 69 is curved as it extends in the lateral direction A so as to define a convex surface along the lateral direction A with respect to the contact location 81, and is further curved as is extends in the longitudinal direction L so as to define a convex surface along the longitudinal direction L with respect to the contact location 81. Accordingly, the contact location 69 defines a point contact with respect to the contact location 81, which is substantially planar in accordance with the illustrated embodiment. The first endplate 32 is configured to travel forward along the longitudinal direction L until the contact location 69 abuts the stop member 76 that extends out from the third articulation surface 63, at which point interference between the contact location 69 abuts the stop member 76 prevents further forward motion of the first endplate 32 with respect to the second endplate, and thus defines an outer boundary of permissible flexion.

Referring to FIGS. 4A-E generally, during flexion, the first and second contact locations 71a and 71b, and thus the rear end 39 of the first endplate 32 travel up along the transverse direction T as they travel forward along the longitudinal direction L, which causes the rear end 39 of the first endplate 32 to travel up along the transverse direction as it travels forward along the longitudinal direction L. Further, during flexion, the contact location 69 and thus the front end 37 of the first endplate travels down along the transverse direction T, the first endplate 32 moves along a convex path of motion 90 that extends in a plane defined by the longitudinal direction L and the transverse direction T, and extends about a center that is disposed below the first endplate 32 along the transverse direction T, and can further be disposed below the second endplate 34 along the transverse direction T, such that the second endplate 34 is disposed between the first endplate 32 and the center. Thus, the path of motion 90 is convex with respect to a view along the transverse direction T from the outer surface 50 toward the inner surface 54. The center of the convex path of motion can be located anywhere as desired, for instance below the second endplate 34, depending on the curvature of the convex path of motion 90, and can be stationary during motion of the first endplate 32 or can translate along the longitudinal direction L. The path of motion 90 can define a curvature that can vary depending on the geometric configuration of the first and second contact locations 71a-b and 88a-b. For instance, as described in more detail below, the first and second contact locations and 88a-b can be curved as they extend in the longitudinal direction between the base 82 and the inner surface 56, which can vary the convex path of motion 90 from the embodiment illustrated in FIGS. 4A-E.

Figure 5A:
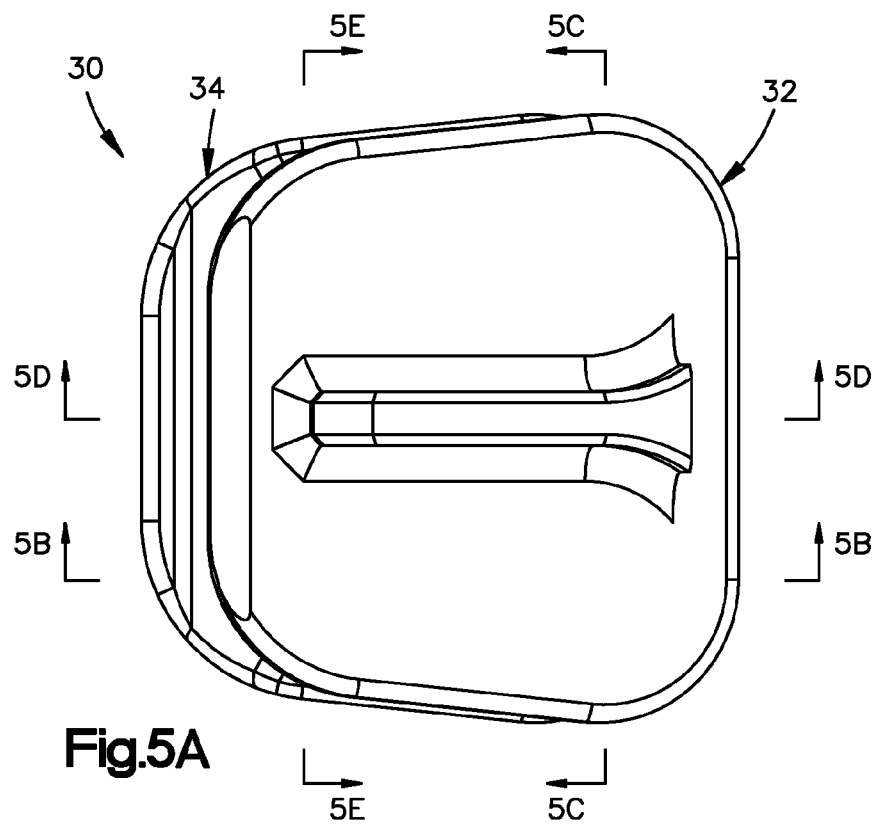
FIG. 5A is a perspective view of the intervertebral implant illustrated in FIG. 1C, but showing the upper endplate articulated posteriorly with respect to the lower endplate, during extension.
Figure 5B:
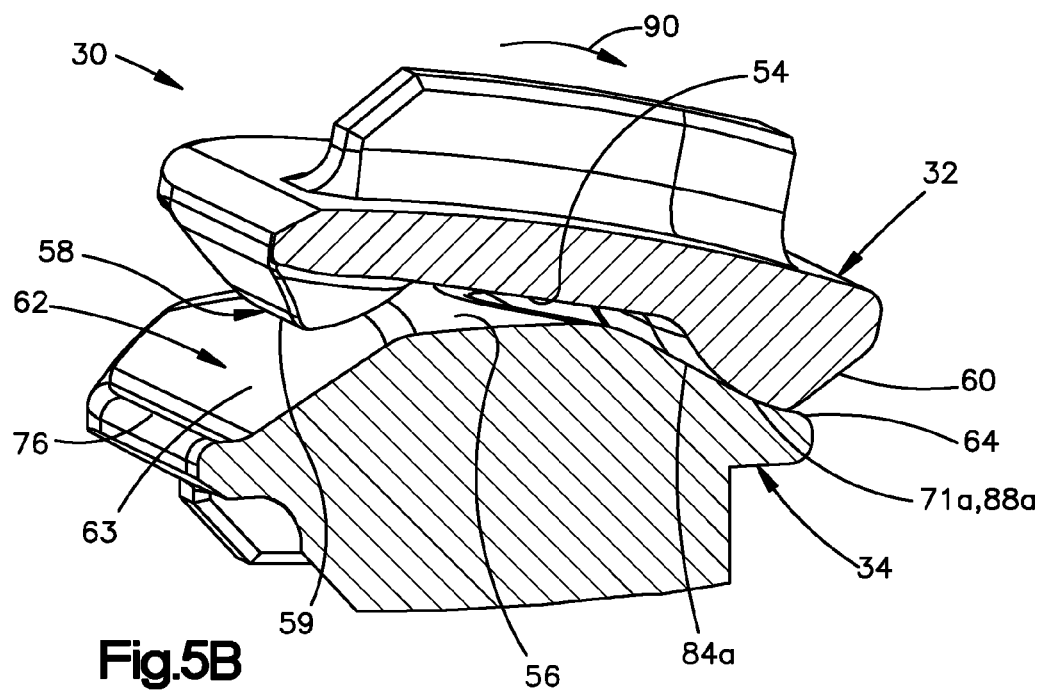
FIG. 5B is a cross-sectional view of the intervertebral implant illustrated in FIG. 5A, taken at midline 5B-4B.

Referring now to FIGS. 5A-C, during extension, or rearward movement of the first endplate 32 with respect to the second endplate 34 rearward along the longitudinal direction L, the first and second contact locations 71a and 71b of the second articulation member 60 travel along the complementary first and second contact locations 88*a* and 88*b* of the fourth articulation member 64 in the forward longitudinal direction L with respect to the neutral position illustrated in FIGS. 3E-F. Because the first and second side walls 84*a-b* are sloped downward from the inner surface 56 toward the base 82 as they extend rearward in the longitudinal direction L, the first and second contact locations 71*a-b* likewise travel downward as they travel rearward in the longitudinal direction L along the first and second contact locations 88*a-b* that are defined by the first and second side walls 84*b*, respectively. Further, because the first and second contact locations 88*a* and 88*b* are sloped substantially linearly, the first and second contact locations 71*a-b* likewise travel linearly as they travel rearward in the longitudinal direction L along the first and second contact location 88*a-b*.

It should also be appreciated that because the first contact locations 71*a* and 88*a* are constructed symmetrically with respect to the second contact locations 71*b* and 88*b*, movement of the first contact location 71*a* along the first contact location 88*a* is symmetrical with respect to movement of the second contact location 71*b* along the second contact location 88*b*, and the first and second contact locations 71*a* and 71*b* are induced to travel at equal directions and rates along the respective complementary first and second contact locations 88*a* and 88*b* during extension. Accordingly, the intervertebral implant 30, such as the second endplate 34, is configured to induce the first endplate 32 to move rearward along the longitudinal direction L in response to an applied force that drives the intervertebral implant 30 to articulate during extension.

Figure 5E:
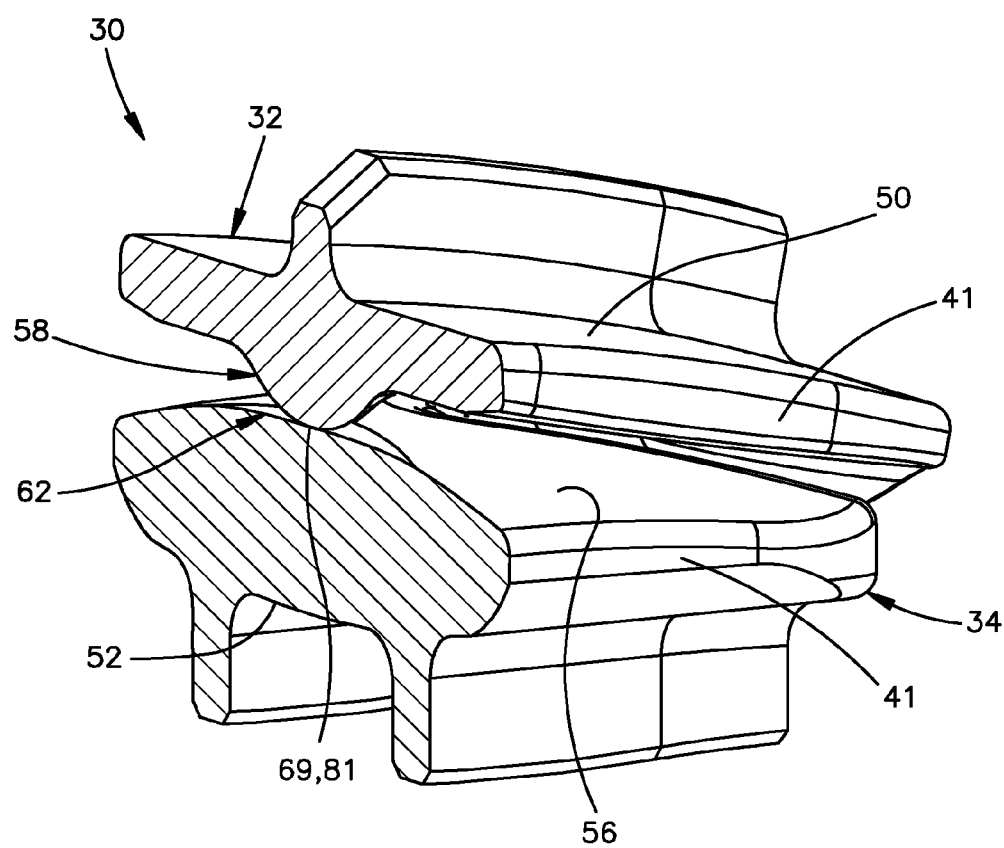
FIG. 5E is a cross-sectional view of the intervertebral implant illustrated in FIG. 5A, taken at line 5E-5E.

Referring now also to FIGS. 5D-E, during extension, as the first and second contact locations 71*a-b* travel rearward along the longitudinal direction L and downward in the transverse direction T as they ride along the respective first and second contact locations 88*a-b*, the contact location 69 of the first articulation member 58 travels rearward along the longitudinal direction L and upward along the transverse direction T as it rides along the contact location 81 defined by the third articulation member 62. In particular, the contact location 69 of the first articulation member 58 travels rearward along the complementary contact location 81 the third articulation member 62 in the longitudinal direction L with respect to the neutral position illustrated in FIGS. 3B-C. Because the third articulation surface 63 is sloped upward toward the inner surface 56 as it extends rearward in the longitudinal direction L, the contact location 69 of the first articulation member 58 likewise travels upward along the transverse direction T as it travels rearward in the longitudinal direction L along the contact location 81. Further, because the contact location 81 is sloped substantially linearly, the contact location 69 likewise travels linearly as it travels forward in the longitudinal direction L along the contact location 81.

The first endplate 32 is configured to travel rearward along the longitudinal direction L until the second articulation member 60 abuts the base 82, which can define a stop member, such that interference between the second articulation member 60 and the base 82 prevents further rearward motion of the first endplate 32 with respect to the second endplate 34, and thus defines an outer boundary of permissible extension along both the clockwise direction 92 and the counterclockwise direction 94.

Referring to FIGS. 5A-E generally, during extension, the first and second contact locations 71*a* and 71*b*, and thus the rear end 39 of the first endplate 32, travels down along the transverse direction T as they extend rearward along the longitudinal direction L. Further, during extension, the contact location 69 and thus the front end 37 of the first endplate 32 travels up along the transverse direction T. Accordingly, during extension, the first endplate 32 moves along the convex path of motion 90.

Furthermore, referring to FIGS. 4A-5E generally, it should be appreciated that during flexion and extension, when the first endplate 32 articulates between the boundaries of flexion and extension, the inner surface 54 of the first endplate 32 is spaced from, for instance above, the second endplate 34, and in particular the inner surface 56 of the second endplate 34, along the transverse direction T. Furthermore, during flexion and extension the first articulation member 58 is spaced from, for instance above, the second endplate 34, and in particular the third articulation member 62 of the second endplate 34, at all regions with the exception of the contact location 69. Further still, during flexion and extension, the second articulation member 60 is spaced from, for instance above, the second endplate 34, and in particular the fourth articulation member 64 of the second endplate 34, at all regions with the exception of the first and second contact locations 71*a-b*. Thus, during flexion and extension along the flexion-extension path of motion 90 between the boundaries of flexion and extension, the first endplate 32 contacts the second endplate only at three points of contact that are defined by the contact locations 69 and 71*a-b*.

Referring now to FIGS. 1A and 6A-I, the intervertebral implant 30 can induce axial rotation of the first endplate 32 during lateral bending of the first endplate 32. Thus, when a force is applied to the first endplate 32 that drives the first endplate 32 to rotate about a substantially longitudinal axis so as to undergo lateral bending, the intervertebral implant 30, and in particular the second endplate 34, also induces the first endplate 32 to rotate about a substantially transverse axis that extends substantially in the transverse direction T, thereby promoting axial rotation of the first endplate 32 about the substantially transverse axis relative to the second endplate 34. Thus, during operation, the first and second articulation members 58 and 60 can ride along the third and fourth articulation members 62 and 64, respectively, such that rotation of the first endplate 32 about a first axis of rotation that is substantially perpendicular to the insertion direction induces rotation of the first endplate 32 about a second axis of rotation that is substantially perpendicular to the first axis of rotation.

For instance, as illustrated in FIGS. 6A-E, during lateral bending, or rotational movement of the first endplate 32 with respect to the second endplate 34 about a longitudinal axis of rotation, which can be stationary or can move during lateral bending, one of the first and second contact locations 71*a* and 71*b* of the second articulation member 60 travels along the complementary first and second contact locations 88*a* and 88*b* of the fourth articulation member 64 along a first direction, and the other of the first and second contact locations 71*a* and 71*b* of the second articulation member 60 travels along the complementary first and second contact locations 88*a* and 88*b* of the fourth articulation member 64 along a second direction that is opposite the first direction.

Lateral bending of the first endplate 32 with respect to the second endplate 34 will now be described with respect to rotation of the first endplate 32 with respect to the second endplate 34 along a first or clockwise direction 92 from a view that is oriented forward along the longitudinal direction L, it being appreciated that lateral bending of the first endplate along a second or counterclockwise direction 94 that is opposite the clockwise direction 92 is symmetrical with respect to the lateral bending about the clockwise direction 92. It should be appreciated that during lateral bending, the outer surface 50 of the first endplate 32, and in particular the central lateral axis 51, angulates with respect to the lateral direction A.

As described above, the first and second side walls 84*a-b* extend forward along the longitudinal direction L as they extend upward along the transverse direction T from the base 82 to the inner surface 56. Conversely, the first and second side walls 84*a-b* extend rearward along the longitudinal direction L as they extend down along the transverse direction T from the inner surface 56 to the base 82. Furthermore, the first and second side walls 84*a-b* extend forward along the longitudinal direction L from the outer or rear end 39 of the second endplate 34 to the junction 84*c* as they converge toward each other, and thus toward the central longitudinal axis 55. For instance, the first and second side walls 84*a-b* can each be curved as they extend from the rear end 39 to the junction 84*c* along a concave curvature, though it should be appreciated that the first and second side walls 84*a-b* can define any suitable geometry as desired. Conversely, the first and second side walls 84*a-b* extend rearward along the longitudinal direction L from the junction 84*c* to the outer or rear end 39 of the second endplate 34 as they diverge away from each other, and thus away from the central longitudinal axis 55.

Accordingly, when a lateral bending force is applied to the intervertebral implant 30 that biases the first endplate 32 to rotate with respect to the second endplate 34 along the clockwise direction 92, the first contact location 71*a* travels upward along the transverse direction T as it rides along the first contact location 88*a*, while the second contact location 71*b* travels down along the transverse direction T as it rides along the second contact location 88*b*. Thus, the outer surface 50 angulates with respect to the neutral plane that is defined by the longitudinal direction L and the lateral direction A, such that one of the sides 41 and 43 of the first endplate 32 is disposed below the other of the sides 41 and 43 along the transverse direction. In accordance with the illustrated embodiment, when the first endplate 32 angulates along the clockwise direction 92, the first side 41 moves up along the transverse direction T and the second side 43 moves down along the transverse direction T.

Furthermore, the first contact location 71*a* moves away from the central longitudinal axis 55 as the first endplate 32 rotates along the clockwise direction 92, and further moves forward along the longitudinal direction L as it moves away from the central longitudinal axis 55. Accordingly, the first contact location moves rearwardly along the longitudinal direction L as it moves up along the transverse direction T during lateral bending of the first endplate 32 along the clockwise direction 92. The second contact location 71*b* moves toward from the central longitudinal axis 55 as the first endplate 32 rotates along the clockwise direction 92, and further moves rearward along the longitudinal direction L as it moves toward the central longitudinal axis 55.

Referring also to FIGS. 6F-I, as the first contact location 71*a* moves forward along the longitudinal direction L and the second contact location 71*b* moves rearward along the longitudinal direction L, the first endplate 32, for instance at the rear end 39 of the first endplate 32, rotates about a transverse axis that extends substantially parallel to the central transverse axis 53. As the first endplate 32 rotates about the transverse axis, the contact location 69 of the first articulation member 58 translates along the contact location 81 that is defined by the third articulation surface 63. In accordance with the illustrated embodiment, the contact location 69, and thus the front end 37 of the first endplate 32, translates along a direction that includes a lateral directional component, the lateral directional component being directed toward the side 41 or 43 that is located closest to the contact location 71*a* or 71*b* that moves rearward along the longitudinal direction L (or down along the transverse direction T) during lateral bending. Otherwise stated, the contact location 69 travels along contact location 81 in the lateral direction A toward the one of the contact locations 71*a-b* that travels rearward (or downward) during lateral bending. When the first endplate 32 articulates about the clockwise direction 92, the contact location 69 travels toward the second contact location 71*a* and thus toward the second side 43.

Because the third articulation surface 63 extends up along the transverse direction T as it extends rearward from the front end 37 of the second endplate 34 to the inner surface 56, the contact location 69 likewise travels up along the transverse direction T as it travels rearward along the longitudinal direction and outward along the lateral direction A with respect to the central longitudinal axis 49. Similarly, the contact location 69 travels down along the transverse direction T as it travels forward along the longitudinal direction and laterally inward along the lateral direction A toward the central longitudinal axis 49. Furthermore, because the third articulation surface 63 extends substantially linearly between the front end 37 of the second endplate 34 and the inner surface 56, the contact location 69 travels substantially linearly as it moves laterally inward and outward with respect to the central longitudinal axis 49 (and thus forward and down, and rearward and up, respectively, along the transverse direction T) along the third articulation surface 63. Furthermore, because the first endplate 32 angulates with respect to the lateral-longitudinal plane, the contact location 69 pivots along the contact location 81 as the first endplate 32 angulates with respect to the second endplate 34 along the clockwise and counterclockwise directions 92 and 94, respectively.

It should be appreciated that rotation of the first endplate 32 relative to the second endplate 34 along the counterclockwise direction 94 is symmetrical with respect to rotation of the first endplate 32 relative to the second endplate 34 along the clockwise direction. Accordingly, while the first contact location 71*a* travels up and forward along the first contact location 88*a* and the second contact location 71*b* travels down and rearward along the second contact location 88*b* during clockwise rotation, the first contact location 71*a* travels down and rearward along the first contact location 88*a* and the second contact location 71*b* travels up and forward along the second contact location 88*b* during counterclockwise rotation. Furthermore, because the contact location 69 travels along the lateral direction A toward the one of the contact locations 71*a-b* that travels rearward during lateral bending, the contact location 69 travels along the lateral direction A toward the first contact location 71*a* during counterclockwise rotation.

Figure 6A:
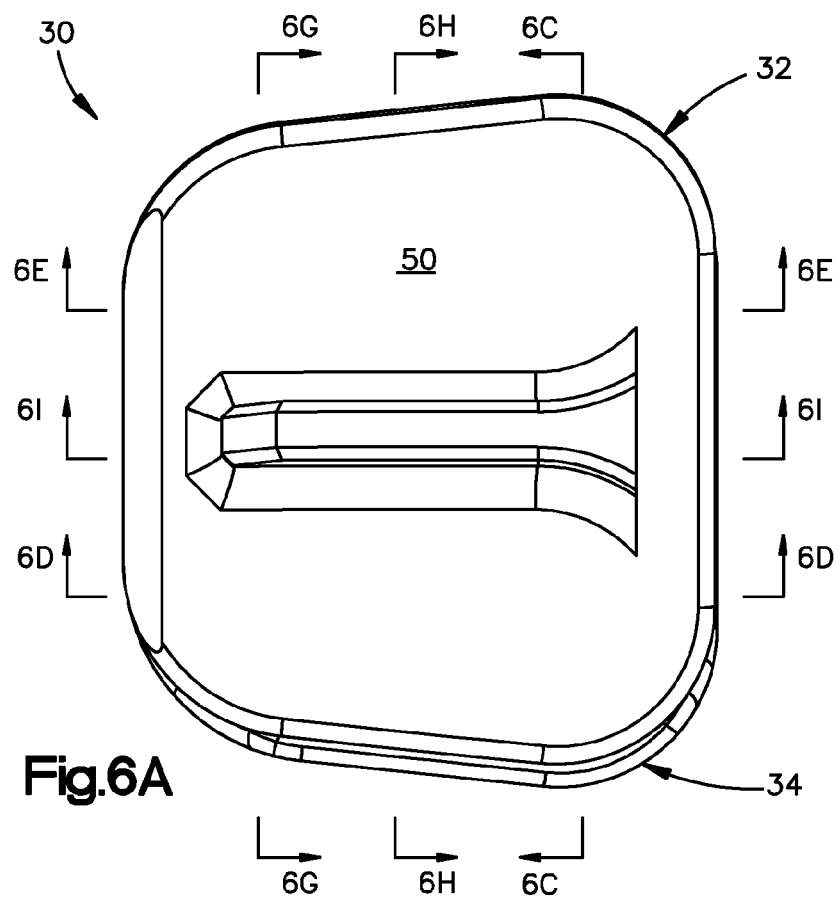
FIG. 6A is a top plan view of the intervertebral implant illustrated in FIG. 1C, but showing the upper endplate articulated laterally with respect to the lower endplate, during lateral bending.
Figure 6B:
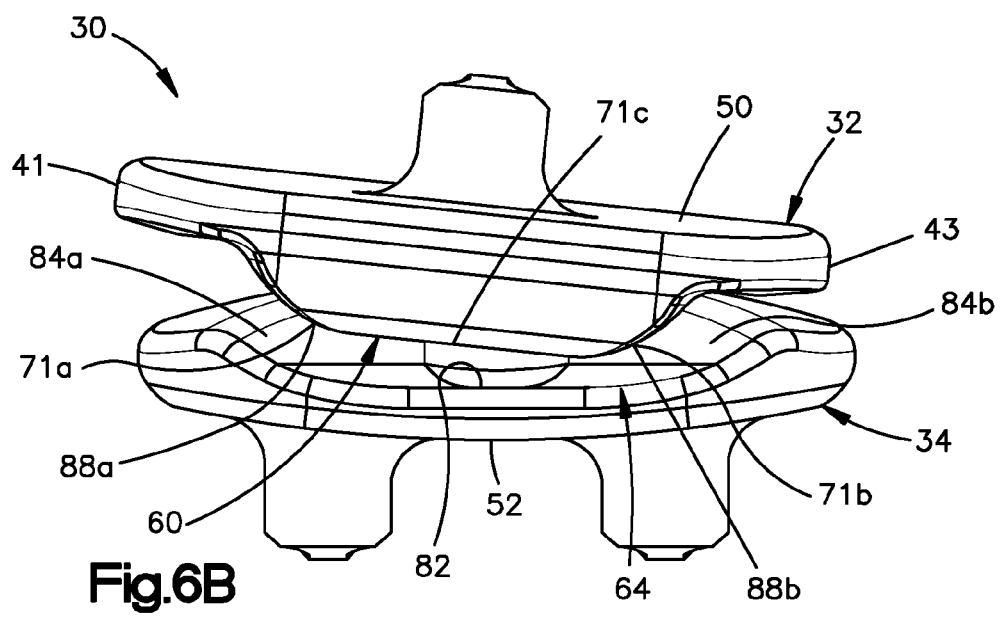
FIG. 6B is a rear elevation view of the intervertebral implant illustrated in FIG. 6A.
Figure 6C:
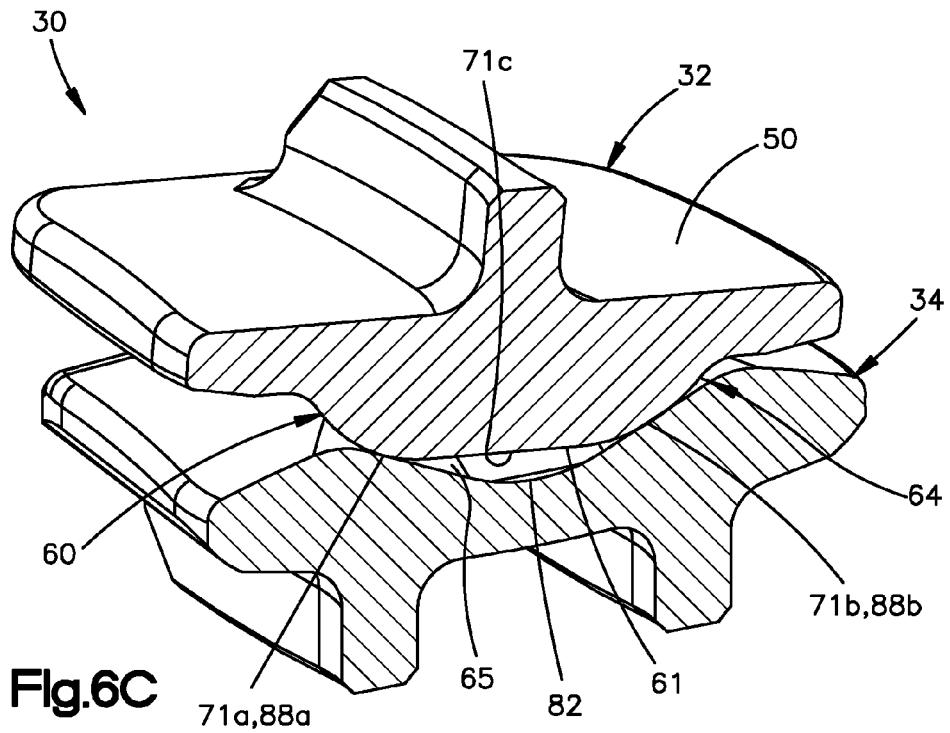
FIG. 6C is a cross-sectional view of the intervertebral implant illustrated in FIG. 6A, taken at midline 6C-6C.
Figure 6D:
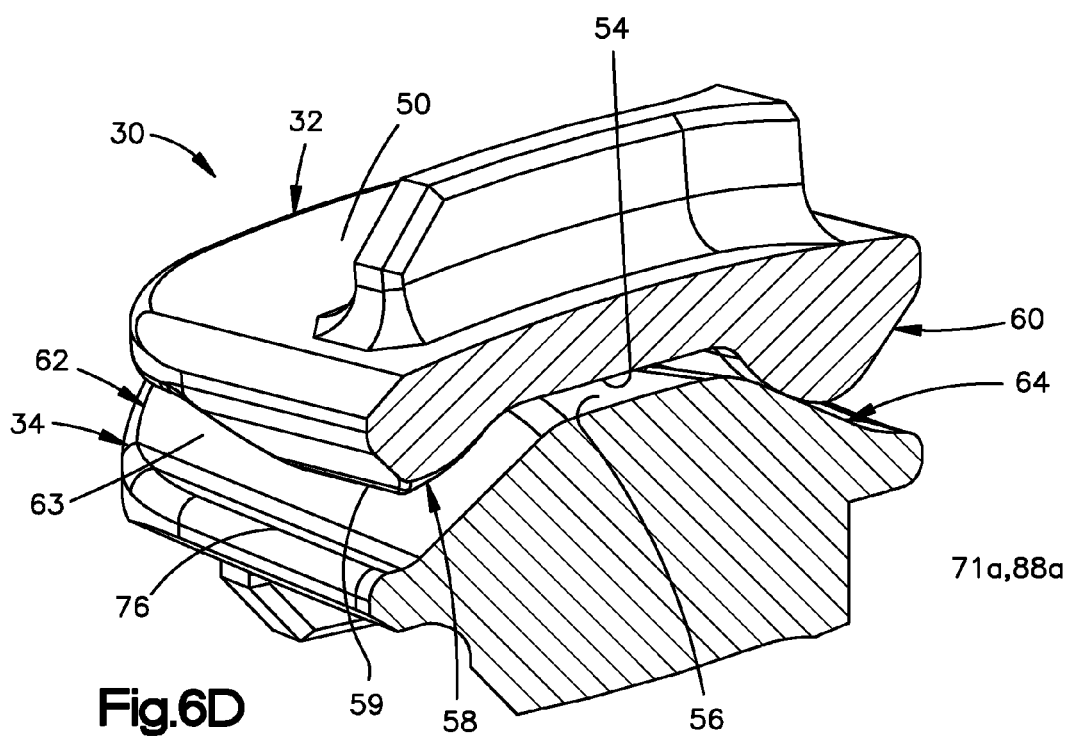
FIG. 6D is a cross-sectional view of the intervertebral implant illustrated in FIG. 6A, taken at line 6D-6D.
Figure 6G:
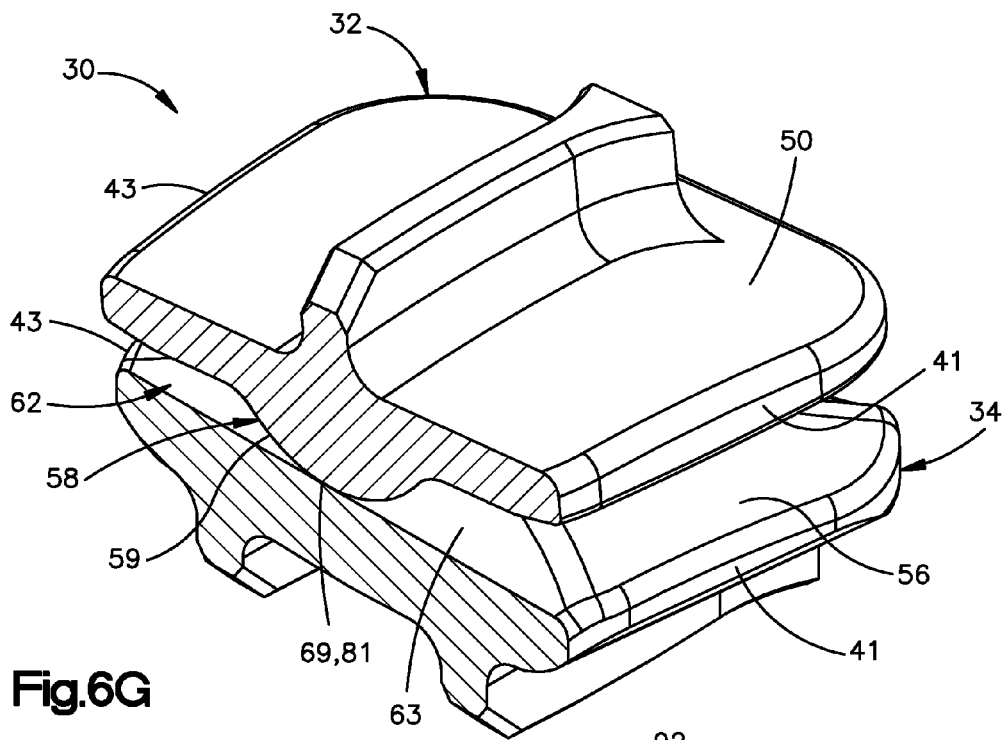
FIG. 6G is a cross-sectional view of the intervertebral implant illustrated in FIG. 6A, taken at line 6G-6G.
Figure 6H:
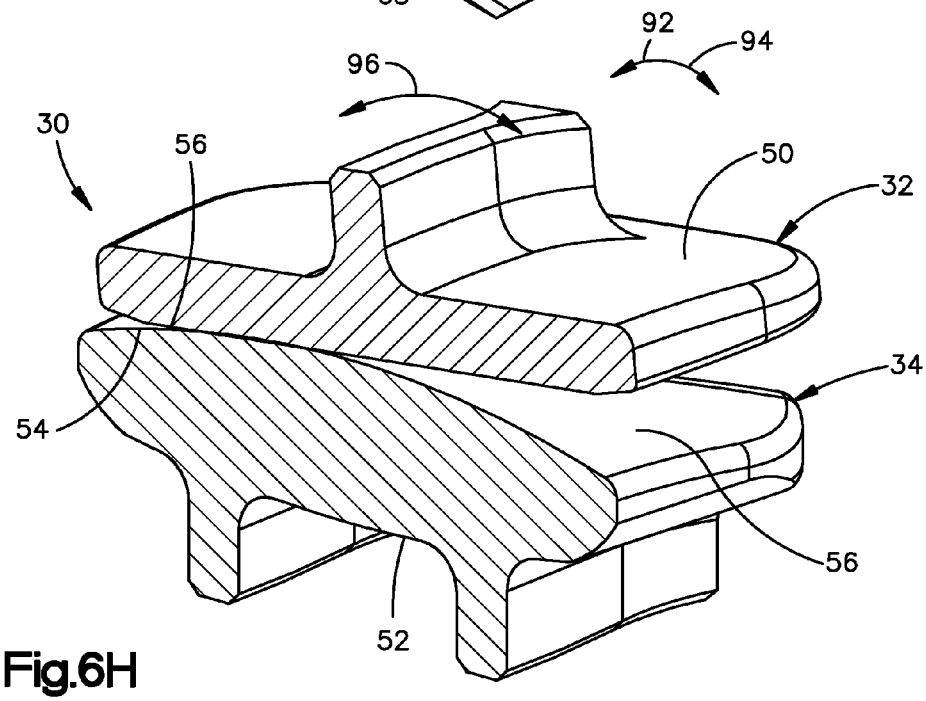
FIG. 6H is a cross-sectional view of the intervertebral implant illustrated in FIG. 6A, taken at anterior-posterior midline 6H-6H.
Figure 6I:
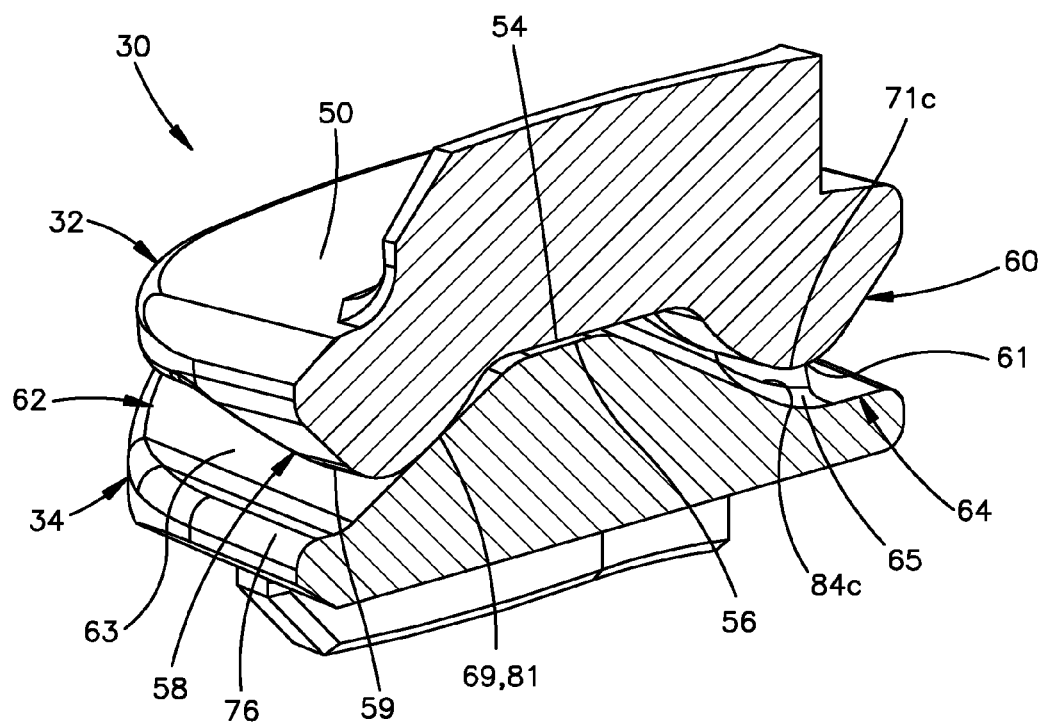
FIG. 6I is a cross-sectional view of the intervertebral implant illustrated in FIG. 6A, taken at medial-lateral midline 6I-6I.

As illustrated in FIG. 6H, the first endplate 32 articulates along the clockwise and counterclockwise directions 92 and 94, respectively, until the inner surface 54 of the first endplate 32 contacts the inner surface 56 of the second endplate, thereby providing a mechanical interference that defines the outer boundary of lateral bending. Furthermore, it should be appreciated that the first endplate 32 travels along a concave path of motion 96 as it articulates along the clockwise and counterclockwise directions 92 and 94, respectively. The concave path of motion 96 is concave from a viewpoint directed down along the transverse direction T. Thus, the first endplate 32 is configured to reciprocally articulate forward and rearward along the convex path of motion 90, and is configured to articulate along the clockwise and counterclockwise directions 92 and 94 along the concave path of motion 96, both alone and in combination with each other.

When the first endplate 32 articulates between the outer boundaries of lateral bending, the inner surface 54 of the first endplate 32 is spaced from, for instance above, the second endplate 34, and in particular the inner surface 56 of the second endplate 34, along the transverse direction T. Furthermore, during lateral bending, the first articulation member 58 is spaced from, for instance above, the second endplate 34, and in particular the third articulation member 62 of the second endplate 34, at all regions with the exception of the contact location 69. Further still, during lateral bending, the second articulation member 60 is spaced from, for instance above, the second endplate 34, and in particular the fourth articulation member 64 of the second endplate 34, at all regions with the exception of the first and second contact locations 71a-b. Thus, as the first endplate 32 articulates between the outer boundaries of lateral bending, the first endplate 32 contacts the second endplate only at three points of contact that are defined by the contact locations 69 and 71a-b.

Referring now to FIGS. 1A and 7A-H, the intervertebral implant 30 can further promote lateral bending of the first endplate 32 during axial rotation of the first endplate 32. Thus, when a force is applied to the first endplate 32 that drives the first endplate 32 to rotate about a substantially transverse axis so as to undergo axial rotation, the intervertebral implant 30, and in particular the second endplate 34, also induces the first endplate 32 to rotate about a substantially longitudinal axis, thereby promoting lateral bending. Thus, during operation, the first and second articulation members 58 and 60 can ride along the third and fourth articulation members 62 and 64, respectively, such that rotation of the first endplate 32 about a first axis of rotation that is substantially perpendicular to the insertion direction induces rotation of the first endplate 32 about a second axis of rotation that is substantially perpendicular to the first axis of rotation.

For instance, as illustrated in FIGS. 7A-E, during axial rotation, or rotational movement of the first endplate 32 with respect to the second endplate 34 about a transverse axis of rotation, which can be stationary or can move during axial rotation, one of the first and second contact locations 71a and 71b of the second articulation member 60 travels along the complementary first and second contact locations 88a and 88b of the fourth articulation member 64 along a first direction, and the other of the first and second contact locations 71a and 71b of the second articulation member 60 travels along the complementary first and second contact locations 88a and 88b of the fourth articulation member 64 along a second direction that is opposite the first direction. It should be appreciated that during axial rotation, the central longitudinal and lateral axes 49 and 51 of the first endplate become angularly offset with respect to the central longitudinal and lateral axes 55 and 55 of the second endplate 34.

Axial rotation of the first endplate 32 with respect to the second endplate 34 will now be described with respect to rotation of the first endplate 32 with respect to the second endplate 34 along a first or clockwise direction 93 from a view that is oriented down toward the outer surface 50 along the transverse direction T, it being appreciated that axial rotation of the first endplate along a second or counterclockwise direction 98 that is opposite the clockwise direction 93 is symmetrical with respect to the axial rotation about the clockwise direction 93.

As described above, the first and second side walls 84a-b extend forward along the longitudinal direction L as they extend upward along the transverse direction T from the base 82 to the inner surface 56. Conversely, the first and second side walls 84a-b extend rearward along the longitudinal direction L as they extend down along the transverse direction T from the inner surface 56 to the base 82. Furthermore, the first and second side walls 84a-b extend forward along the longitudinal direction L from the outer or rear end 39 of the second endplate 34 to the junction 84c as they converge toward each other, and thus toward the central longitudinal axis 55. For instance, the first and second side walls 84a-b can each be curved as they extend from the rear end 39 to the junction 84c along a concave curvature, though it should be appreciated that the first and second side walls 84a-b can define any suitable geometry as desired. Conversely, the first and second side walls 84a-b extend rearward along the longitudinal direction L from the junction 84c to the outer or rear end 39 of the second endplate 34 as they diverge away from each other, and thus away from the central longitudinal axis 55.

Accordingly, when an axial rotation force is applied to the intervertebral implant 30 that biases the first endplate 32 to rotate with respect to the second endplate 34 along the clockwise direction 93, the first contact location 71a rides along the first contact location 88a along a direction upward along the transverse direction T, forward along the longitudinal direction L, and inward along the lateral direction A toward the central longitudinal axis 49. The second contact location 71b rides along the second contact location 88b, and travels down along the transverse direction T, rearward along the longitudinal direction L, and outward along the lateral direction A away from the central longitudinal axis 49. Because the first contact location 71a moves forward, and the second contact location 71b moves rearward, the first endplate 32 axially rotates relative to the second endplate 34 about a transverse axis. It should be further appreciated in accordance with the illustrated embodiment, when the first endplate 32 angulates along the clockwise direction 93, the first side 41 moves up along the transverse direction T and the second side 43 moves down along the transverse direction T, thereby further inducing lateral bending of the first endplate 32 as described above. As the first endplate 32 axially rotates along the clockwise direction 93, the first endplate 32 also laterally bends about the clockwise direction 92 illustrated in FIGS. 6A-H.

Figure 7A:
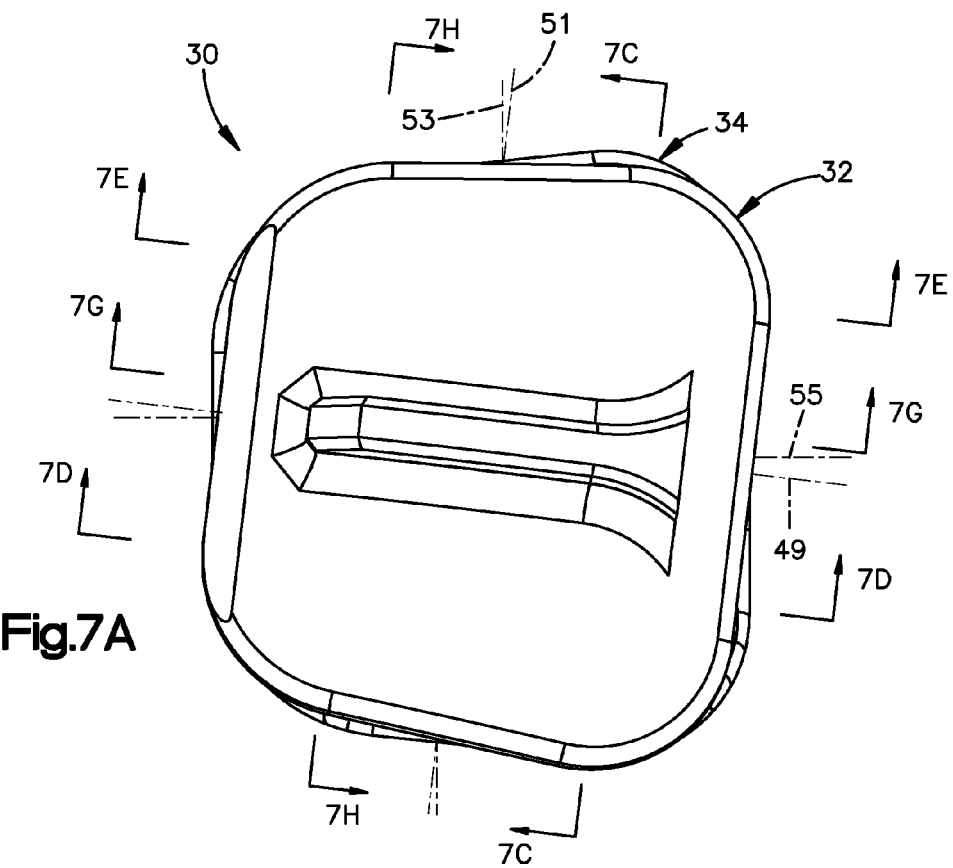
FIG. 7A is a top plan view of the intervertebral implant illustrated in FIG. 1C, but showing the upper endplate axially rotated with respect to the lower endplate, during axial rotation.
Figure 7B:
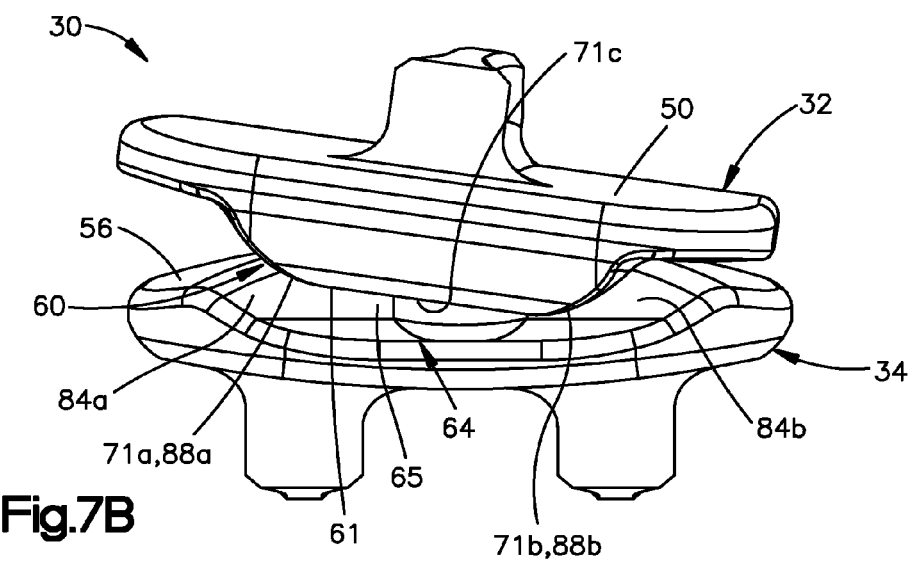
FIG. 7B is a front elevation view of the intervertebral implant illustrated in FIG. 7A.
Figure 7C:
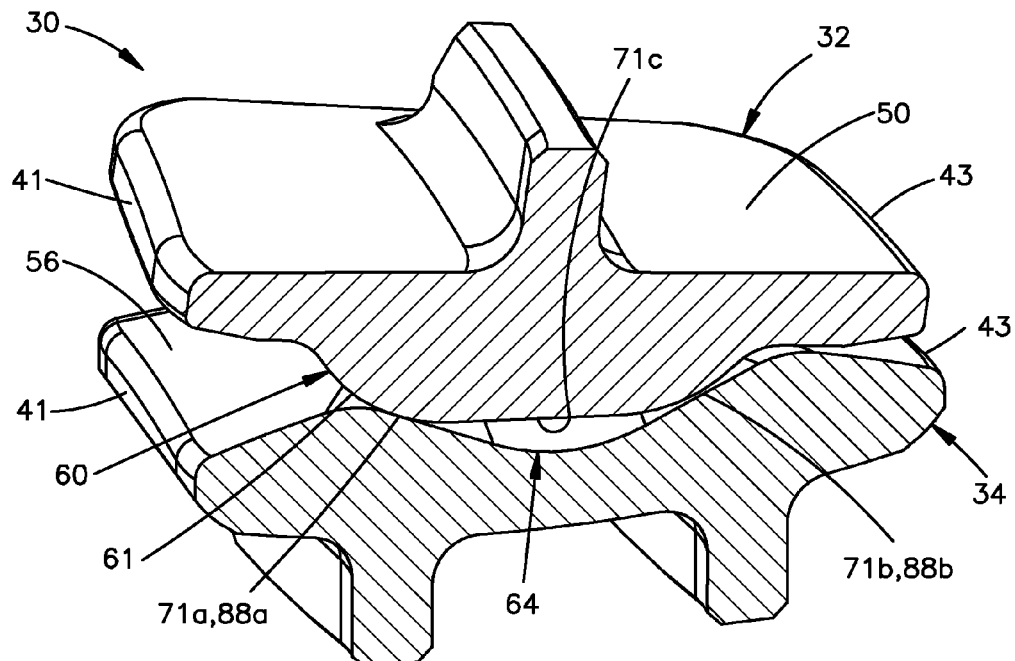
FIG. 7C is a rear elevation view of the intervertebral implant illustrated in FIG. 7A.
Figure 7D:
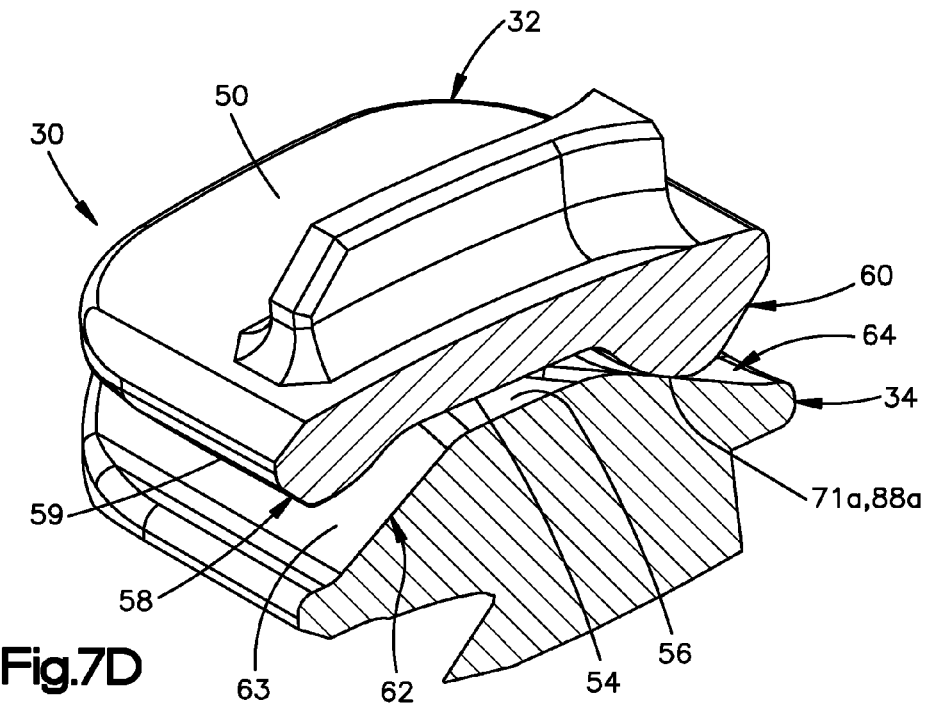
FIG. 7D is a cross-sectional view of the intervertebral implant illustrated in FIG. 7A, taken at midline 7D-7D.
Figure 7E:
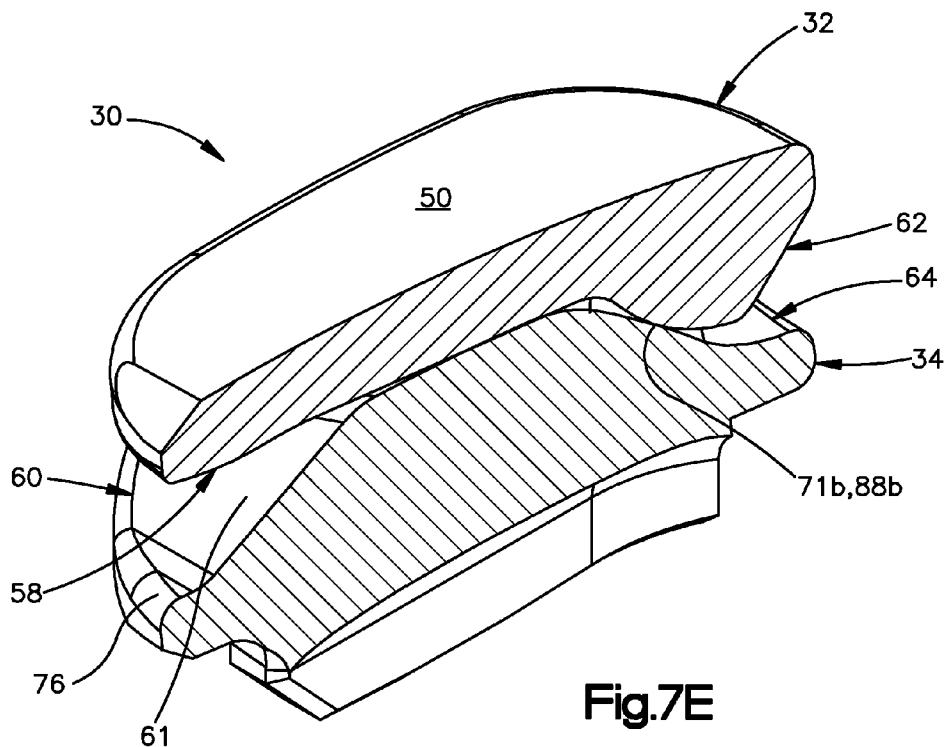
FIG. 7E is a cross-sectional view of the intervertebral implant illustrated in FIG. 7A, taken at line 7E-7E.
Figure 7F:
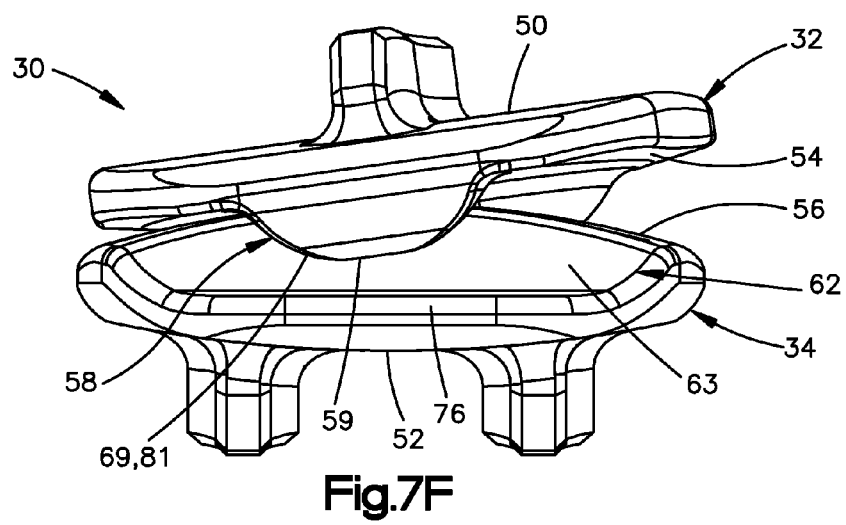
FIG. 7F is a cross-sectional view of the intervertebral implant illustrated in FIG. 7A, taken at line 7F-7F.
Figure 7G:
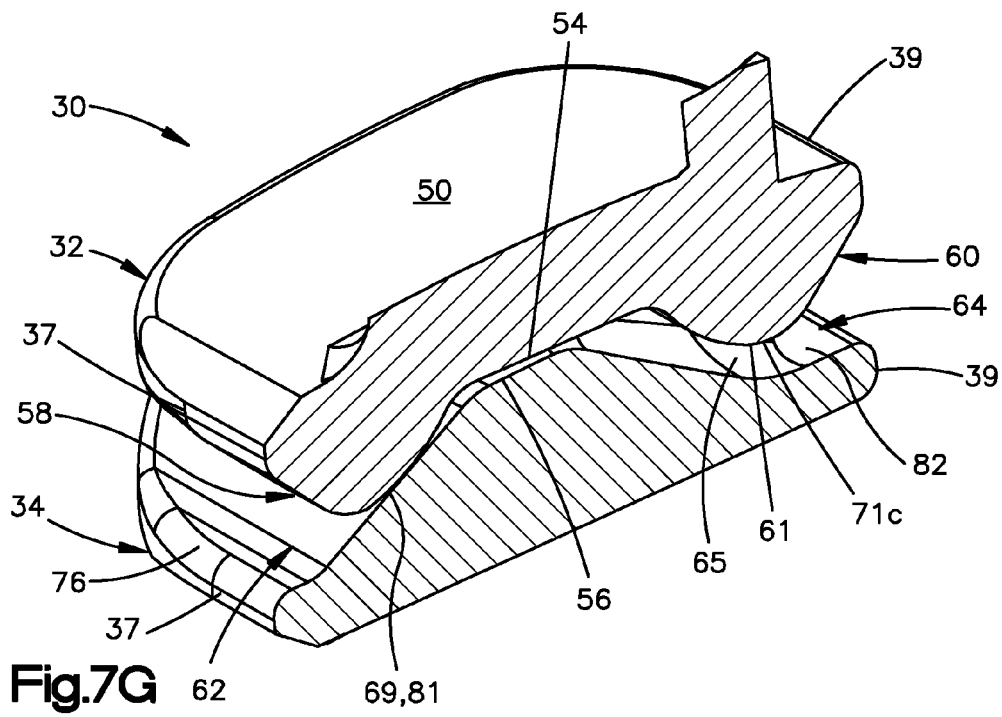
FIG. 7G is a cross-sectional view of the intervertebral implant illustrated in FIG. 7A, taken at line 7G-7G.
Figure 7H:
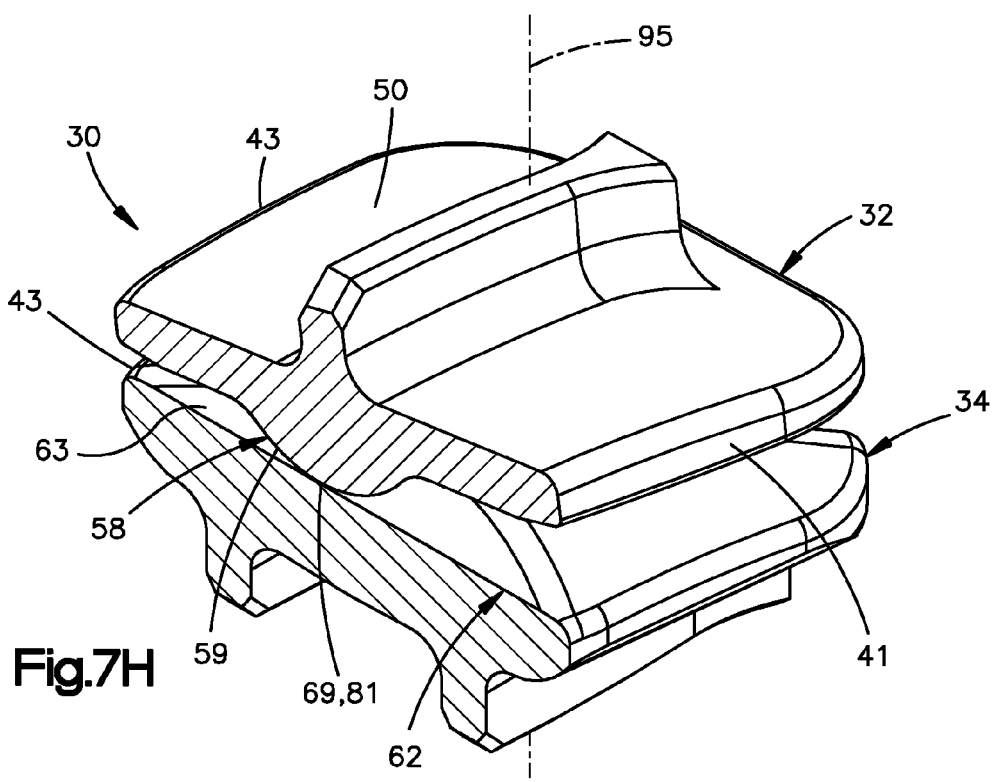
FIG. 7H is a cross-sectional view of the intervertebral implant illustrated in FIG. 7A, taken at line 7H-7H.
Figure 8A:
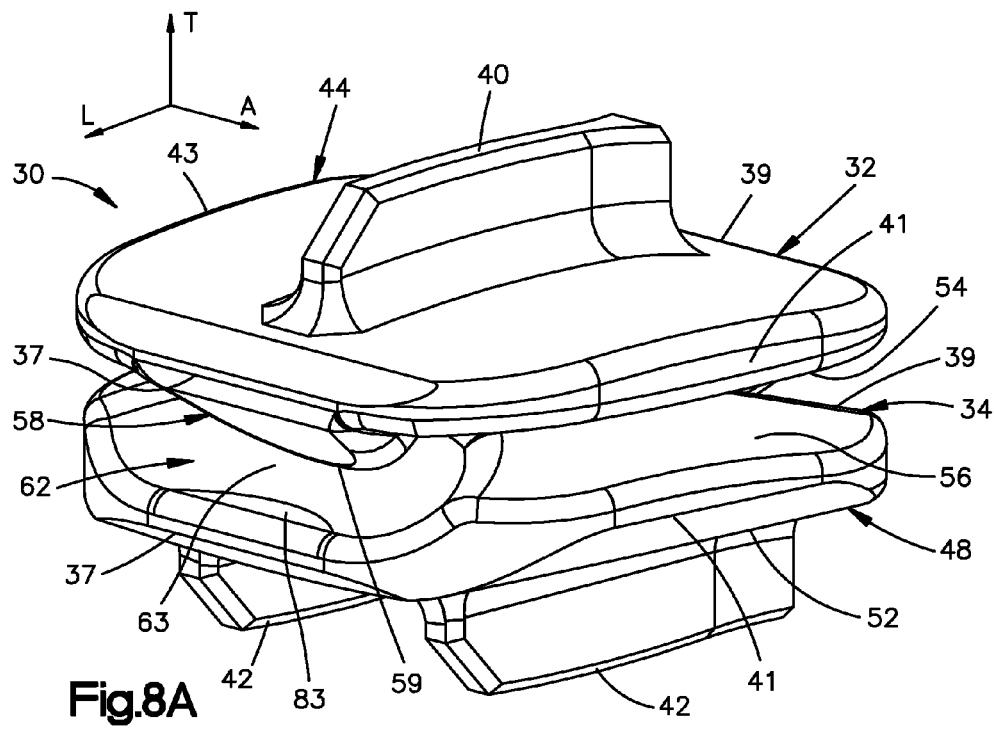
FIG. 8A is a top perspective view of an intervertebral implant similar to the intervertebral implant illustrated in FIG. 1C, but constructed in accordance with an alternative embodiment, including an upper endplate and a lower endplate.
Figure 8B:
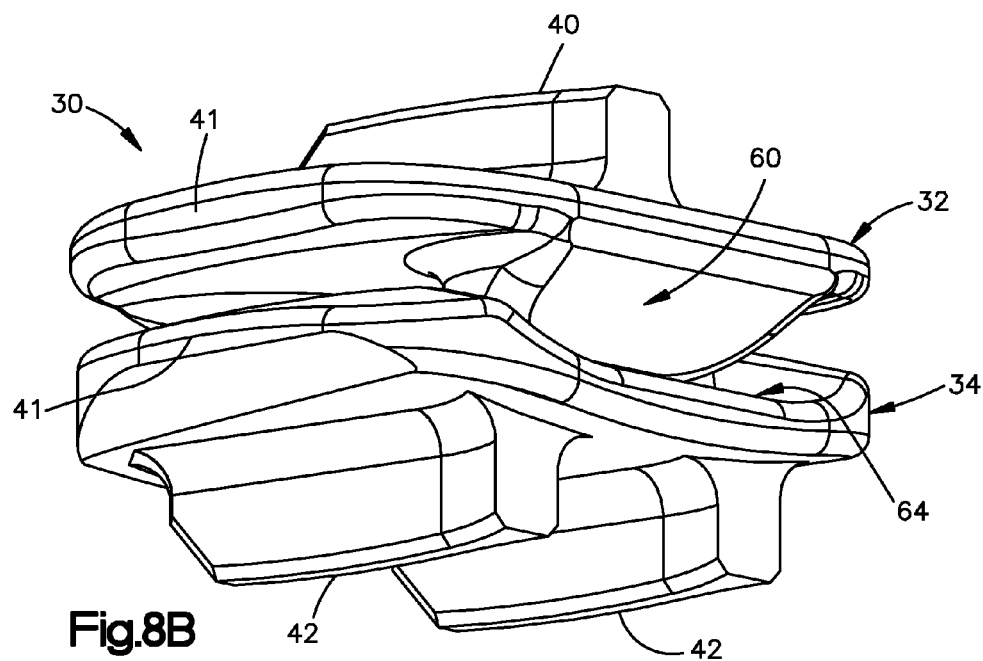
FIG. 8B is a bottom perspective view of the intervertebral implant illustrated in FIG. 8A.
Figure 8C:
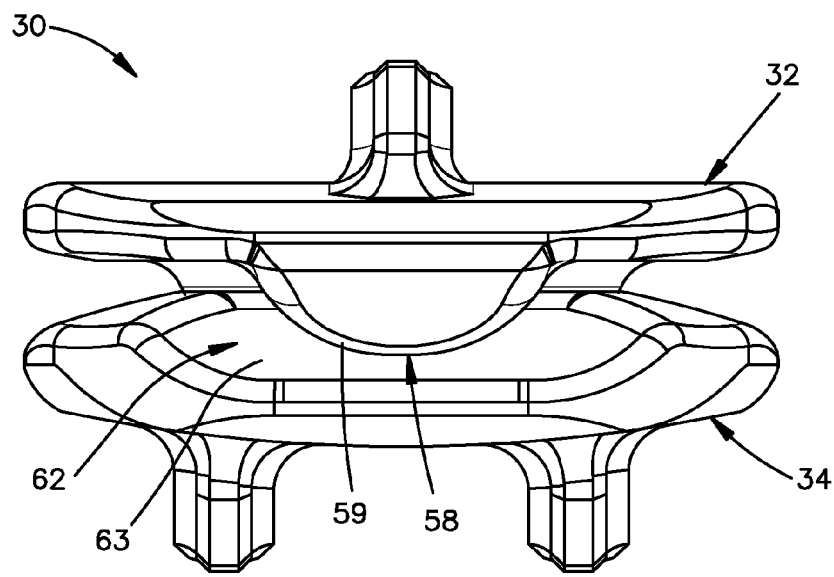
FIG. 8C is a front elevation view of the intervertebral implant illustrated in FIG. 8A.
Figure 8D:
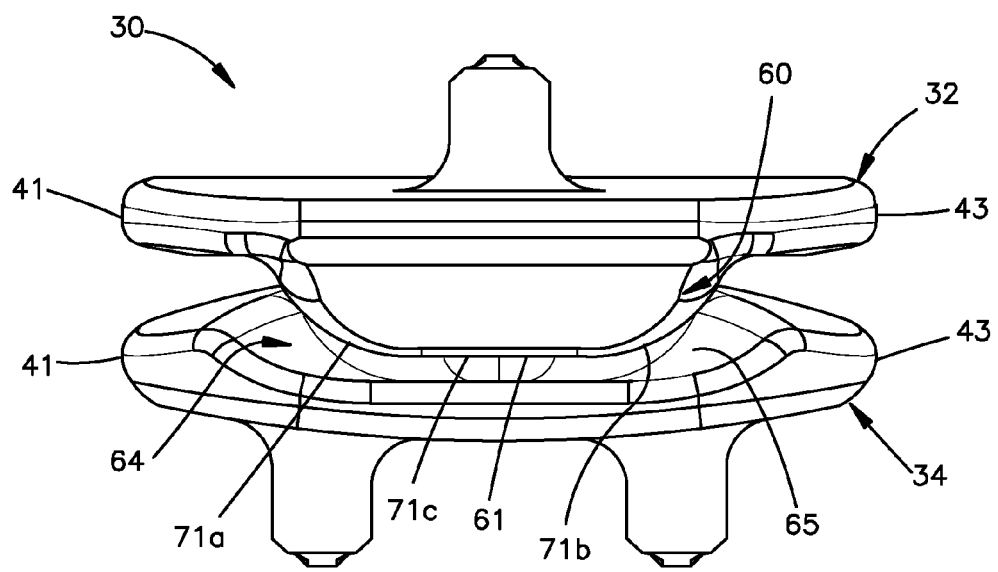
FIG. 8D is a rear elevation view of the intervertebral implant illustrated in FIG. 8A.

Referring also to FIGS. 7F-H, as the first contact location 71a moves forward along the longitudinal direction L and the second contact location 71b moves rearward along the longitudinal direction L, the first endplate 32, and in particular the rear end 39 of the first endplate 32, rotates about a transverse axis 95 that extends along a direction substantially parallel to the central transverse axis 55. As the first endplate 32 rotates about the axis 95, the contact location 69 of the first articulation member 58 translates along the contact location 81 that is defined by the third articulation surface 63. In accordance with the illustrated embodiment, the contact location 69, and thus the front end 37 of the first endplate 32, translates along a direction that includes a lateral directional component, the lateral directional component being directed toward the side 41 or 43 that is located closest to the contact location 71a or 71b that moves rearward along the longitudinal direction L during axial rotation. Otherwise stated, the contact location 69 travels along the first articulation surface 59 in the lateral direction A toward the one of the contact locations 71a-b that travels rearward during axial rotation. When the first endplate 32 articulates about the clockwise direction 93, the contact location 69 travels along the lateral direction A toward the second side wall 43 and the second contact location 71b. Furthermore, the contact location 69 pivots with respect to the contact location 81 as the first endplate 32 angulates with respect to the second endplate 34 along the clockwise direction 93, such that the contact location 69 travels along the third articulation surface 63. Because the first endplate 32 is driven to laterally bend as it axially rotates, the first endplate 32 is configured to articulate the superior vertebra 22a to undergo a combined motion of axially rotatation and lateral bending substantially along the facet joint plane, as opposed undergoing pure axial rotation, which could cause the facets of the adjacent vertebrae 22*a-b* to move toward each other and possibly into contact with each other.

It should be appreciated that axial rotation of the first endplate 32 relative to the second endplate 34 along the counterclockwise direction 98 is symmetrical with respect to axial rotation of the first endplate 32 relative to the second endplate 34 along the clockwise direction. Accordingly, while the first contact location 71*a* travels up and forward along the first contact location 88*a* and the second contact location 71*b* travels down and rearward along the second contact location 88*b* during clockwise rotation, the first contact location 71*a* travels down and rearward along the first contact location 88*a* and the second contact location 71*b* travels up and forward along the second contact location 88*b* during counterclockwise rotation. Furthermore, because the contact location 69 travels along the lateral direction A toward the one of the contact locations 71*a-b* that travels rearward during lateral bending, the contact location 69 travels along the lateral direction A toward the first contact location 71*a* during counterclockwise rotation.

During axial rotation, the inner surface 54 of the first endplate 32 is spaced from, for instance above, the second endplate 34, and in particular the inner surface 56 of the second endplate 34, along the transverse direction T. Furthermore, during axial rotation, the first articulation member 58 is spaced from, for instance above, the second endplate 34, and in particular the third articulation member 62 of the second endplate 34, at all regions with the exception of the contact location 69. Further still, during axial rotation, the second articulation member 60 is spaced from, for instance above, the second endplate 34, and in particular the fourth articulation member 64 of the second endplate 34, at all regions with the exception of the first and second contact locations 71*a-b*. Thus, during axial rotation, the first endplate 32 contacts the second endplate only at three points of contact that are defined by the contact locations 69 and 71*a-b*.

The first endplate 32 can be configured to articulate about the clockwise and counterclockwise axes 92 and 94, respectively, until the inner surface 54 of the first endplate 32 contacts the inner surface 56 of the second endplate due to the induced lateral bending, thereby providing a mechanical interference that defines the outer boundary of lateral bending. It should be appreciated that the first endplate 32 is configured to articulate forward and rearward along the concave path of motion 90, and is configured to articulate along the clockwise and counterclockwise directions 92 and 94 along the convex path of motion 96, and is further configured to axially rotate about the transverse axis 95, both alone and in combination with each other.

It should be appreciated that the first articulation surface 61 defines a guide for the first articulation surface 59 to travel along the third articulation surface 63 as described above during flexion-extension, lateral bending, axial rotation, and combinations of two or more thereof. Further, the first and second contact locations 88*a* and 88*b* define respective guides for the first and second contact locations 71*a* and 71*b* to travel along the fourth articulation surface 65 as described above during flexion-extension, lateral bending, axial rotation, and combinations of two or more thereof.

As described above, it is recognized that the size and shape of the first, second, third, and fourth articulation members 58, 60, 62, and 64, respectively, can be constructed in accordance with any suitable alternative embodiment. For instance, as illustrated in FIGS. 8A-10E, the third and fourth articulation members 62 and 64 can be constructed in accordance with an alternative embodiment, and the first and second articulation members 58 and 60 can be constructed substantially as described above, but dimensioned so as to articulate along the third and fourth articulation members 62 and 64 in the manner described above.

Figure 9A:
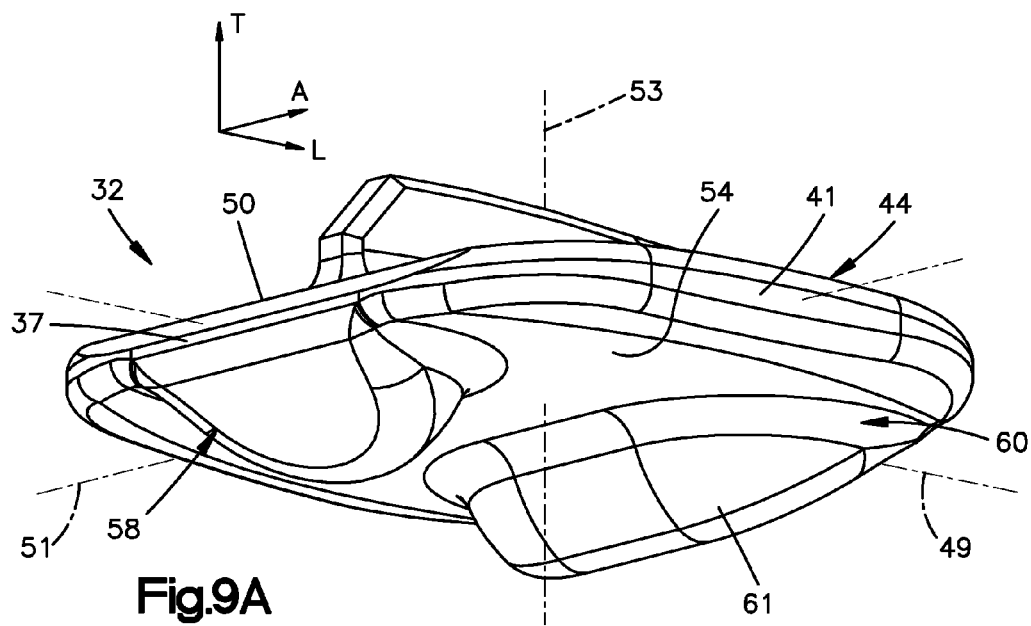
FIG. 9A is a bottom perspective view of the upper endplate of the intervertebral implant illustrated in FIG. 8A, including respective first and second articulation members.
Figure 9B:
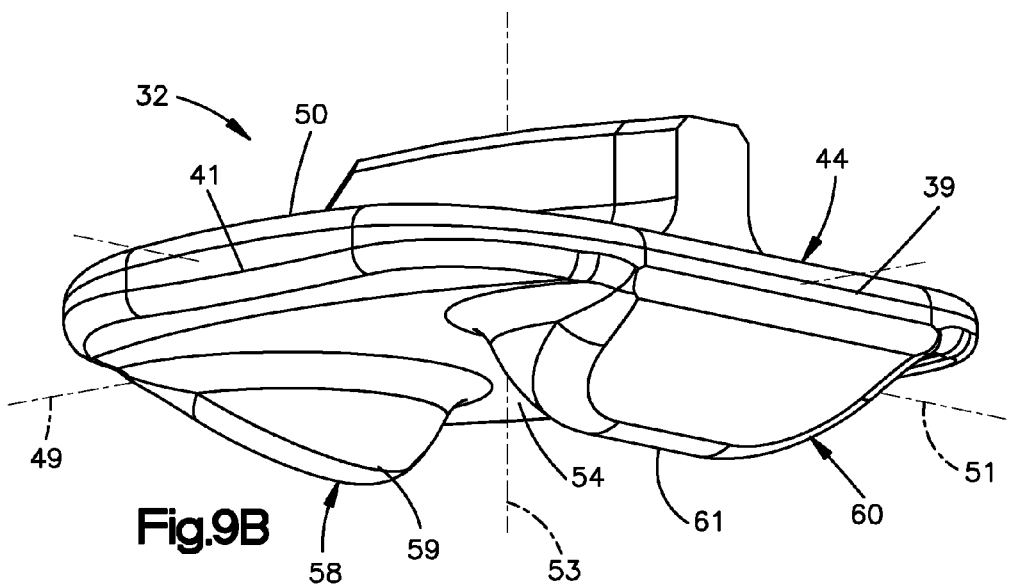
FIG. 9B is another bottom perspective view of the upper endplate of the intervertebral implant illustrated in FIG. 8A.
Figure 9C:
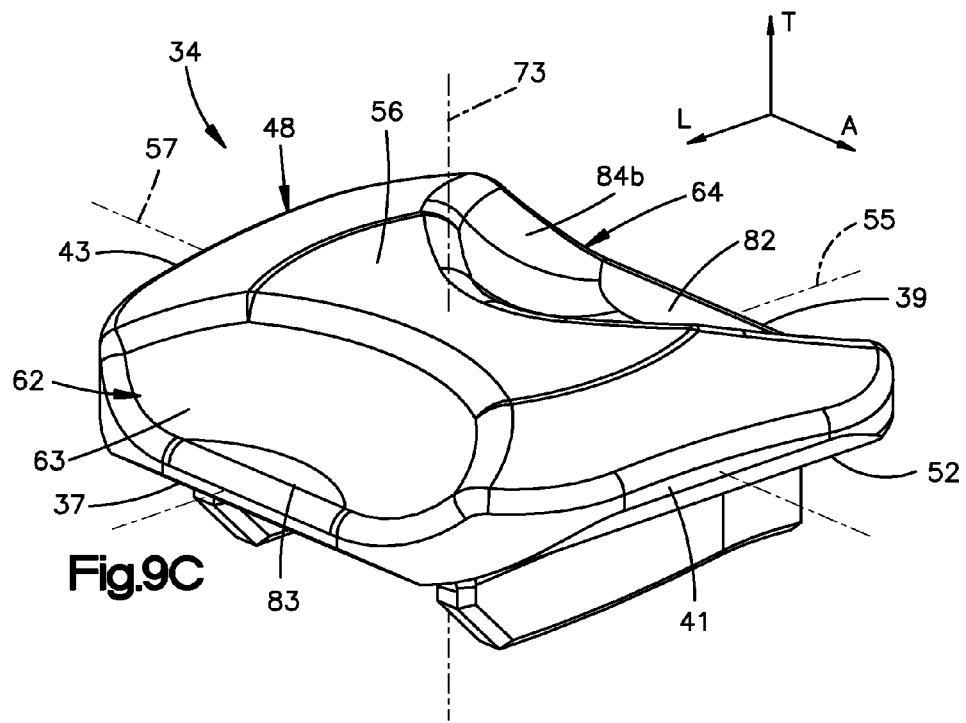
FIG. 9C is a top perspective view of the lower endplate of the intervertebral implant illustrated in FIG. 8A, including respective third and fourth articulation members.
Figure 9D:
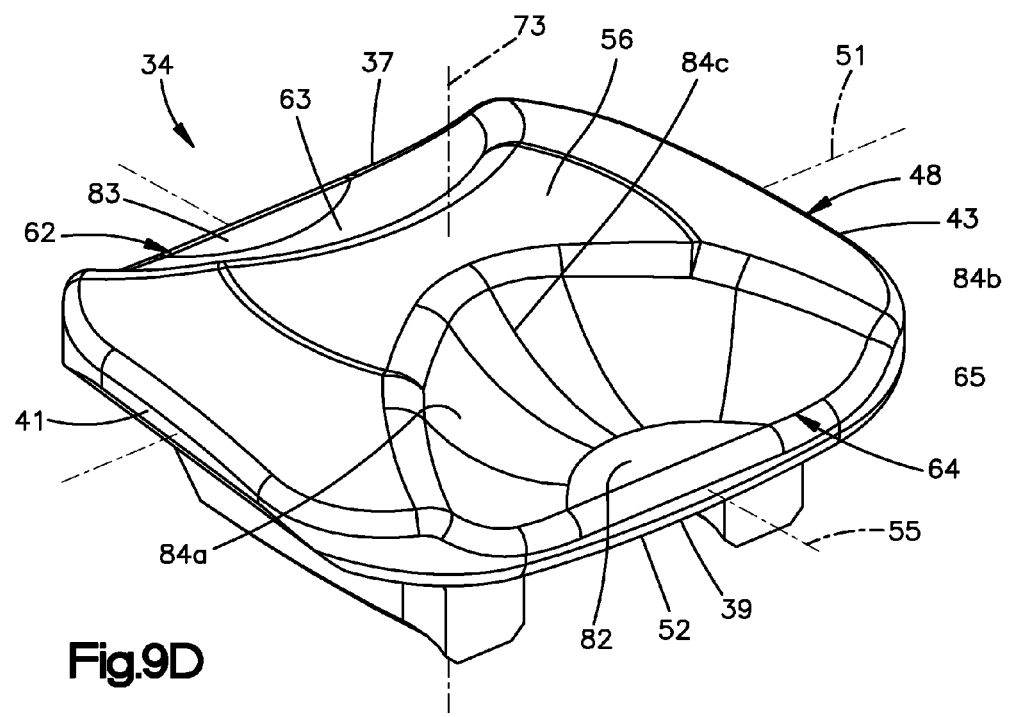
FIG. 9D is another top perspective view of the lower endplate of the intervertebral implant illustrated in FIG. 8A.
Figure 10A:
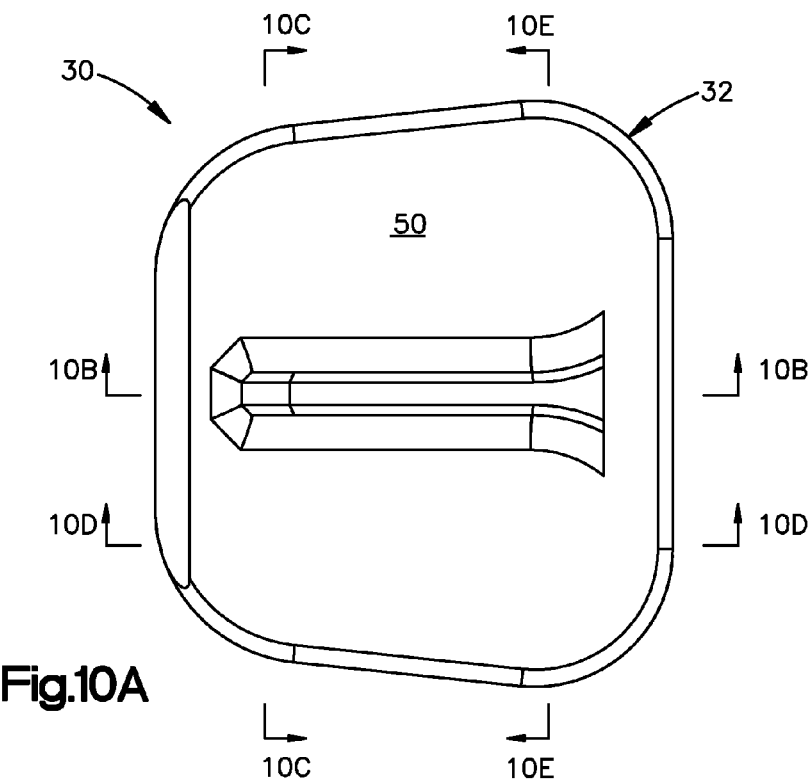
FIG. 10A is a top plan view of the intervertebral implant illustrated in FIG. 8A, shown in a neutral position.
Figure 10B:
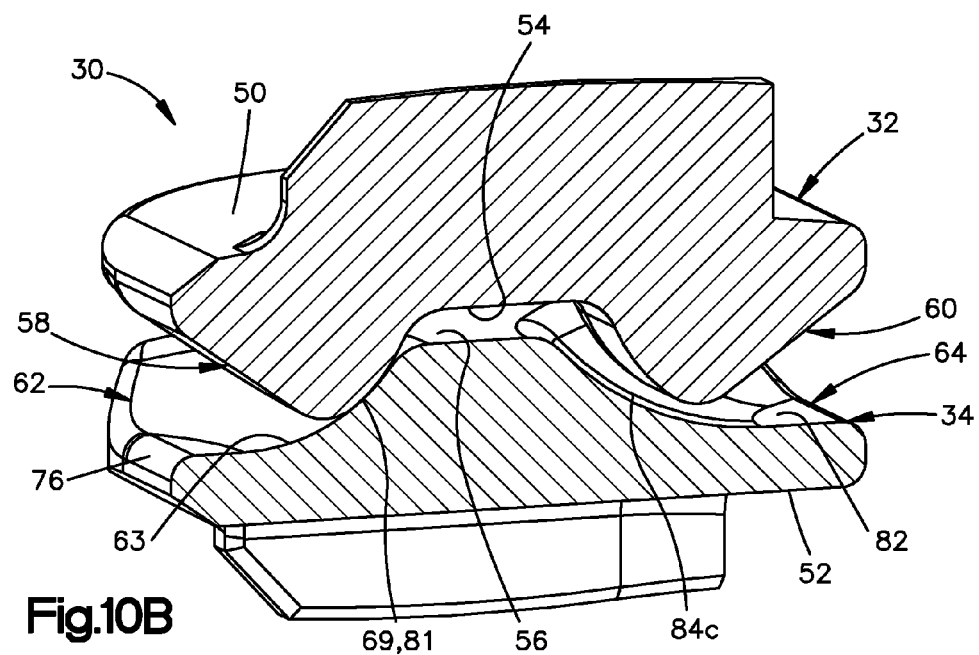
FIG. 10B is a cross-sectional view of the intervertebral implant illustrated in FIG. 10A, taken at medial-lateral midline 10B-10B.
Figure 10C:
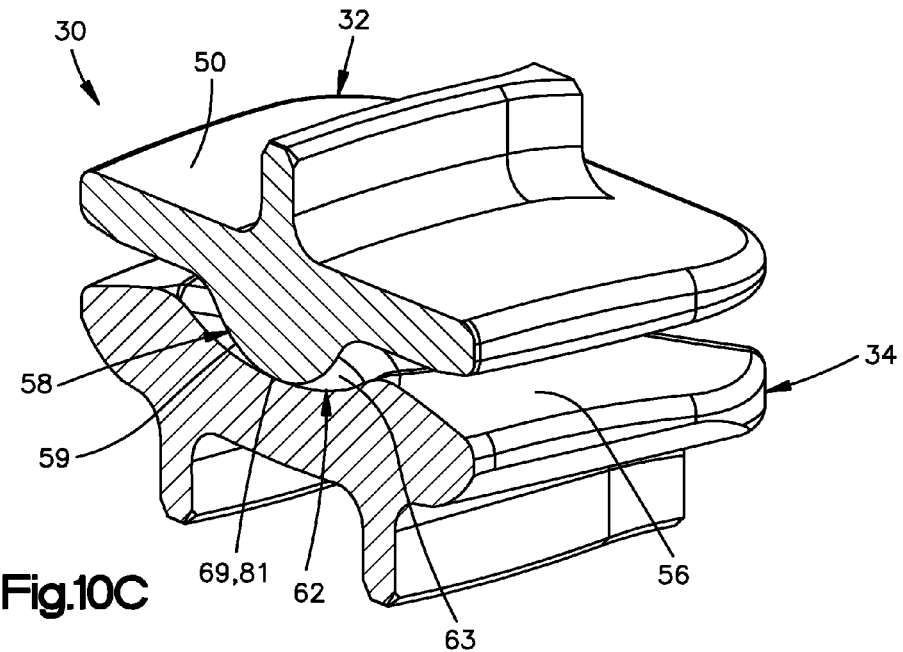
FIG. 10C is a cross-sectional view of the intervertebral implant illustrated in FIG. 10A, taken at line 10C-10C.
Figure 10D:
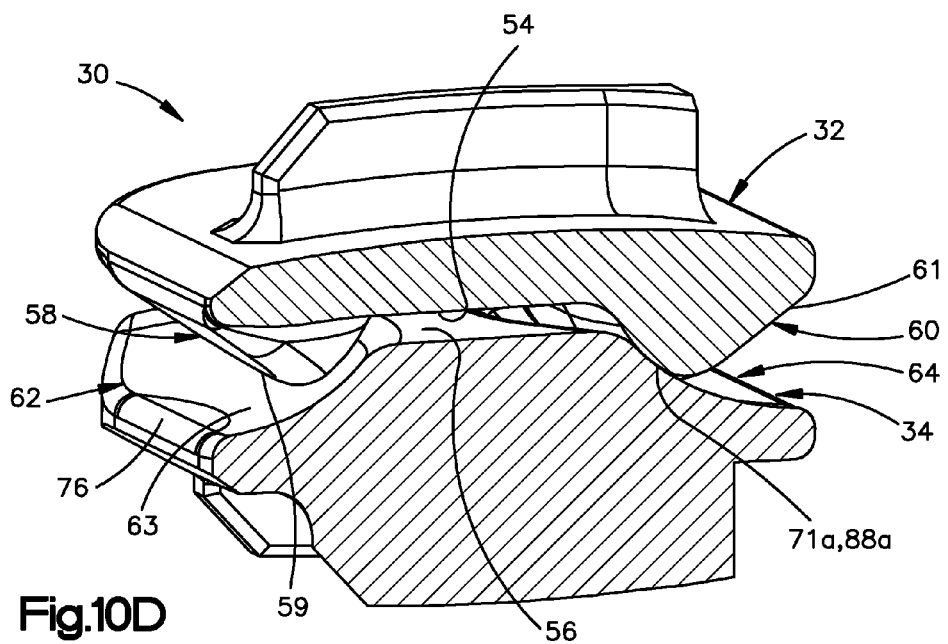
FIG. 10D is a cross-sectional view of the intervertebral implant illustrated in FIG. 10A, taken at line 10D-10D.
Figure 10E:
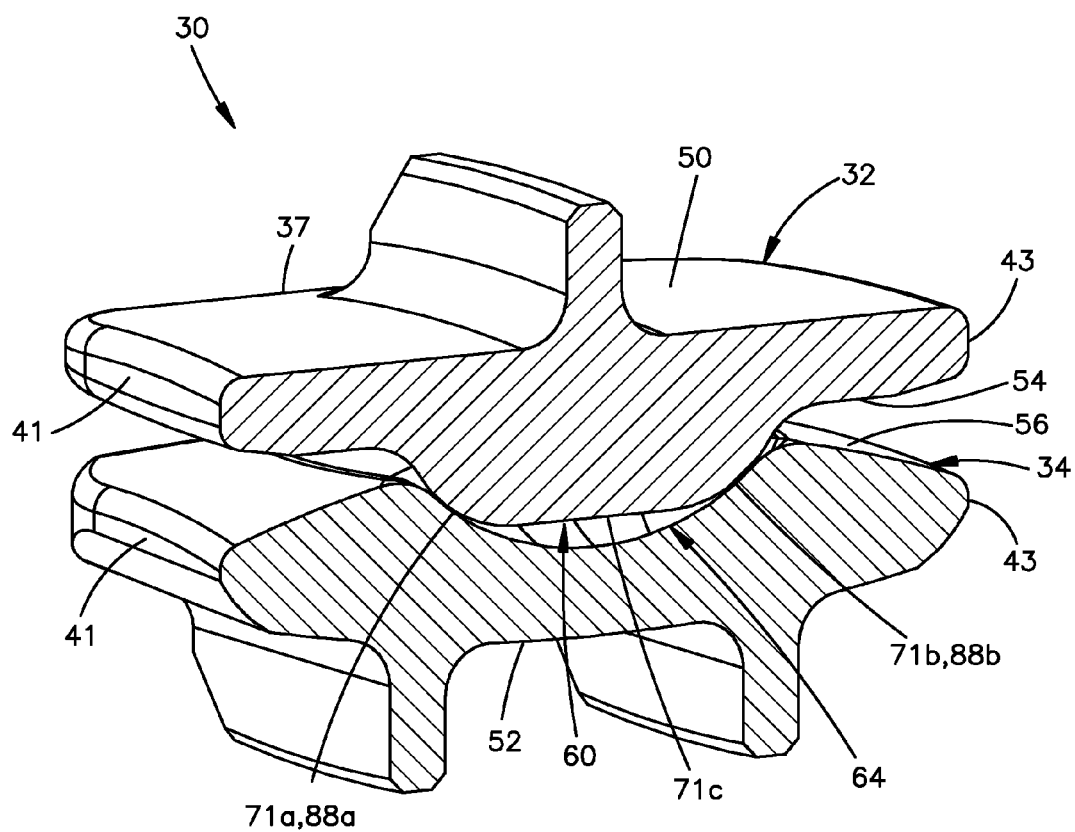
FIG. 10E is a cross-sectional view of the intervertebral implant illustrated in FIG. 10A, taken at line 10E-10E.

Referring in particular to FIGS. 9C-D, the third articulation member 62 can be captured between the first and second sides 41 and 43 of the second endplate 34. For instance, the third articulation surface 63 can be curved up along the transverse direction T along a concave path as it extends rearward along the longitudinal direction L. Further, the third articulation surface 63 can be curved up along the transverse direction T along a concave path as it extends outward along the lateral direction A away from the central longitudinal axis 49. The third articulation member 62 can further define a base 83 that extends from the bottom end of the third articulation surface 63 substantially along a plane defined by the longitudinal and lateral directions L and A. Thus, the base 83 can define a stop member that defines a boundary for forward articulation, or flexion, of the first endplate 32 relative to the second endplate 34.

Furthermore, the side walls 84*a* and 84*b* of the fourth articulation member 64 can be curved along a concave path as they extend along the longitudinal direction L between the inner surface 56 and the base 82. Furthermore, while the junction 84*c* can be disposed forward of the central lateral axis 57 as illustrated in FIGS. 2C-D, the junction 84*c* can alternatively be disposed rearward of the central lateral axis 57 as illustrated in FIGS. 9C-D. Moreover, as illustrated in FIGS. 9C-D, the first and second side walls 84*a-b* and the junction 84*c* can define a longitudinally forward perimeter of the fourth articulation member that has a substantially constant radius of curvature. Thus, the side walls 84*a-b* and the junction 84*c* can combine to define a portion of an ellipsoid or a spheroid as desired.

Figure 11A:
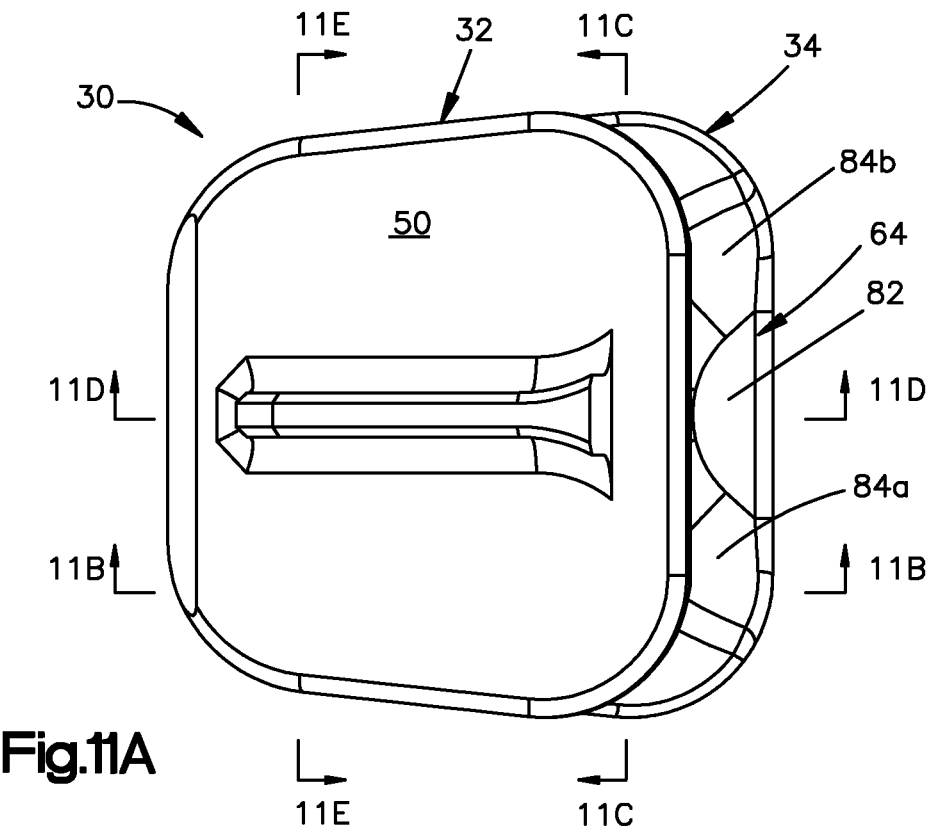
FIG. 11A is a perspective view of the intervertebral implant illustrated in FIG. 8A, but showing the upper endplate articulated anteriorly with respect to the lower endplate, during flexion.
Figure 11B:
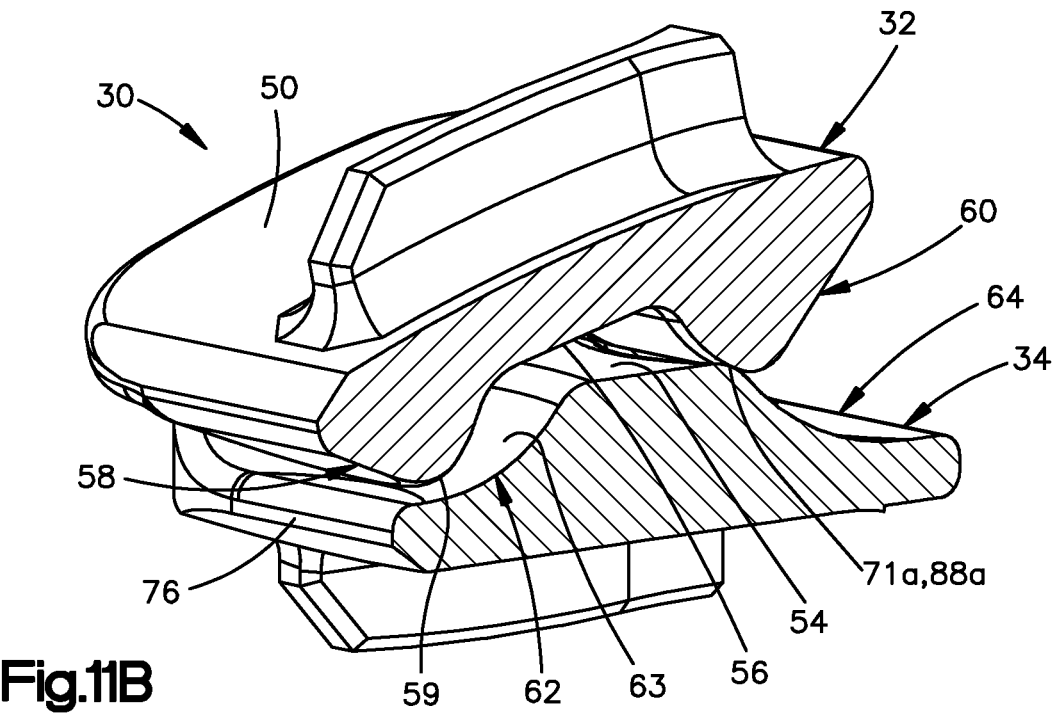
FIG. 11B is a cross-sectional view of the intervertebral implant illustrated in FIG. 11A, taken at line 11B-11B.
Figure 11C:
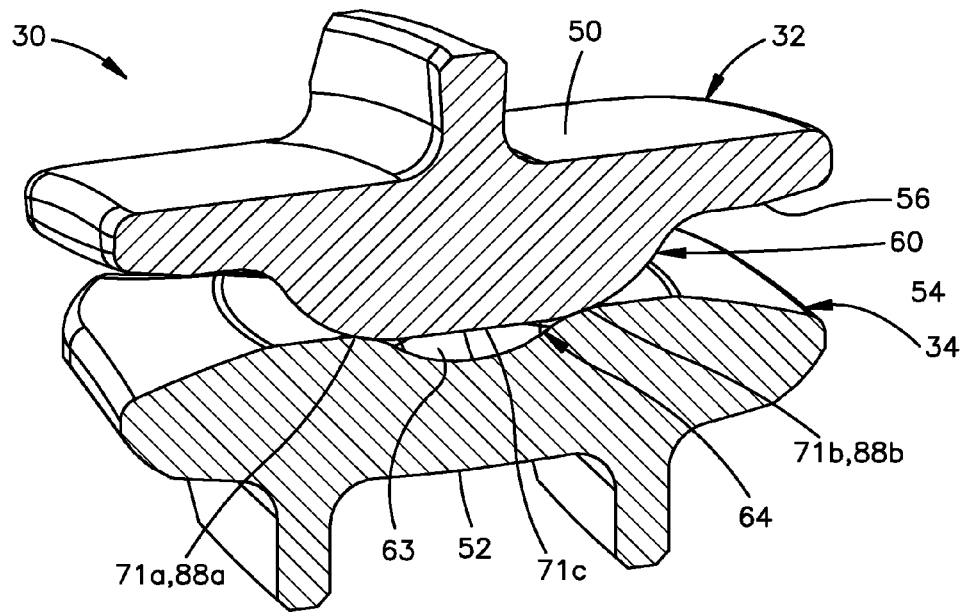
FIG. 11C is a cross-sectional view of the intervertebral implant illustrated in FIG. 11A, taken at line 11C-11C.

Thus, as illustrated in FIGS. 11A-C, during flexion, or forward movement of the first endplate 32 with respect to the second endplate 34 along the longitudinal direction L, the first and second contact locations 71*a* and 71*b* of the second articulation member 60 travel along the complementary first and second contact locations 88*a* and 88*b* of the fourth articulation member 64 in the forward longitudinal direction L as described above. However, because the first and second side walls 84*a-b* are curved upward along a concave path as they extend forward in the longitudinal direction L, the first and second contact locations 71*a-b*, and thus the rear end 39 of the first endplate 32, likewise travel upward along a concave path as they travel forward in the longitudinal direction L along the first and second contact locations 88*a-b*.

Figure 11D:
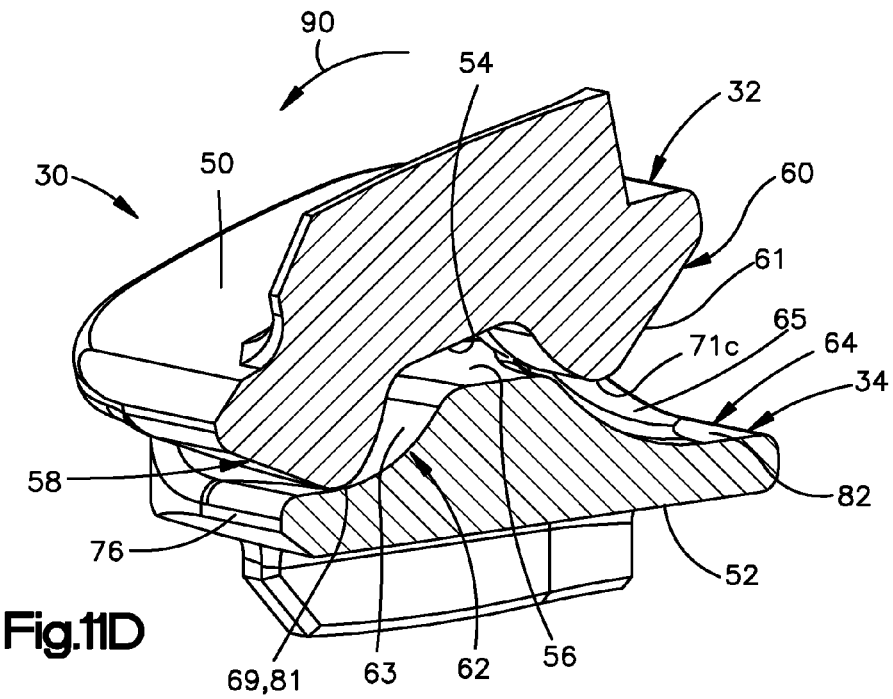
FIG. 11D is a cross-sectional view of the intervertebral implant illustrated in FIG. 11A, taken at medial-lateral line 11D-11D.
Figure 11E:
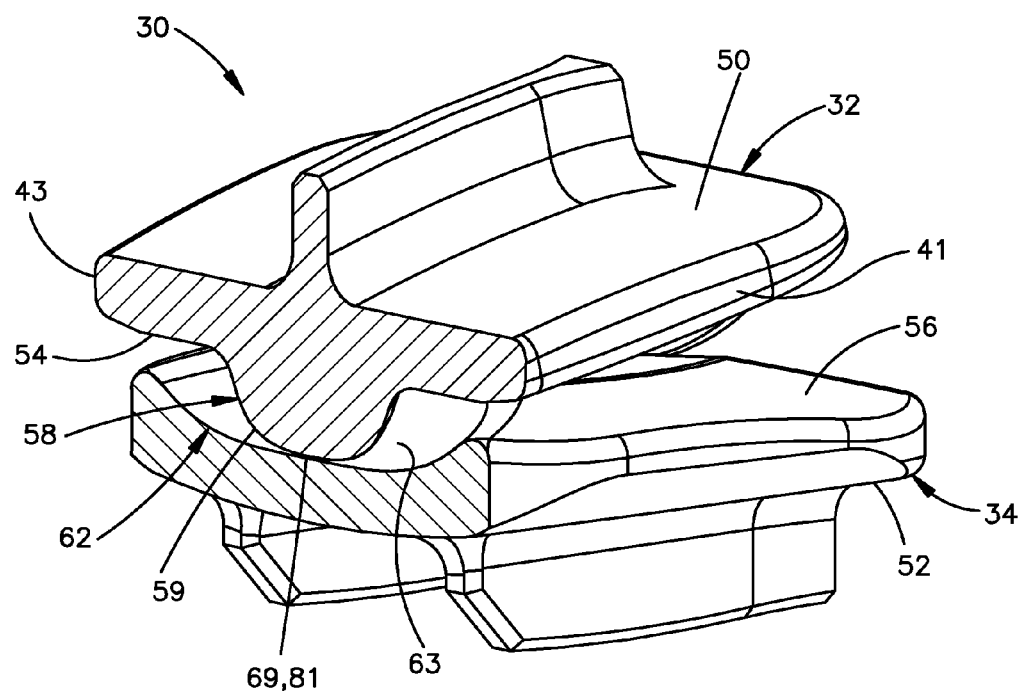
FIG. 11E is a cross-sectional view of the intervertebral implant illustrated in FIG. 11A, taken at line 11E-11E.

Referring also to FIGS. 11D-E, during flexion, as the first and second contact locations 71*a-b* travel forward along the longitudinal direction L and upward in the transverse direction T as they ride along the respective first and second contact locations 88*a-b*, the contact location 69 of the first articulation member 58 travels forward along the longitudinal direction L and downward along the transverse direction T as it rides along the contact location 81 defined by the third articulation member 62. Because the third articulation surface 63 is curved down along the transverse direction T as it extends forward along the longitudinal direction L so as to define a concave path, the contact location 69 of the first articulation member 58, and thus the front end 37 of the first endplate 32, likewise travels along a concave path downward along the transverse direction T as it travels forward in the longitudinal direction L. Because 1) the first and second contact locations 71*a* and 71*b*, and thus the rear end 39 of the first endplate 32, travel along a concave path as they travel up along the transverse direction T and forward along the longitudinal direction L, and 2) the contact location 69 of the first articulation member 58, and thus the front end 37 of the first endplate 32, travels down along a concave path as they travel down along the transverse direction T and forward along the longitudinal direction L, the first endplate 32, and in particular the outer surface 50, travels along the convex path of motion 90 that has a greater curvature than the convex path of motion defined when the third and fourth articulation surfaces extend substantially linearly along the transverse direction T as they extend along the longitudinal direction L.

Figure 12A:
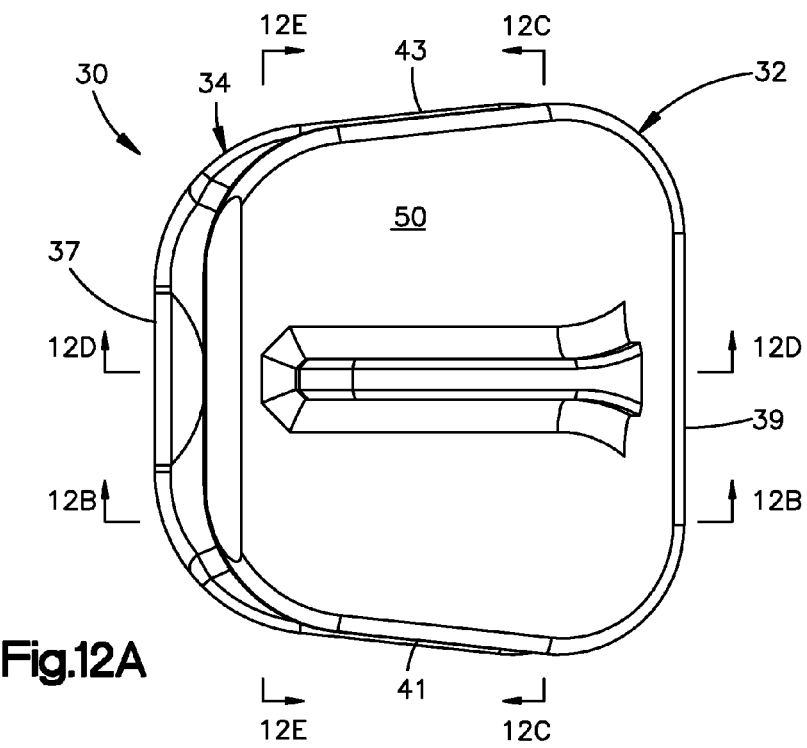
FIG. 12A is a perspective view of the intervertebral implant illustrated in FIG. 8A, but showing the upper endplate articulated posteriorly with respect to the lower endplate, during extension.
Figure 12B:
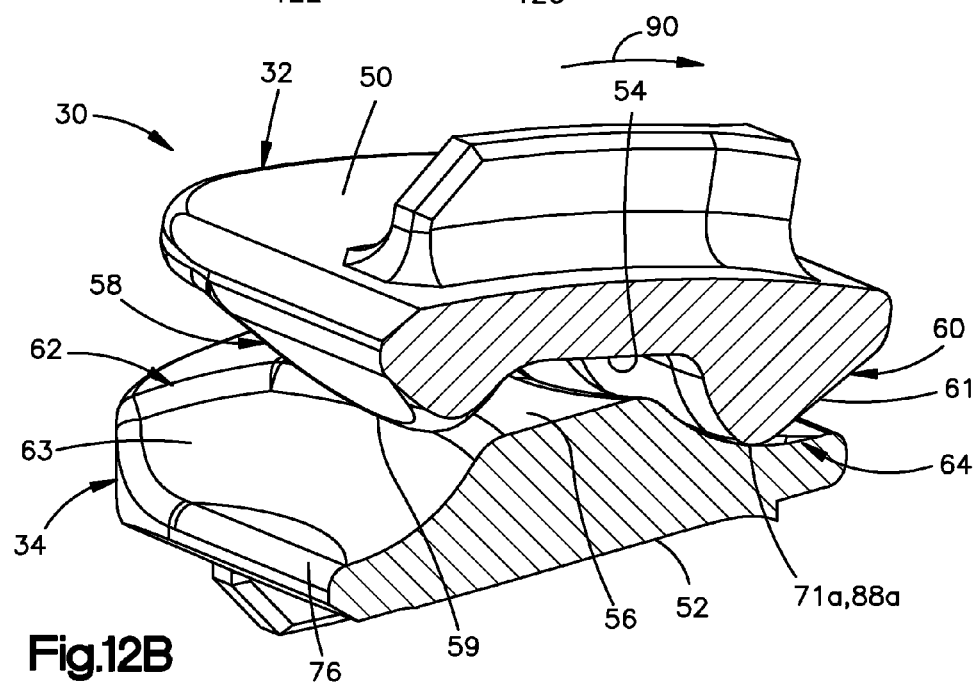
FIG. 12B is a cross-sectional view of the intervertebral implant illustrated in FIG. 12A, taken at line 12B-12B.
Figure 12C:
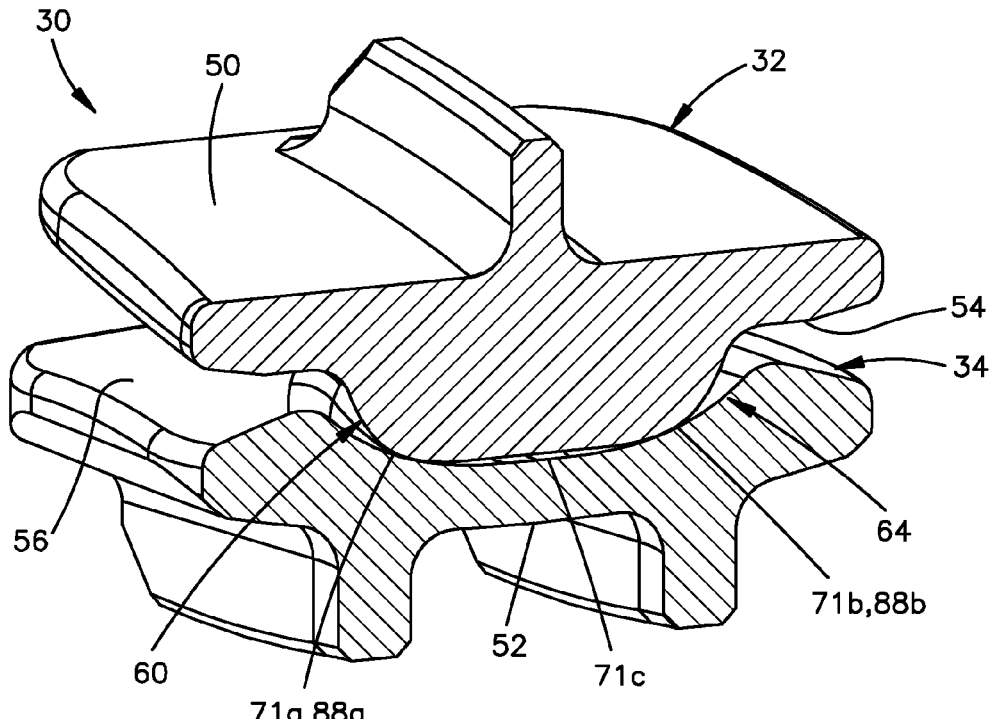
FIG. 12C is a cross-sectional view of the intervertebral implant illustrated in FIG. 12A, taken at line 12C-12C.

Thus, as illustrated in FIGS. 12A-C, during extension, or rearward movement of the first endplate 32 with respect to the second endplate 34 along the longitudinal direction L, the first and second contact locations 71a and 71b of the second articulation member 60 travel along the complementary first and second contact locations 88a and 88b of the fourth articulation member 64 in the forward longitudinal direction L as described above. However, because the first and second side walls 84a-b are curved down in the transverse direction along a concave path as they extend rearward in the longitudinal direction L, the first and second contact locations 71a-b, and thus the rear end 39 of the first endplate 32, likewise travel down along a concave path as they travel rearward in the longitudinal direction L along the first and second contact locations 88a-b.

Figure 12D:
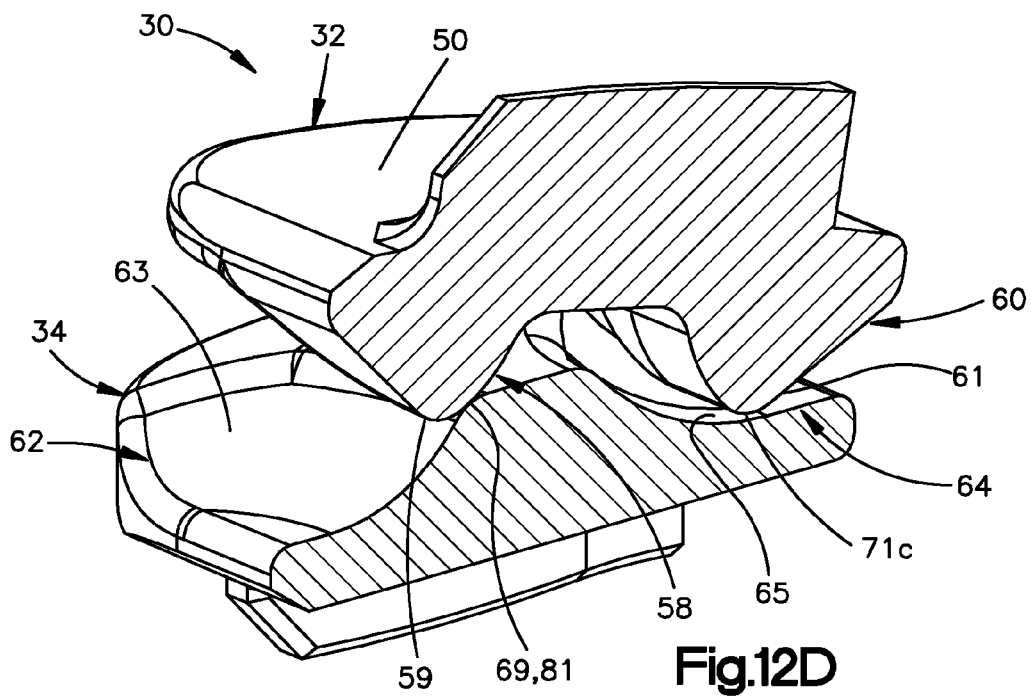
FIG. 12D is a cross-sectional view of the intervertebral implant illustrated in FIG. 12A, taken at medial-lateral midline 12D-12D.
Figure 12E:
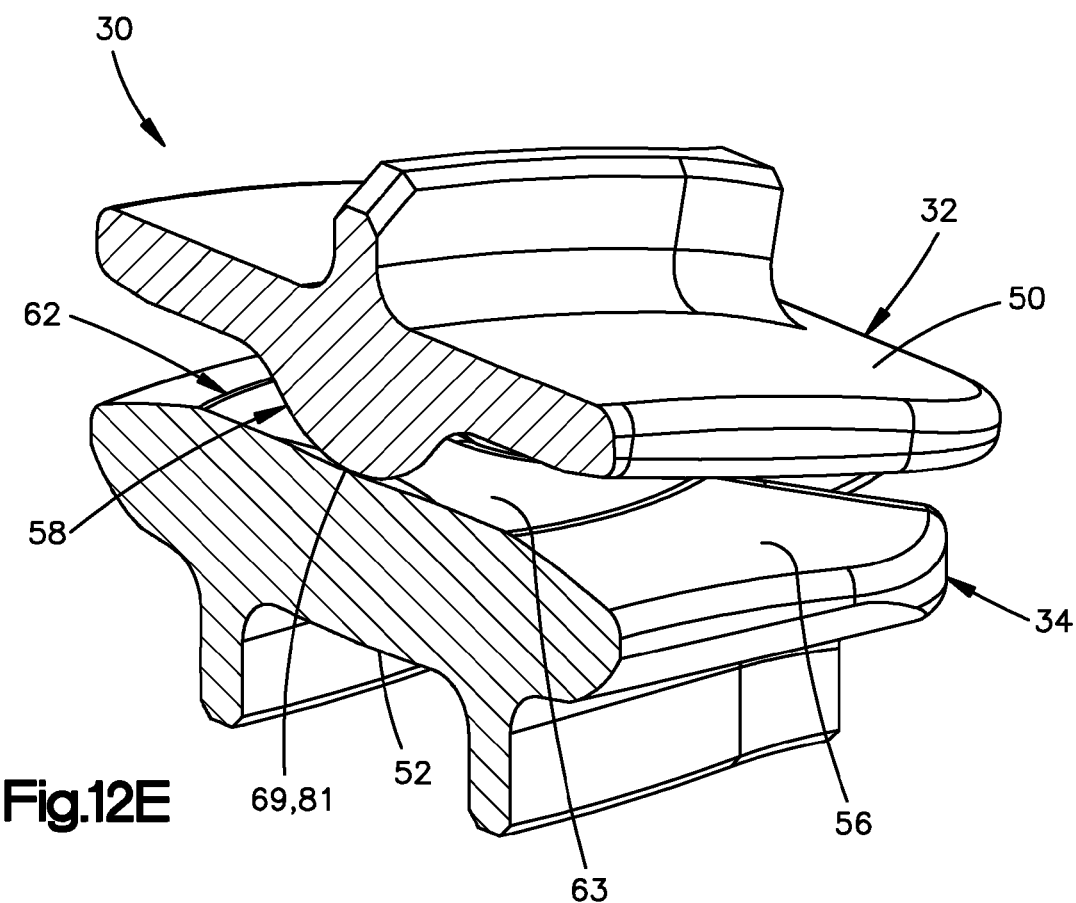
FIG. 12E is a cross-sectional view of the intervertebral implant illustrated in FIG. 12A, taken at line 12E-12E.
Figure 13A:
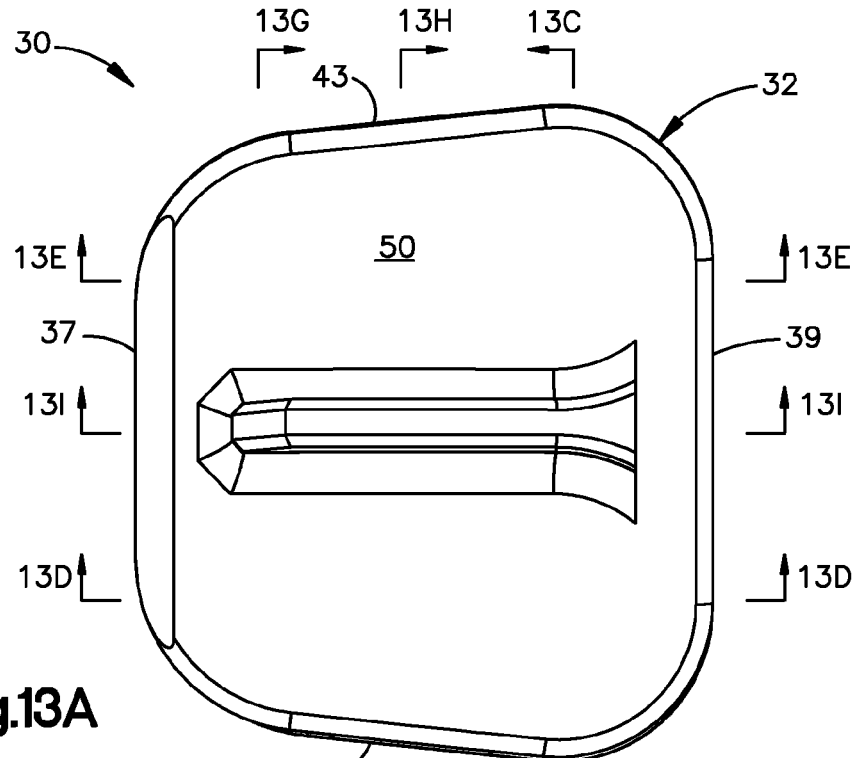
FIG. 13A is a top plan view of the intervertebral implant illustrated in FIG. 1B, but showing the upper endplate articulated laterally with respect to the lower endplate, during lateral bending.
Figure 13B:
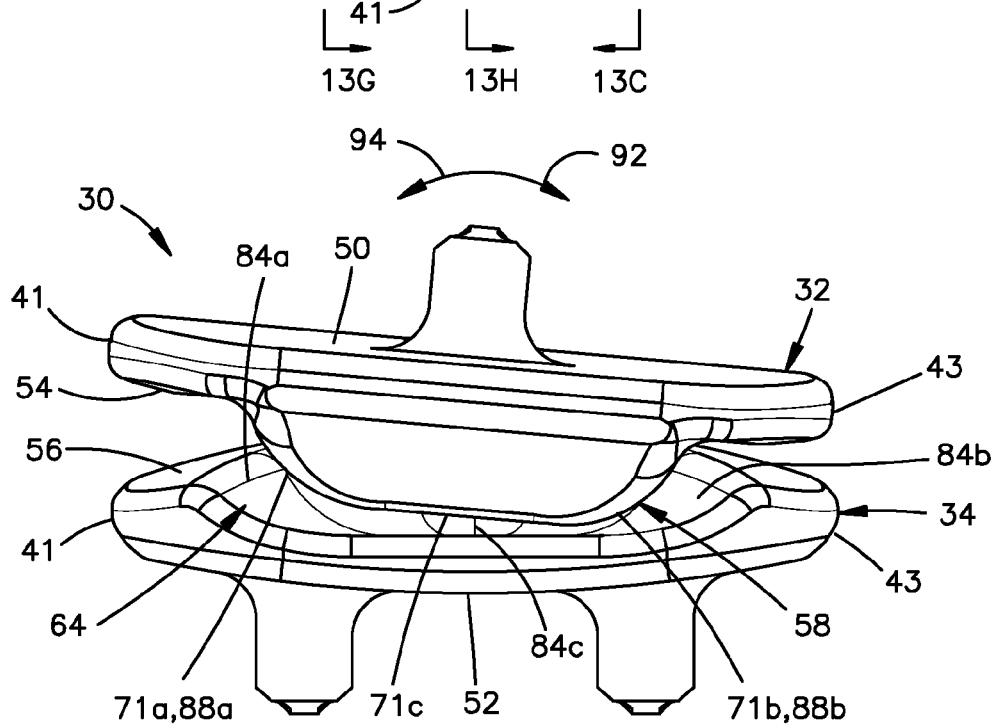
FIG. 13B is a rear elevation view of the intervertebral implant illustrated in FIG. 13A.
Figure 13G:
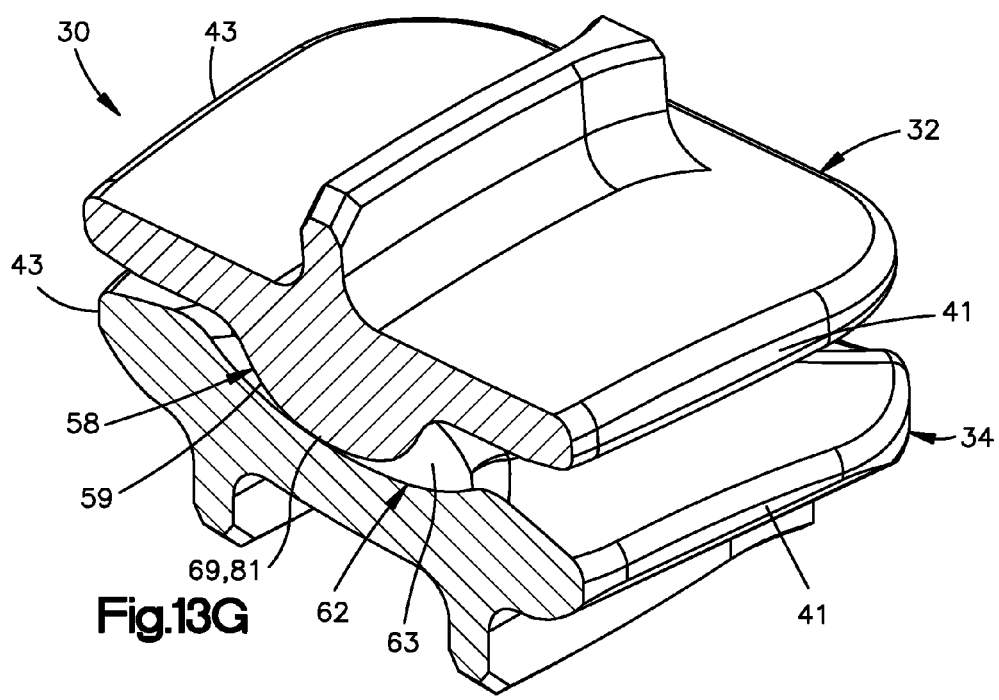
FIG. 13G is a cross-sectional view of the intervertebral implant illustrated in FIG. 13A, taken at line 13G-13G.
Figure 13H:
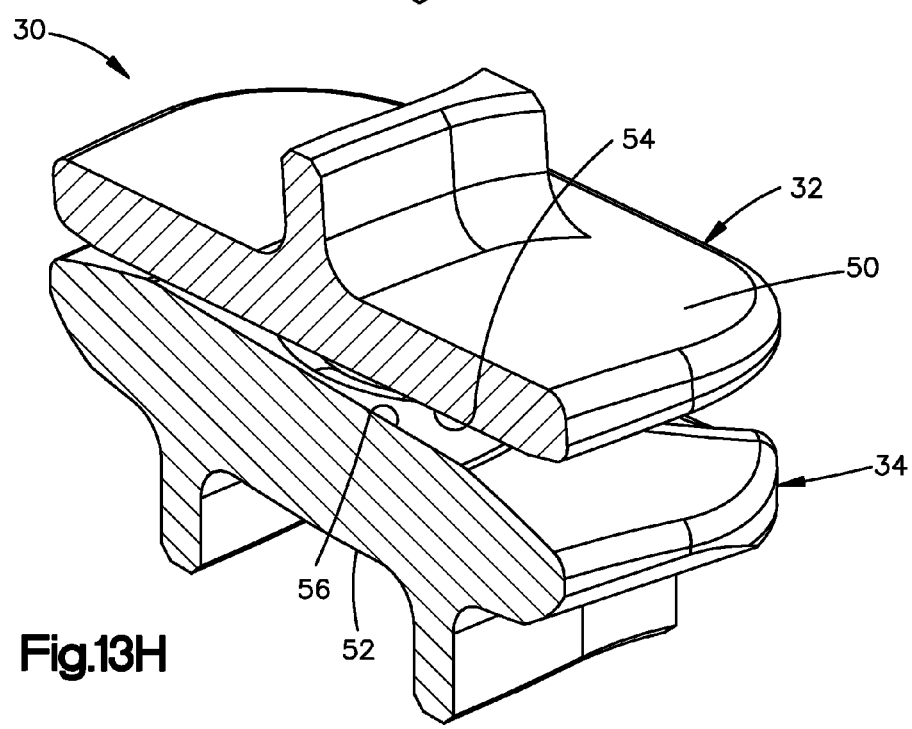
FIG. 13H is a cross-sectional view of the intervertebral implant illustrated in FIG. 13A, taken at anterior-posterior midline 13H-13H.
Figure 13I:
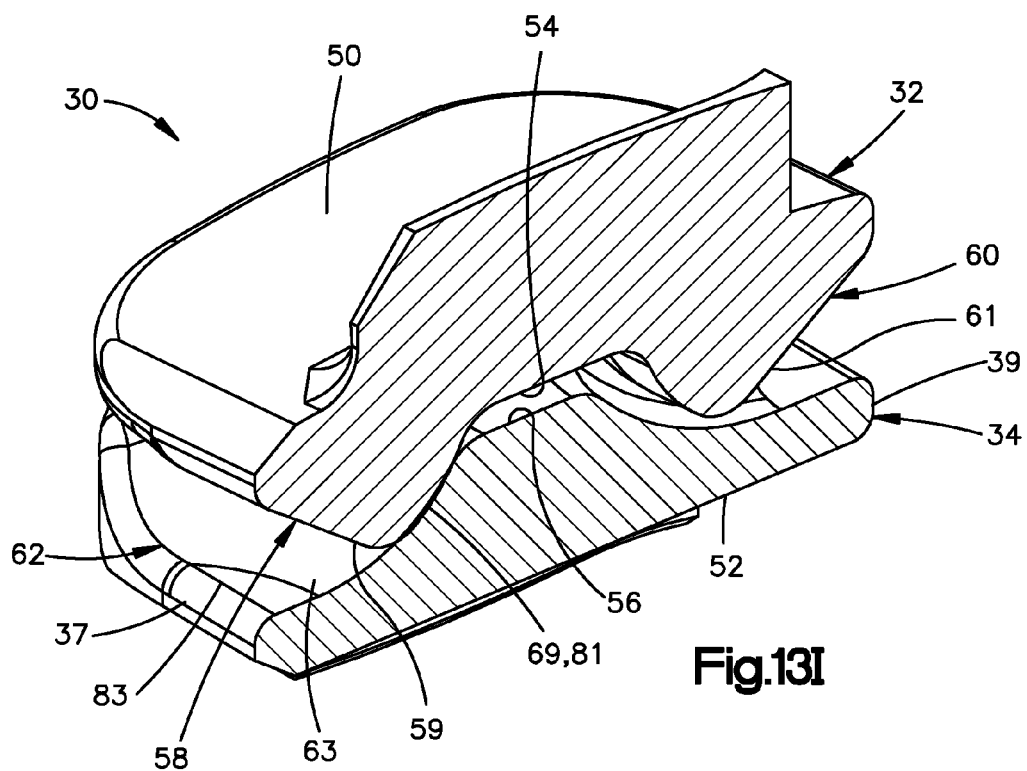
FIG. 13I is a cross-sectional view of the intervertebral implant illustrated in FIG. 13A, taken at medial-lateral midline 13I-13I.

Referring also to FIGS. 12D-E, during extension, as the first and second contact locations 71a-b travel rearward along the longitudinal direction L and downward in the transverse direction T as they ride along the respective first and second contact locations 88a-b, the contact location 69 of the first articulation member 58 travels rearward along the longitudinal direction L and up along the transverse direction T as it rides along the contact location 81 defined by the third articulation member 62. Because the third articulation surface 63 is curved upward along the transverse direction T as it extends rearward along the longitudinal direction L so as to define a concave path, the contact location 69 of the first articulation member 58, and thus the front end 37 of the first endplate 32, likewise travels along a concave path upward along the transverse direction T as it travels rearward in the longitudinal direction L. Thus, the first endplate 32, and in particular the outer surface 50, travels along the convex path of motion 90 that has a greater curvature than the convex path of motion defined when the third and fourth articulation surfaces extend substantially linearly along the transverse direction T as they extend along the longitudinal direction L.

Referring now to FIGS. 13A-I generally, the intervertebral implant 30 can induce axial rotation of the first endplate 32 during lateral bending of the first endplate 32 in the manner described above. Thus, during operation, the first and second articulation members 58 and 60 can ride along the third and fourth articulation members 62 and 64, respectively, such that rotation of the first endplate 32 about a first axis of rotation that is substantially perpendicular to the insertion direction induces rotation of the first endplate 32 about a second axis of rotation that is substantially perpendicular to the first axis of rotation. For instance, as illustrated in FIGS. 6A-E, during lateral bending, or rotational movement of the first endplate 32 with respect to the second endplate 34 about a longitudinal axis of rotation, one of the first and second contact locations 71a and 71b of the second articulation member 60 travels along the complementary first and second contact locations 88a and 88b of the fourth articulation member 64 along a first direction, and the other of the first and second contact locations 71a and 71b of the second articulation member 60 travels along the complementary first and second contact locations 88a and 88b of the fourth articulation member 64 along a second direction that is opposite the first direction. However, because the first and second contact locations 88a and 88b are curved along the transverse direction T as they extend between the inner surface 56 and the base 82 along the longitudinal direction L so as to define a concave path having a greater slope than when the first and second contact locations 88a and 88b extend substantially linearly as described above, the first and second contact locations 71a and 71b travel in the transverse direction T at greater rates than when the first and second contact locations 88a and 88b extend substantially linearly during lateral bending.

Referring also to FIGS. 13F-I, as the first contact location 71a moves forward along the longitudinal direction L and the second contact location 71b moves rearward along the longitudinal direction L, the first endplate 32 rotates about a transverse axis that extends substantially parallel to the central transverse axis 53. Furthermore, because the first and second contact locations 88a and 88b are curved along the transverse direction T as they extend between the inner surface 56 and the base 82 along the longitudinal direction L so as to define a concave path having a greater slope than when the first and second contact locations 88a and 88b extend substantially linearly as described above, the first and second contact locations 71a and 71b travel in the lateral direction A at slower rates than when the first and second contact locations 88a and 88b extend substantially linearly during the induced axial rotation. Thus, the first endplate 32 illustrated in FIGS. 12A-I rotates axially about the transverse axis at a slower rated compared to the first endplate illustrated in FIGS. 6A-I. As the radius of curvature decreases, the location of the axis of rotation 2 (see FIG. 1A) becomes more specific and fixed. As the radius of curvature increases, the location of the axis of rotation 2 becomes less specific, and therefore more compliant with respect to anatomical variations in the vertebral bodies that define the intervertebral space into which the intervertebral implant 30 is inserted.

Referring now to FIGS. 1A and 14A-H, the intervertebral implant 30 can further promote lateral bending of the first endplate 32 during axial rotation of the first endplate 32 in the manner described above. Thus, when a force is applied to the first endplate 32 that drives the first endplate 32 to rotate about a substantially transverse axis so as to undergo axial rotation, the intervertebral implant 30, and in particular the second endplate 34, also induces the first endplate 32 to rotate about a substantially longitudinal axis, thereby promoting lateral bending. Accordingly, during operation, the first and second articulation members 58 and 60 can ride along the third and fourth articulation members 62 and 64, respectively, such that rotation of the first endplate 32 about a first axis of rotation that is substantially perpendicular to the insertion direction induces rotation of the first endplate 32 about a second axis of rotation that is substantially perpendicular to the first axis of rotation.

For instance, as illustrated in FIGS. 14A-E, during axial rotation, or rotational movement of the first endplate 32 with respect to the second endplate 34 about a transverse axis of rotation, one of the first and second contact locations 71a and 71b of the second articulation member 60 travels along the complementary first and second contact locations 88a and 88b of the fourth articulation member 64 along a first direction, and the other of the first and second contact locations 71a and 71b of the second articulation member 60 travels along the complementary first and second contact locations 88a and 88b of the fourth articulation member 64 along a second direction that is opposite the first direction. It should be appreciated that during axial rotation, because the first and second contact locations 88a and 88b are curved along a concave path in the transverse direction T as the extend in the longitudinal direction L, and the concave path is sloped greater than the linear path defined in FIGS. 7A-H, the central longitudinal and lateral axes 49 and 51 of the first endplate become angularly offset with respect to the central longitudinal and lateral axes 55 and 55 of the second endplate 34 at a greater rate than the intervertebral implant 30 as described above with respect to FIGS. 7A-H.

Figure 14A:
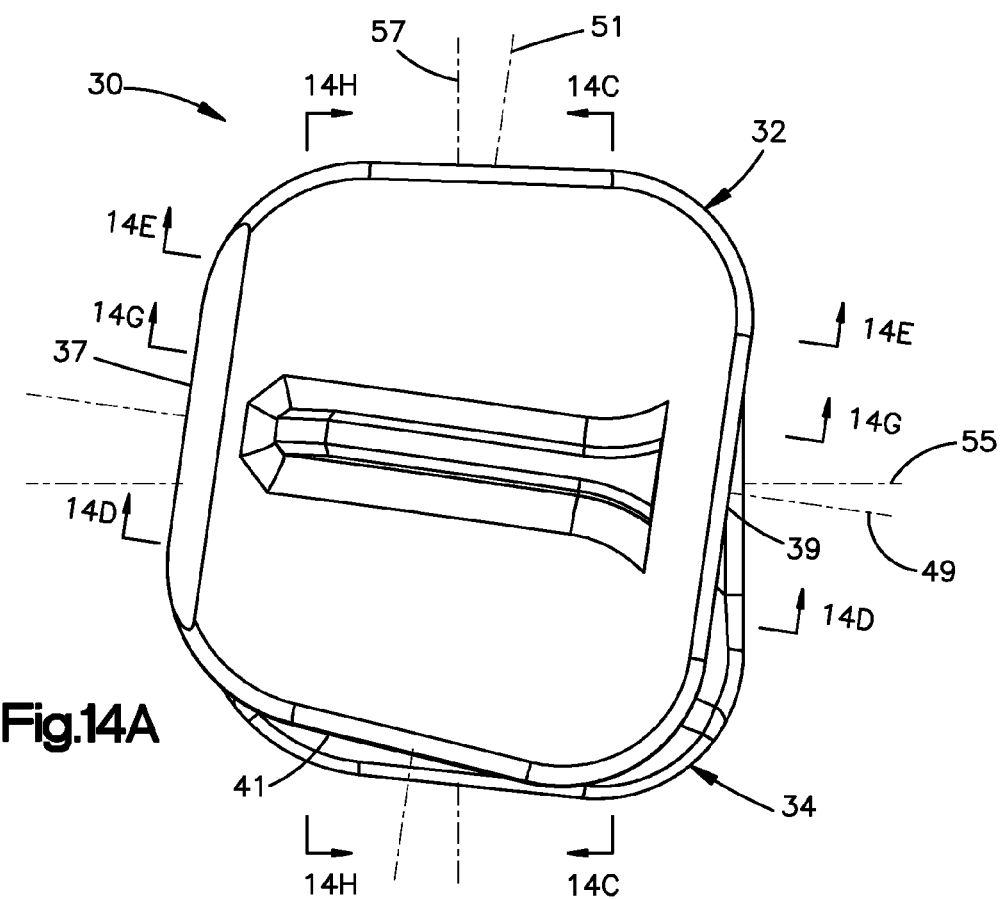
FIG. 14A is a top plan view of the intervertebral implant illustrated in FIG. 1B, but showing the upper endplate axially rotated with respect to the lower endplate, during axial rotation.
Figure 14B:
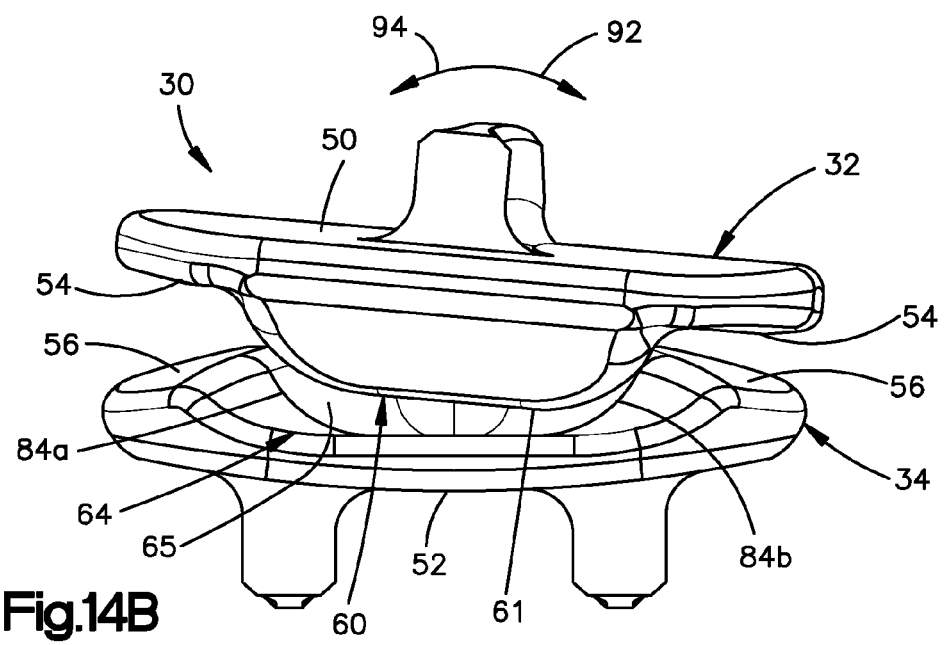
FIG. 14B is a rear elevation view of the intervertebral implant illustrated in FIG. 14A, taken at line 14C-14C.
Figure 14C:
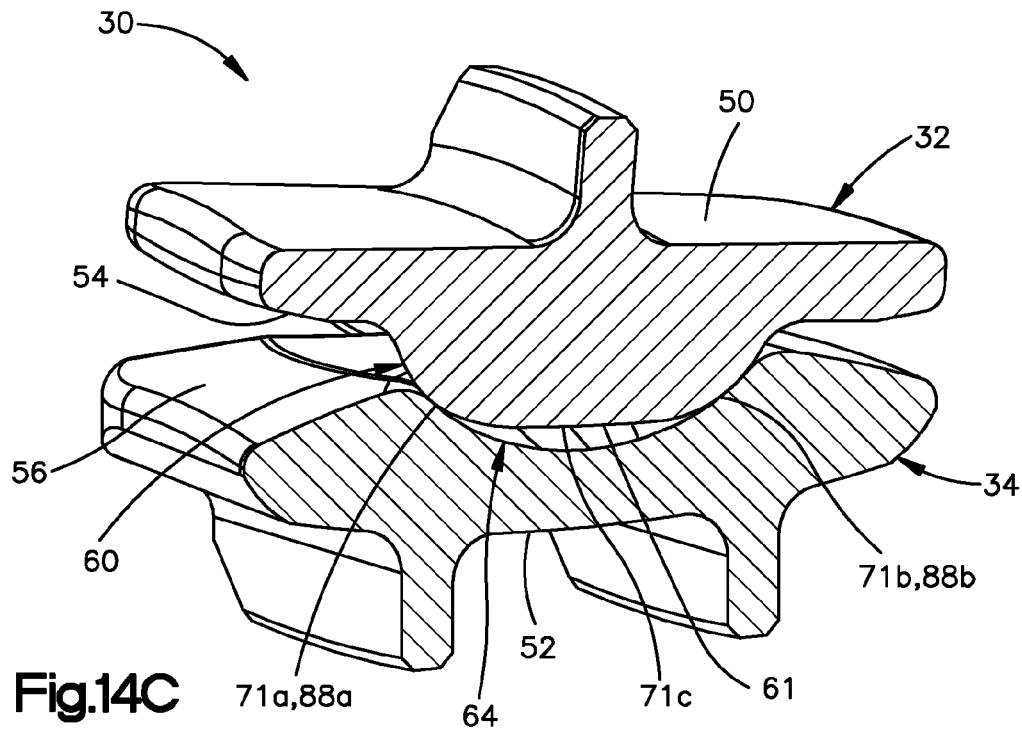
FIG. 14C is a cross-sectional view of the intervertebral implant illustrated in FIG. 14A, taken at line 14C-14C.
Figure 14D:
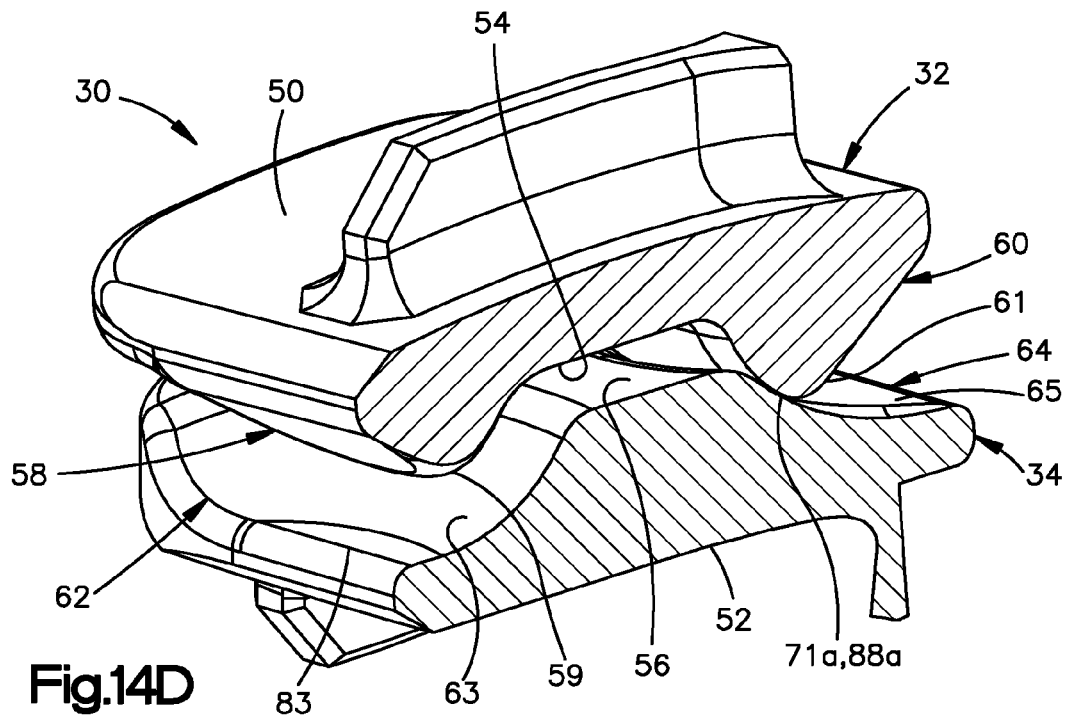
FIG. 14D is a cross-sectional view of the intervertebral implant illustrated in FIG. 14A, taken at line 14D-14D.
Figure 14E:
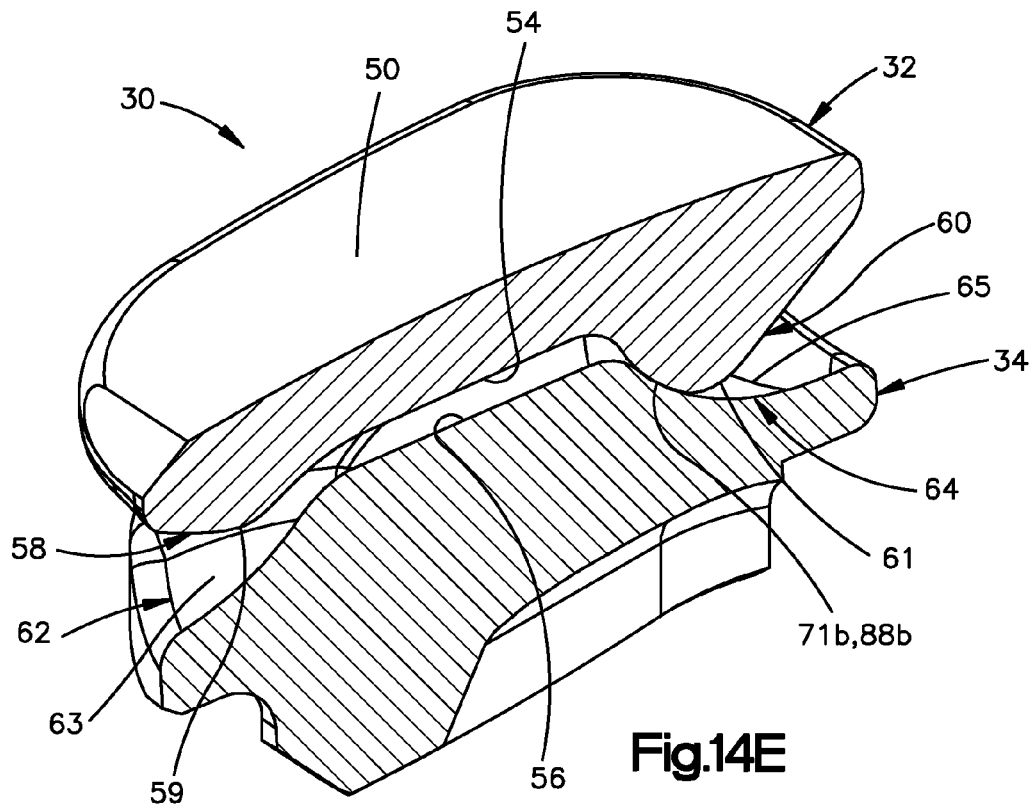
FIG. 14E is a cross-sectional view of the intervertebral implant illustrated in FIG. 14A, taken at line 14E-14E.
Figure 14F:
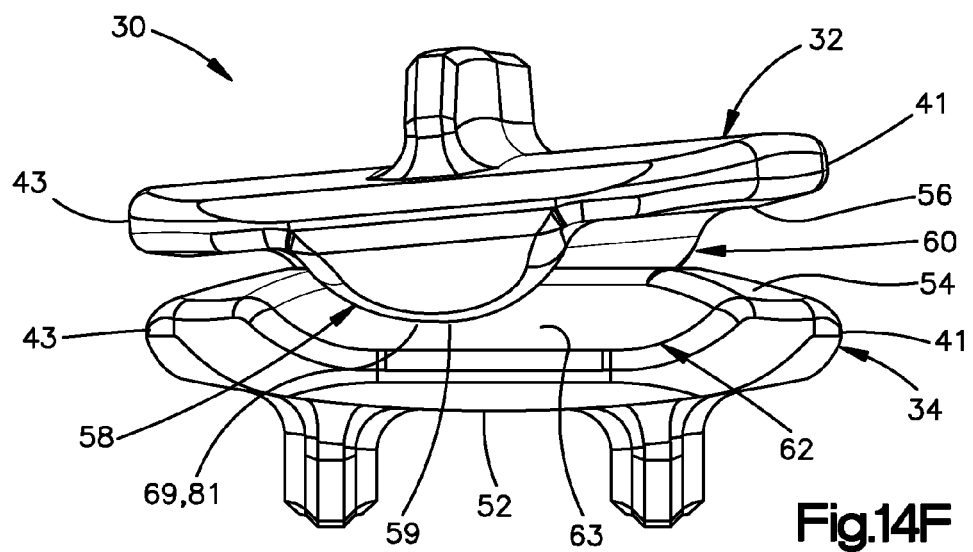
FIG. 14F is a front elevation view of the intervertebral implant illustrated in FIG. 14A.
Figure 14G:
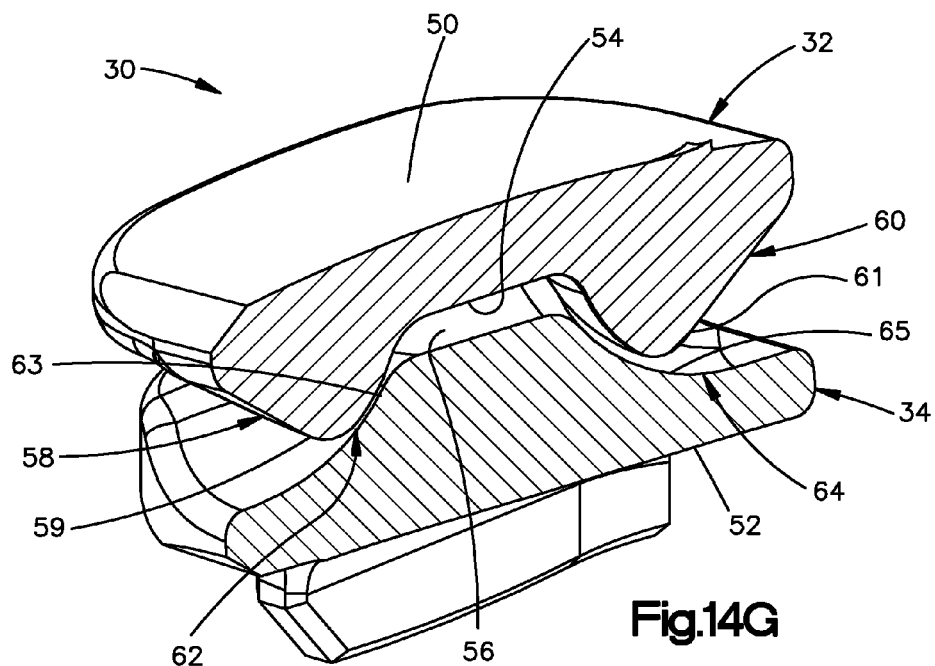
FIG. 14G is a cross-sectional view of the intervertebral implant illustrated in FIG. 14A, taken at medial-lateral midline 14G-14G.
Figure 14H:
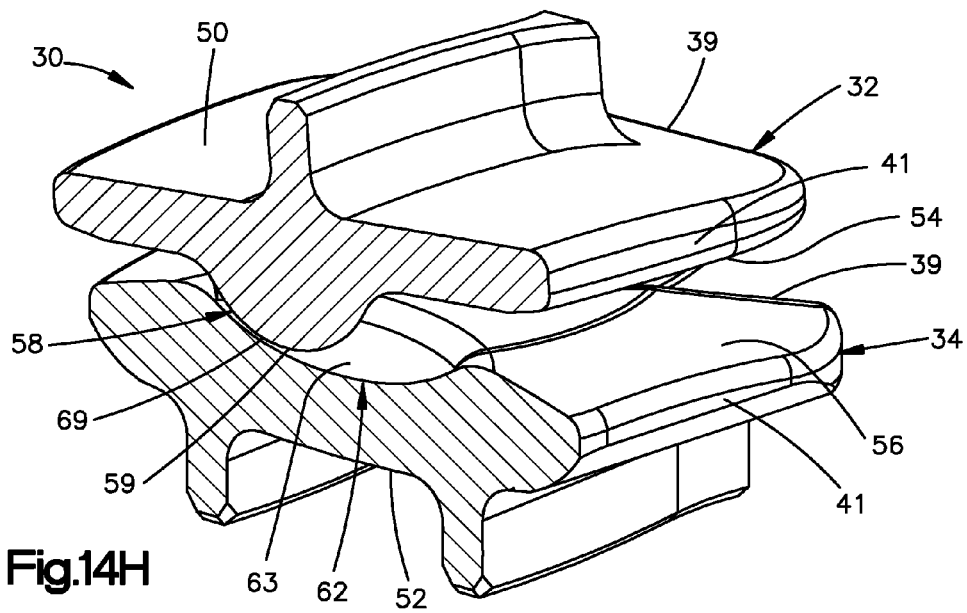
FIG. 14H is a cross-sectional view of the intervertebral implant illustrated in FIG. 14A, taken at line 14H-14H.

Referring also to FIGS. 14F-H, as the first contact location 71a moves forward along the longitudinal direction L and the second contact location 71b moves rearward along the longitudinal direction L, the first endplate 32 rotates about the transverse axis 95. As the first endplate 32 rotates about the axis 95, the contact location 69 of the first articulation member 58 translates along the contact location 81 that is defined by the third articulation surface 63. Because the contact location 81 is curved in the manner described above, the contact location 69 travels up along the transverse direction T during axial rotation of the first endplate 32, which causes the corresponding one of the sides 41 or 43 to likewise travel up along the transverse direction T while the other of the sides 41 or 43 travels down along the transverse direction. As a result, the intervertebral implant 30 illustrated in FIGS. 14A-H induces lateral bending of the first endplate 32 at a greater rate than the endplate illustrated in FIGS. 7A-H. Because the third articulation surface 63 extends upward along the transverse direction T as it extends outward along the lateral direction A away from the central longitudinal axis 49, the contact location 69 of the first articulation member 58 likewise travels up along the transverse direction T as the first endplate 32 axially rotates, which causes the induced lateral bending to occur at a faster rate with respect to the third articulation surface 63 extending substantially along the lateral direction A without extending in the transverse direction along a laterally outward direction of travel, as illustrated in FIGS. 7F-H.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. An intervertebral implant configured to be inserted along a direction of insertion into an intervertebral space disposed between first and second vertebrae, the intervertebral implant comprising:
    a first endplate having a front end and a rear end spaced from the front end along the direction of insertion into the intervertebral space, the first endplate including a first endplate body, a first articulation member that is supported by the first endplate body at a location proximate to the front end, and at least one second articulation member that is supported by the first endplate body at a location proximate to the rear end, wherein the second articulation member defines a first contact location and a second contact location, the second contact location being spaced to the right of the first contact location from a view of the first end plate in a direction from the rear end to the front end; and
    a second endplate having a front end and a rear end spaced from the front end along the direction of insertion into the intervertebral space, the second endplate including a second endplate body, a third articulation member supported by the second endplate body at a location proximate to the front end of the second endplate, and a fourth articulation member supported by the second endplate body at a location proximate to the rear end of the second endplate,
    wherein the first articulation member defines a point contact location that rides on and along an articulation surface defined by the third articulation member, and the first and second contact locations ride on and along the fourth articulation member, such that an axial rotative force applied to the first endplate in a clockwise direction, from a view of the first endplate in a direction from the first endplate toward the second endplate, causes 1) the first contact location to ride on and along the fourth articulation member in a direction away from the second endplate, and 2) the second contact location to ride on and along the fourth articulation member in a transverse direction toward the second endplate , and
    wherein the first endplate is disposed upward of the second endplate along the transverse direction, and the articulation surface 1) extends upward as it extends toward the rear end of the second endplate, and 2) is substantially planar as it extends toward the rear end of the second endplate.

2. The intervertebral implant as recited in claim 1, wherein the first endplate body defines an outer surface configured to face the first vertebra and an inner surface that is spaced from the outer surface along the transverse direction, the first endplate defines a first axis of rotation, and the rotative force is applied about the first axis.

3. The intervertebral implant as recited in claim 2, wherein the axial rotative force applied to the first endplate in the clockwise direction induces rotation of the first endplate about a second axis of rotation that is substantially perpendicular to the first axis of rotation.

4. The intervertebral implant as recited in claim 3, wherein the second axis of rotation is substantially parallel to the direction of insertion when the first axis of rotation is substantially in the transverse direction.

5. The intervertebral implant as recited in claim 4, wherein the first endplate body defines an outer surface configured to face the first vertebra and an inner surface that is spaced from the outer surface along the transverse direction.

6. The intervertebral implant as recited in claim 5, wherein the first endplate travels along a concave path of motion with respect to the second endplate when the first endplate moves about a third axis that is perpendicular to each of the first axis of rotation and the second axis of rotation.

7. The intervertebral implant as recited in claim 2, wherein the first endplate travels along a concave path of motion with respect to the second endplate when the first axis of rotation is substantially in the transverse direction.

8. The intervertebral implant as recited in claim 1, wherein the first and second contact locations are spaced from each other and define respective point contact locations that travel on and along an articulation surface defined by the fourth articulation member.

9. The intervertebral implant as recited in claim 8, wherein the first endplate is disposed upward of the second endplate along the transverse direction, and the articulation surface of the fourth articulation member extends upward as it extends along the direction of insertion.

10. The intervertebral implant as recited in claim 9, wherein the articulation surface of the fourth articulation member is substantially planar as it extends along the direction of insertion.

11. The intervertebral implant as recited in claim 9, wherein the second endplate defines first and second sides that are spaced from each other along a lateral direction and extend between the front and rear ends of the second endplate, and the articulation surface of the fourth articulation member is defined by a pair of side walls that converge toward each other along the lateral direction as they extend along the direction of insertion.

12. The intervertebral implant as recited in claim 11, wherein each of the pair of side walls curves along the lateral direction as they converge toward each other along the direction of insertion.

13. The intervertebral implant as recited in claim 1, wherein the second endplate defines first and second sides that are spaced from each other along a lateral direction and extend between the front and rear ends of the second endplate, and the articulation surface extends substantially straight along the lateral direction.

14. The intervertebral implant as recited in claim 1, wherein the first and second articulation members protrude from the first endplate body toward the second endplate body, and the third and fourth articulation members are recessed in the second endplate body.

15. The intervertebral implant as recited in claim 14, wherein the fourth articulation member defines first and second side walls that face a plane defined by the insertion direction and the transverse direction, the first contact location rides along the first side wall, and the second contact location rides along the second side wall.

16. An intervertebral implant configured to be inserted along a direction of insertion into an intervertebral space disposed between first and second vertebrae, the intervertebral implant comprising:
a first endplate having a front end and a rear end spaced from the front end along the direction of insertion into the intervertebral space, the first endplate including a first endplate body, a first articulation member that is supported by the first endplate body at a location proximate to the front end, and at least one second articulation member that is supported by the first endplate body at a location proximate to the rear end, wherein the second articulation member defines a first contact location and a second contact location, the second contact location being spaced to the right of the first contact location from a view of the first end plate in a direction from the rear end to the front end;
a second endplate having a front end and a rear end spaced from the front end along the direction of insertion into the intervertebral space, and first and second sides that are spaced from each other along a lateral direction and extend between the front and rear ends of the second endplate, the second endplate including a second endplate body, a third articulation member supported by the second endplate body at a location proximate to the front end of the second endplate, and a fourth articulation member supported by the second endplate body at a location proximate to the rear end of the second endplate;
wherein the first articulation member defines a point contact location that rides on and along an articulation surface that is defined by the third articulation member and extends substantially straight along the lateral direction, and the first and second contact locations ride on and along the fourth articulation member, such that an axial rotative force applied to the first endplate in a clockwise direction, from a view of the first endplate in a direction from the first endplate toward the second endplate, causes 1) the first contact location to ride on and along the fourth articulation member in a direction away from the second endplate, and 2) the second contact location to ride on and along the fourth articulation member in a transverse direction toward the second endplate, and
wherein the first endplate is disposed upward of the second endplate along the transverse direction, and the articulation surface extends upward as it extends toward the rear end of the second endplate.

17. The intervertebral implant as recited in claim 16, wherein the first endplate body defines an outer surface configured to face the first vertebra and an inner surface that is spaced from the outer surface along the transverse direction, the first endplate defines a first axis of rotation, and the rotative force is applied about the first axis.

18. The intervertebral implant as recited in claim 17, wherein the first endplate travels along a concave path of motion with respect to the second endplate when the first axis of rotation is substantially in the transverse direction.

19. The intervertebral implant as recited in claim 17, wherein the axial rotative force applied to the first endplate in the clockwise direction induces rotation of the first endplate about a second axis of rotation that is substantially perpendicular to the first axis of rotation.

20. The intervertebral implant as recited in claim 19, wherein the second axis of rotation is substantially parallel to the direction of insertion when the first axis of rotation is substantially in the transverse direction.

21. The intervertebral implant as recited in claim 20, wherein the first endplate body defines an outer surface configured to face the first vertebra and an inner surface that is spaced from the outer surface along the transverse direction.

22. The intervertebral implant as recited in claim 21, wherein the first endplate travels along a concave path of motion with respect to the second endplate when the first endplate moves about a third axis that is perpendicular to each of the first axis of rotation and the second axis of rotation.

23. The intervertebral implant as recited in claim 16, wherein the first and second contact locations are spaced from each other and define respective point contact locations that travel on and along an articulation surface defined by the fourth articulation member.

24. An intervertebral implant configured to be inserted along a direction of insertion into an intervertebral space disposed between first and second vertebrae, the intervertebral implant comprising:
a first endplate having a front end and a rear end spaced from the front end along the direction of insertion into the intervertebral space, the first endplate including a first endplate body, a first articulation member that is supported by the first endplate body at a location proximate to the front end, and at least one second articulation member that is supported by the first endplate body at a location proximate to the rear end, wherein the second articulation member defines a first contact location and a second contact location spaced from the first contact location, the second contact location being spaced to the right of the first contact location from a view of the first end plate in a direction from the rear end to the front end; and a second endplate having a front end and a rear end spaced from the front end along the direction of insertion into the intervertebral space, the second endplate including a second endplate body, a third articulation member supported by the second endplate body at a location proximate to the front end of the second endplate, and a fourth articulation member supported by the second endplate body at a location proximate to the rear end of the second endplate, wherein the first articulation member defines a point contact location that rides on and along an articulation surface defined by the third articulation member, and the first and second contact locations ride on and along the fourth articulation member, such that an axial rotative force applied to the first endplate in a clockwise direction, from a view of the first endplate in a direction from the first endplate toward the second endplate, causes 1) the first contact location defining a point contact location to ride on and along, in a direction away from the second endplate, an articulation surface defined by the fourth articulation member, and 2) the second contact location to ride on and along, in a transverse direction toward the second endplate, the articulation surface defined by the fourth articulation member, and wherein the first endplate is disposed upward of the second endplate along the transverse direction, and the articulation surface of the fourth articulation member 1) extends upward as it extends along the direction of insertion, and 2) is substantially planar as it extends along the direction of insertion.

* * * * *